US012565537B2

(12) United States Patent (10) Patent No.: US 12,565,537 B2
O'Bryan et al. (45) Date of Patent: Mar. 3, 2026

(54) COMPOSITIONS AND METHODS TARGETING THE NUCLEOTIDE FREE STATE OF RAS TO BLOCK ONCOGENIC SIGNALING AND TRANSFORMATION

(71) Applicants:MUSC Foundation for Research Development, Charleston, SC (US); New York University, New York, NY (US); The United States Government as Represented by the Department of Veterans Affairs, Washington, DC (US)

(72) Inventors: John O'Bryan, Charleston, SC (US); Shohei Koide, New York, NY (US); Akiko Koide, New York, NY (US)

(73) Assignees: MUSC Foundation for Research Development, Charleston, SC (US); New York University, New York, NY (US); The United States Government as Represented by the Department of Veterans Affairs, Washington, DC (US)

( * ) Notice: Subject to any disclaimer, the term of this patent is extended or adjusted under 35 U.S.C. 154(b) by 929 days.

(21) Appl. No.: 17/620,395

(22) PCT Filed: Jun. 18, 2020

(86) PCT No.: PCT/US2020/038363
§ 371 (c)(1),
(2) Date: Dec. 17, 2021

(87) PCT Pub. No.: WO2020/257405
PCT Pub. Date: Dec. 24, 2020

(65) Prior Publication Data
US 2022/0324998 A1     Oct. 13, 2022

Related U.S. Application Data

(60) Provisional application No. 62/862,924, filed on Jun. 18, 2019.

(51) Int. Cl.
| | |
|---|---|
| *C07K 16/32* | (2006.01) |
| *A61K 39/00* | (2006.01) |
| *A61K 39/395* | (2006.01) |
| *A61P 35/00* | (2006.01) |
| *G01N 33/574* | (2006.01) |

(52) U.S. Cl.
CPC ........ *C07K 16/32* (2013.01); *A61K 39/39558* (2013.01); *A61P 35/00* (2018.01); *G01N 33/5748* (2013.01); *A61K 2039/505* (2013.01); *C07K 2317/569* (2013.01); *C07K 2317/76* (2013.01); *C07K 2317/92* (2013.01); *C07K*

*2319/30* (2013.01); *G01N 2333/914* (2013.01); *G01N 2500/04* (2013.01)

(58) Field of Classification Search
None
See application file for complete search history.

(56) References Cited

U.S. PATENT DOCUMENTS

| | | | |
|---|---|---|---|
| 2002/0143164 A1 | 10/2002 | Rotin | |
| 2008/0027135 A1 | 1/2008 | Sondek | |
| 2016/0356768 A1 | 12/2016 | Salafsky | |
| 2017/0253644 A1 | 9/2017 | Steyaert | |
| 2018/0282397 A1 | 10/2018 | Cetin | |
| 2019/0119358 A1 | 4/2019 | Josephson | |
| 2022/0324998 A1* | 10/2022 | O'Bryan | ............... G01N 33/53 |

FOREIGN PATENT DOCUMENTS

| | | |
|---|---|---|
| WO | 2019086548 | 5/2019 |

OTHER PUBLICATIONS

Patgiri et al., An Orthosteric Inhibitor of the Ras-Sos Interaction, Nat Chem Biol., with Suppl., Publication Date: Jul. 17, 2011 (Year: 2011).*

Zhang et al., Antibody mimetics: The next generation antibody engineering, a retrospective and prospective analysis, Biotechnology Journal, 2024: 19: 2300532 (Year: 2024).*

Koide et al., Teaching an Old Scaffold New Tricks: Monobodies Constructed Using Alternative Surfaces of the FN3 Scaffold, J. Mol. Biol. 2012, 415, 393-405, Publication Date: Dec. 16, 2011 (Year: 2012).*

Spencer-Smith et al., Inhibition of RAS function through targeting an allosteric regulatory site, Nature Chemical Biology, vol. 13, 62-68, with Online Methods Publication Date: Nov. 7, 2016 (Year: 2016).*

Koide et al., "Teaching an old scaffold new tricks: monobodies constructed using alternative surfaces of the FN3 scaffold," J Mol Biol. Jan. 13, 2012;415(2):393-405.

Spencer-Smith et al., "Direct inhibition of RAS: Quest for the Holy Grail?", Semin Cancer Biol, (20171214), vol. 54, pp. 138-148, XP055776296.

(Continued)

*Primary Examiner* — Samira J Jean-Louis
*Assistant Examiner* — Cheng Lu
(74) *Attorney, Agent, or Firm* — Riverside Law LLP

(57) ABSTRACT

The invention provides compositions and methods for binding Ras in a nucleotide free state (apo RAS) and inhibiting Ras signaling. In one embodiment, the invention provides monobodies that specifically bind apo RAS and methods of use. Thus, in diseases and conditions where a reduction of Ras signaling is beneficial, such inhibitory compositions act as therapeutics.

6 Claims, 35 Drawing Sheets

Specification includes a Sequence Listing.

(56)                    References Cited

OTHER PUBLICATIONS

Wojcik et al., "A potent and highly specific FN3 monobody inhibitor of the Abl SH2 domain," Nat Struct Mol Biol. Apr. 2010;17(4):519-27.

Wong et al., "A new dimension to Ras function: a novel role for nucleotide-free Ras in Class II phosphatidylinositol 3-kinase beta (PI3KC2β) regulation," PLoS One. 2012;7(9):e45360.

* cited by examiner

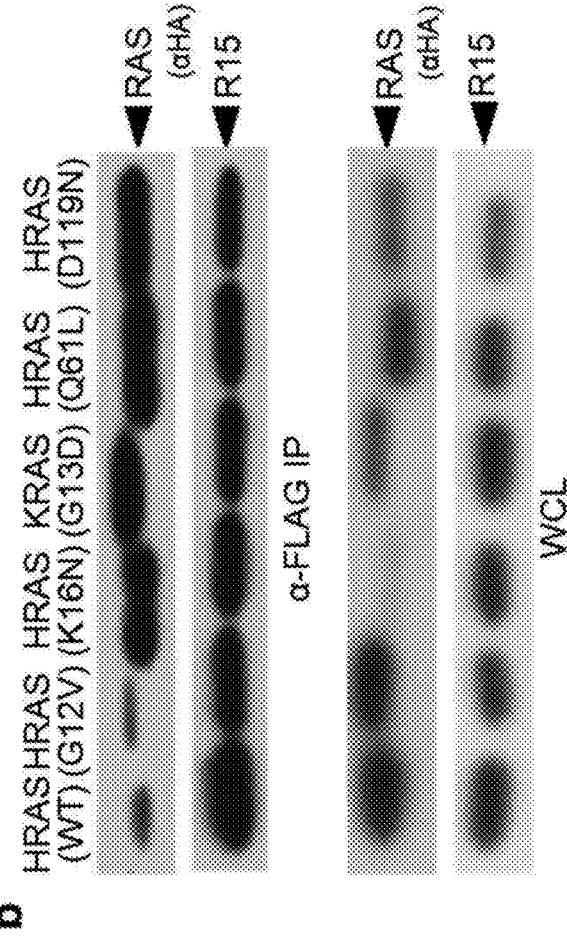
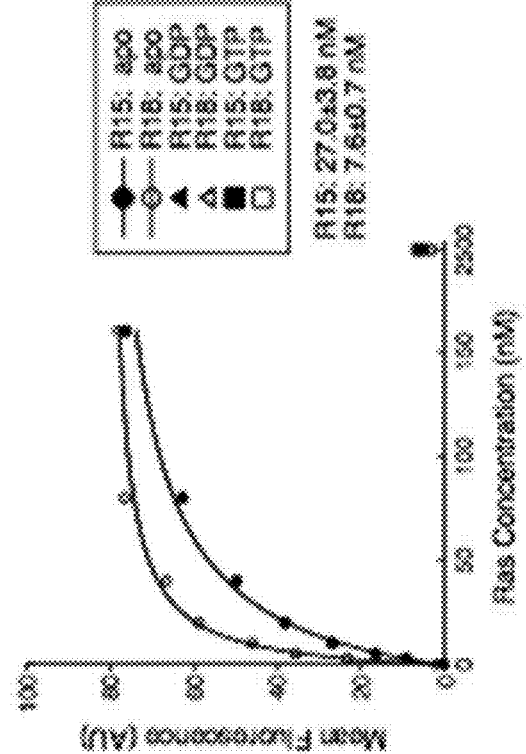
Figure 1A-B

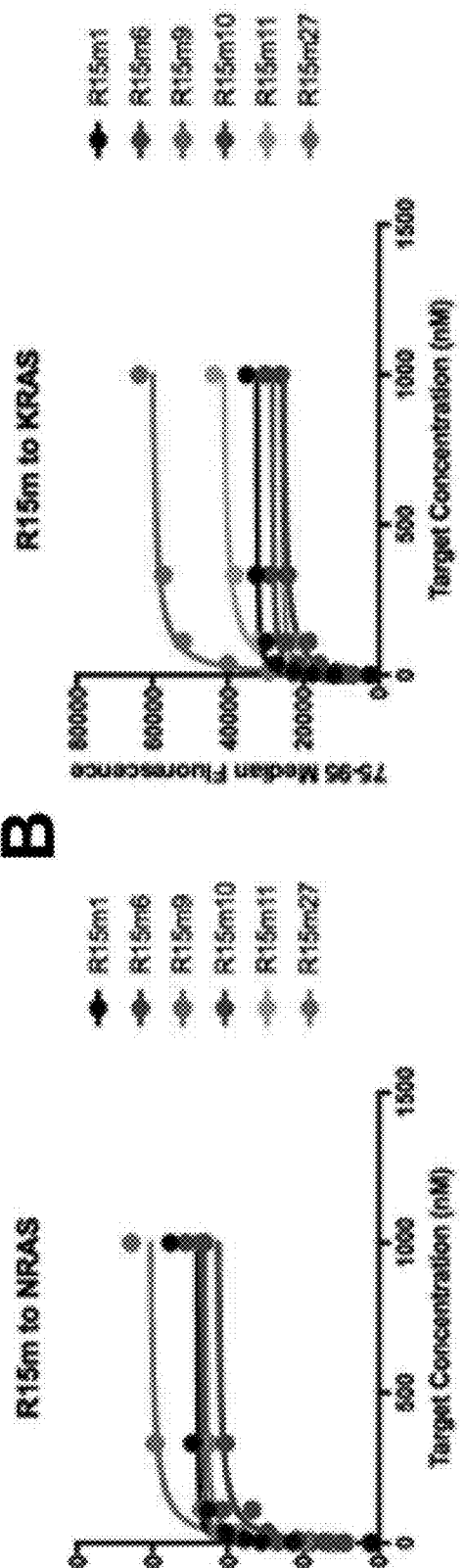
Figure 2A-B

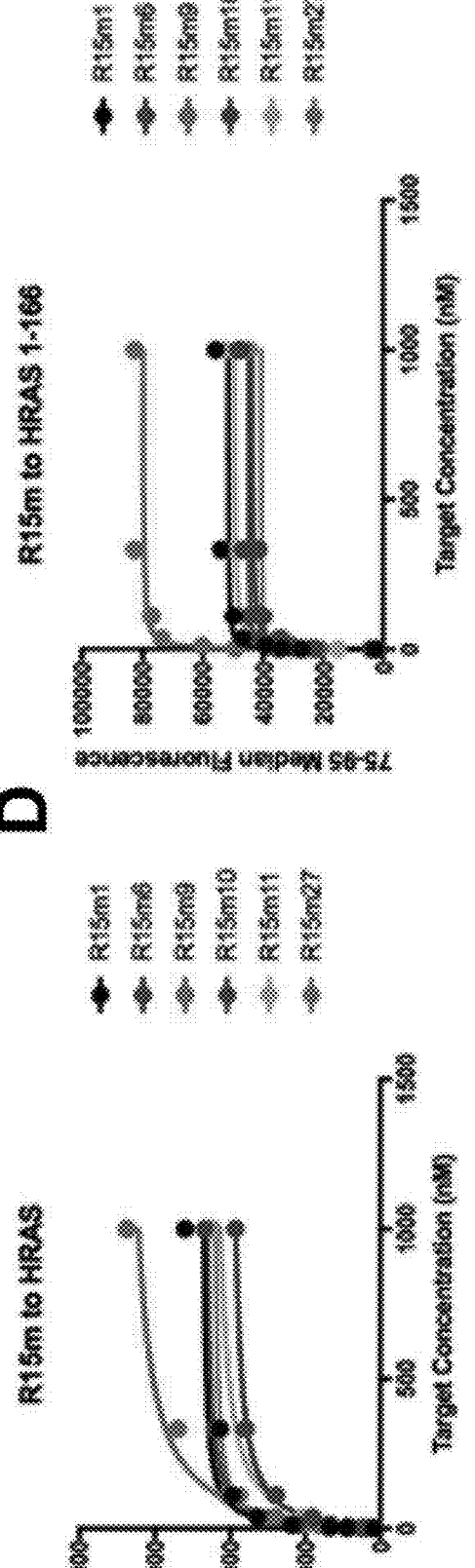
Figure 2C-D

E

| NRAS | R15m1 | R15m6 | R15m9 | R15m10 | R15m11 | R15m27 |
|---|---|---|---|---|---|---|
| Kd (nM) | 2.72 | 17.9 | 17.0 | 3.48 | 23.5 | 8.10 |
| Error (nM) | 1.2 | 6.5 | 5.9 | 1.1 | 7.0 | 1.8 |

| KRAS | R15m1 | R15m6 | R15m9 | R15m10 | R15m11 | R15m27 |
|---|---|---|---|---|---|---|
| Kd (nM) | 4.93 | 34.6 | 17.0 | 9.69 | 31.0 | 9.55 |
| Error (nM) | 1.4 | 13. | 5.0 | 4.4 | 10. | 4.4 |

| HRAS | R15m1 | R15m6 | R15m9 | R15m10 | R15m11 | R15m27 |
|---|---|---|---|---|---|---|
| Kd (nM) | 17.5 | 49.8 | 73.6 | 21.3 | 63.3 | 17.6 |
| Error (nM) | 5.4 | 11. | 16. | 4.1 | 20. | 3.4 |

| HRAS SF | R15m1 | R15m6 | R15m9 | R15m10 | R15m11 | R15m27 |
|---|---|---|---|---|---|---|
| Kd (nM) | 2.22 | 6.05 | 2.76 | 2.00 | 6.13 | 2.61 |
| Error (nM) | 0.76 | 2.4 | 0.61 | 0.59 | 1.60 | 0.99 |

Figure 2E

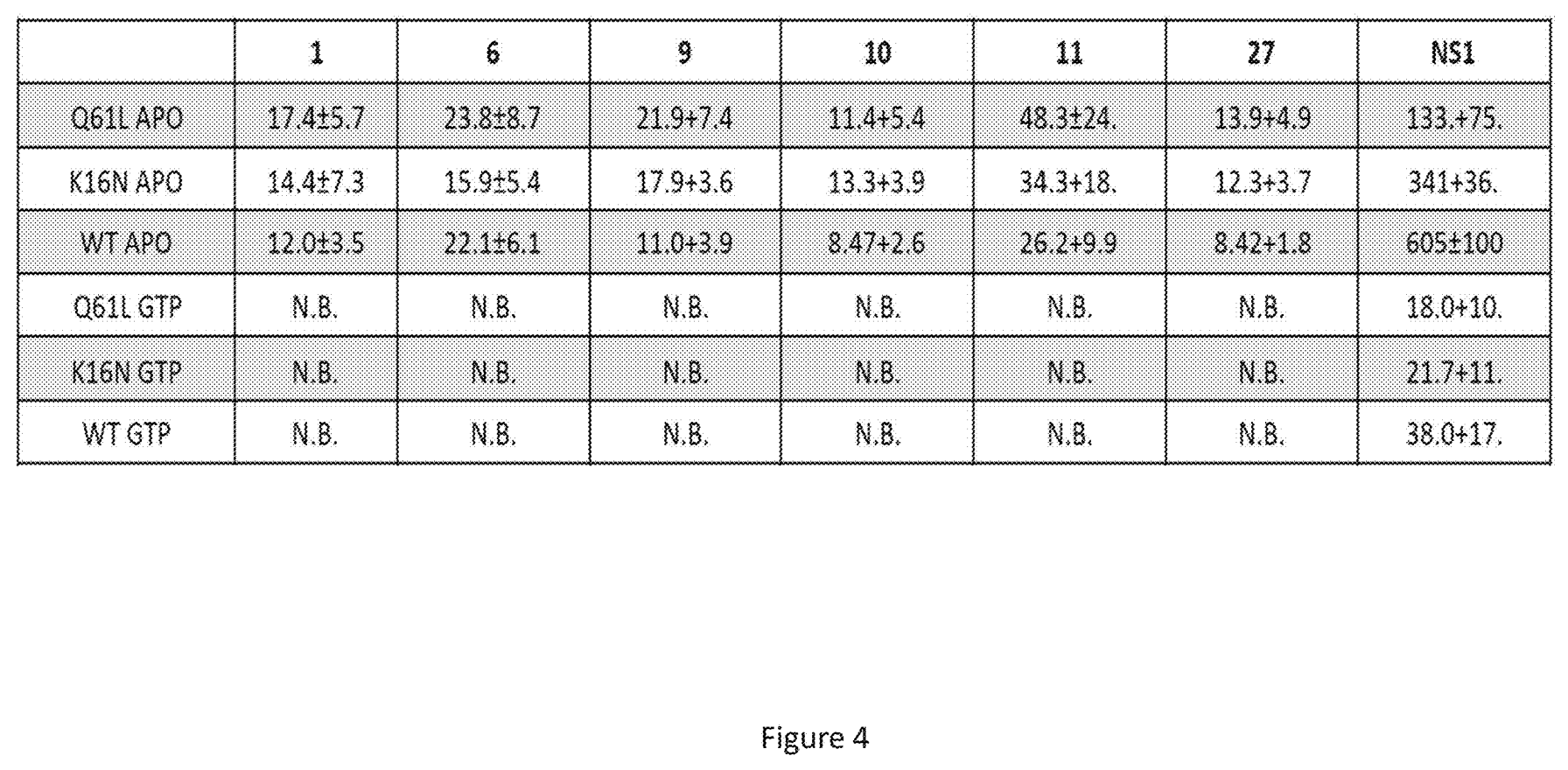

| | 1 | 6 | 9 | 10 | 11 | 27 | NS1 |
|---|---|---|---|---|---|---|---|
| Q61L APO | 17.4±5.7 | 23.8±8.7 | 21.9±7.4 | 11.4±5.4 | 48.3±24. | 13.9±4.9 | 133.±75. |
| K16N APO | 14.4±7.3 | 15.9±5.4 | 17.9±3.6 | 13.3±3.9 | 34.3±18. | 12.3±3.7 | 34.1±36. |
| WT APO | 12.0±3.5 | 22.1±6.1 | 11.0±3.9 | 8.47±2.6 | 26.2±9.9 | 8.42±1.8 | 60.5±100 |
| Q61L GTP | N.B. | N.B. | N.B. | N.B. | N.B. | N.B. | 18.0+10. |
| K16N GTP | N.B. | N.B. | N.B. | N.B. | N.B | N.B. | 21.7+11. |
| WT GTP | N.B. | N.B. | N.B. | N.B. | N.B. | N.B. | 38.0+17. |

Figure 4

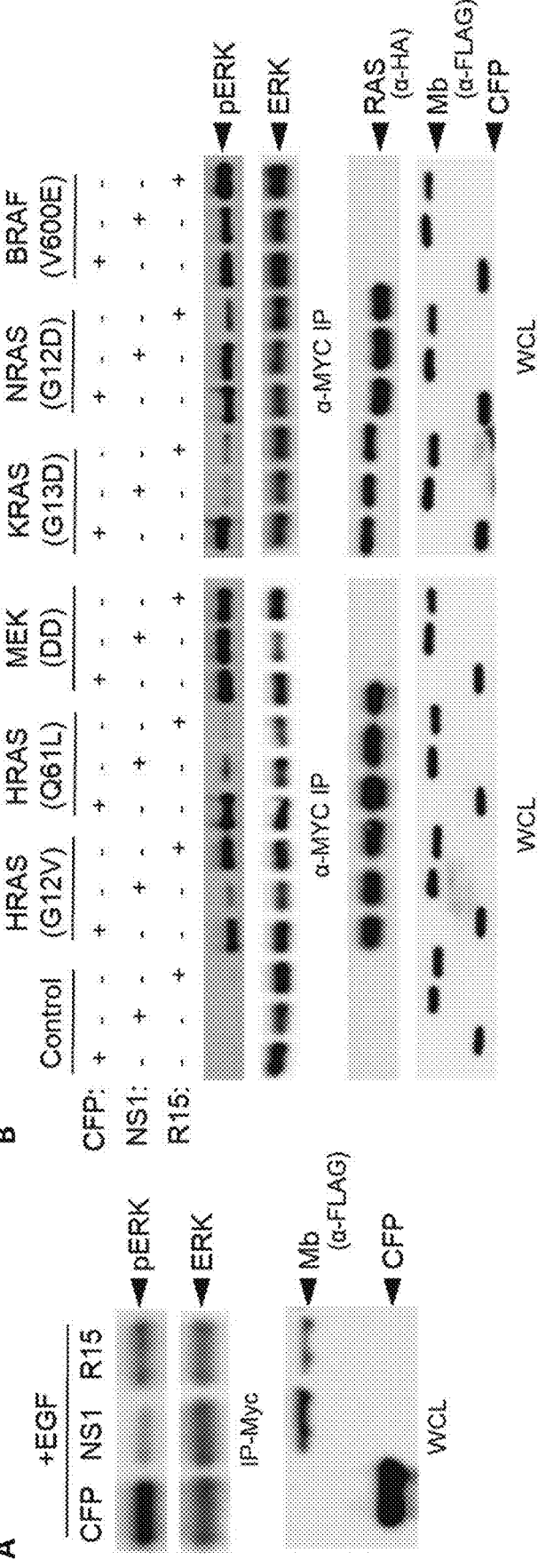
Figure 9A-B

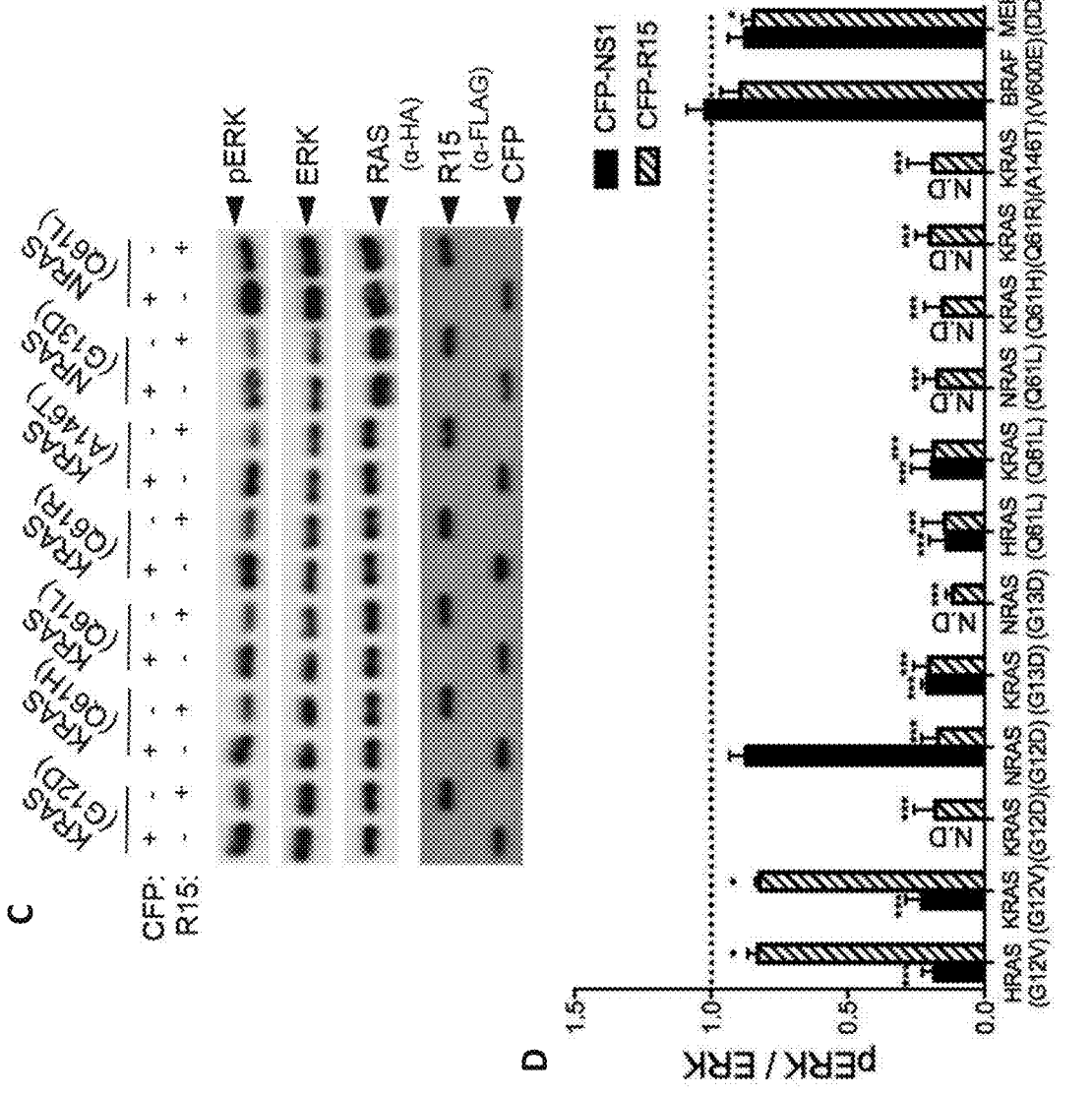
Figure 9C-D

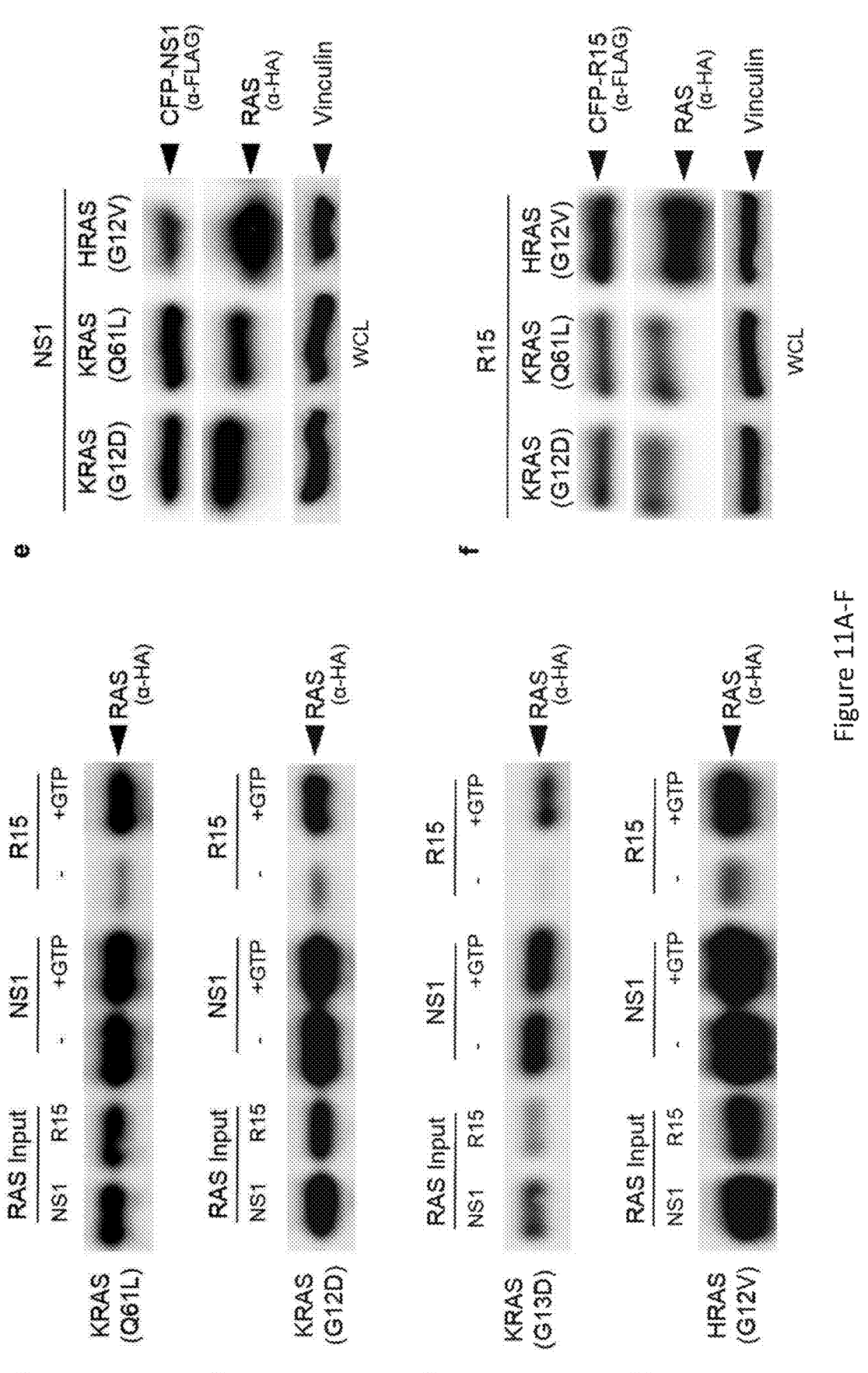
Figure 11A-F

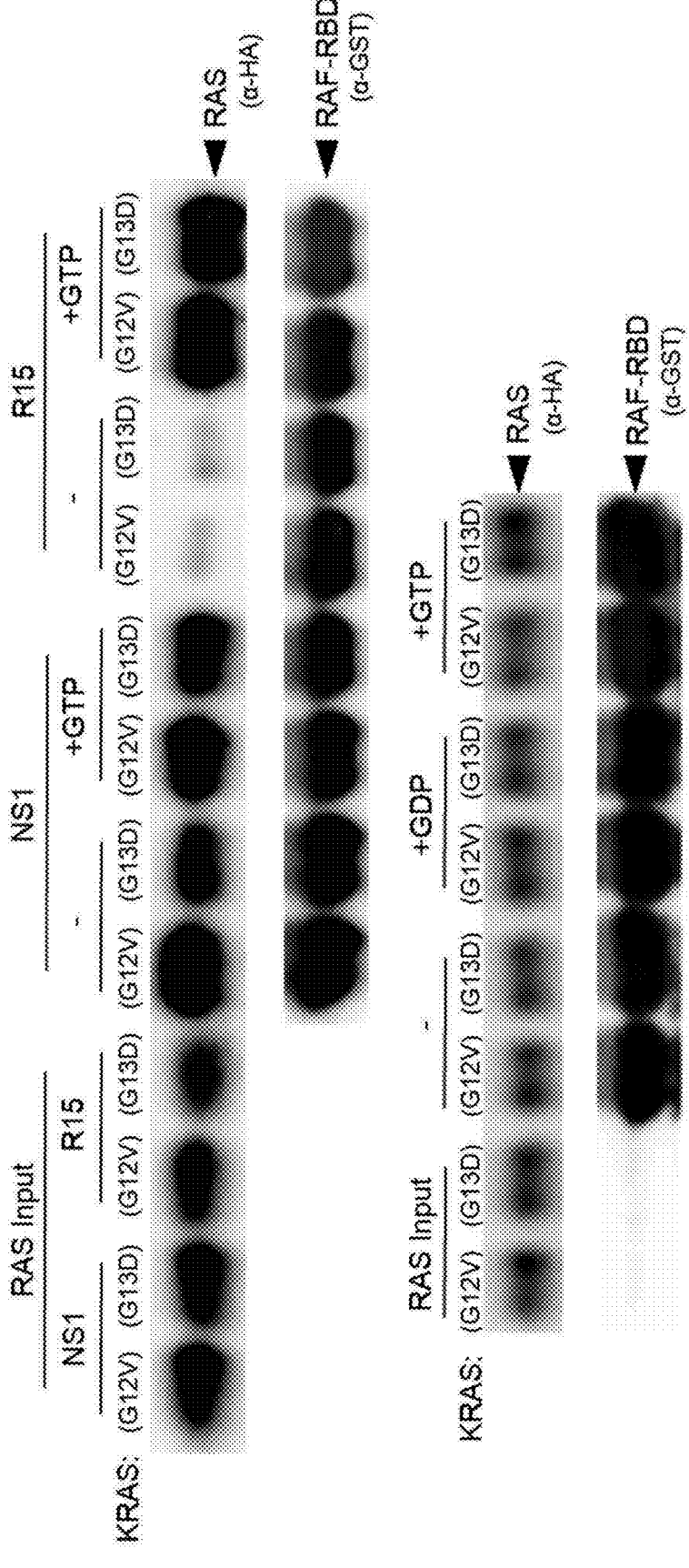
Figure 12A-B

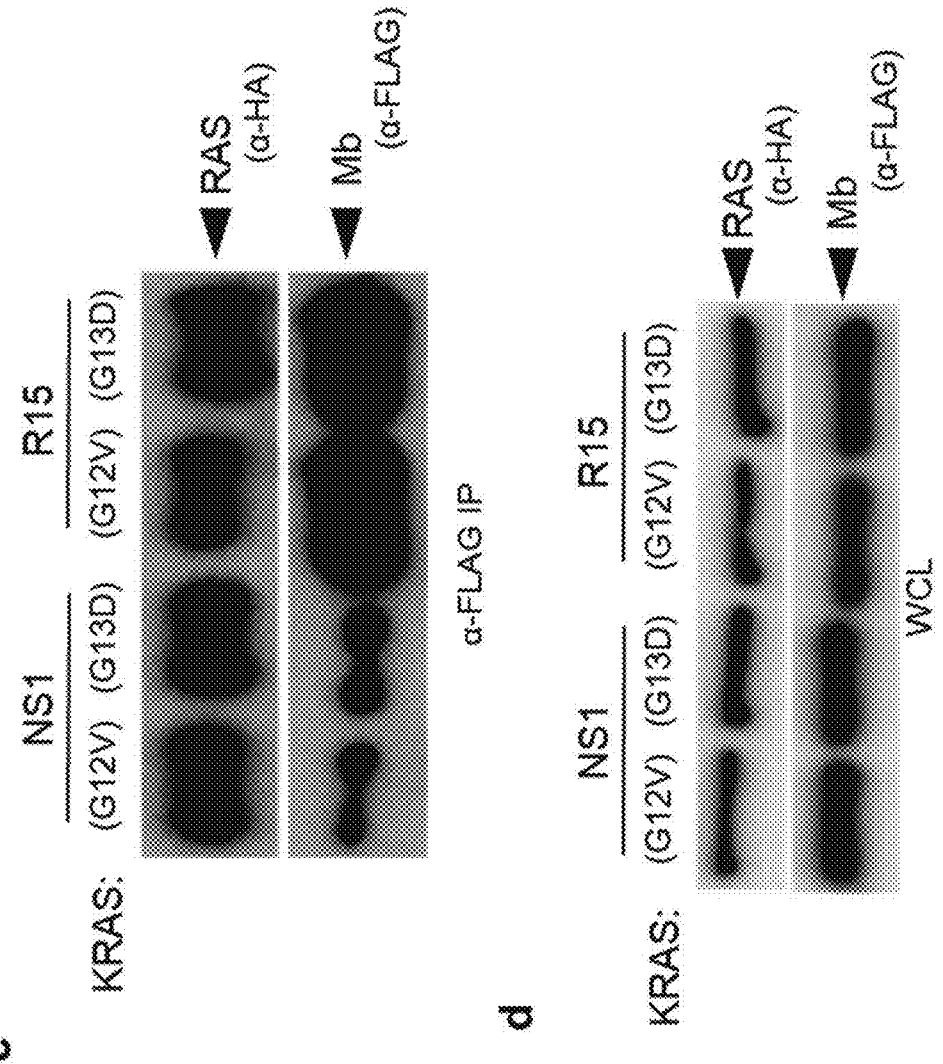
Figure 12C-D

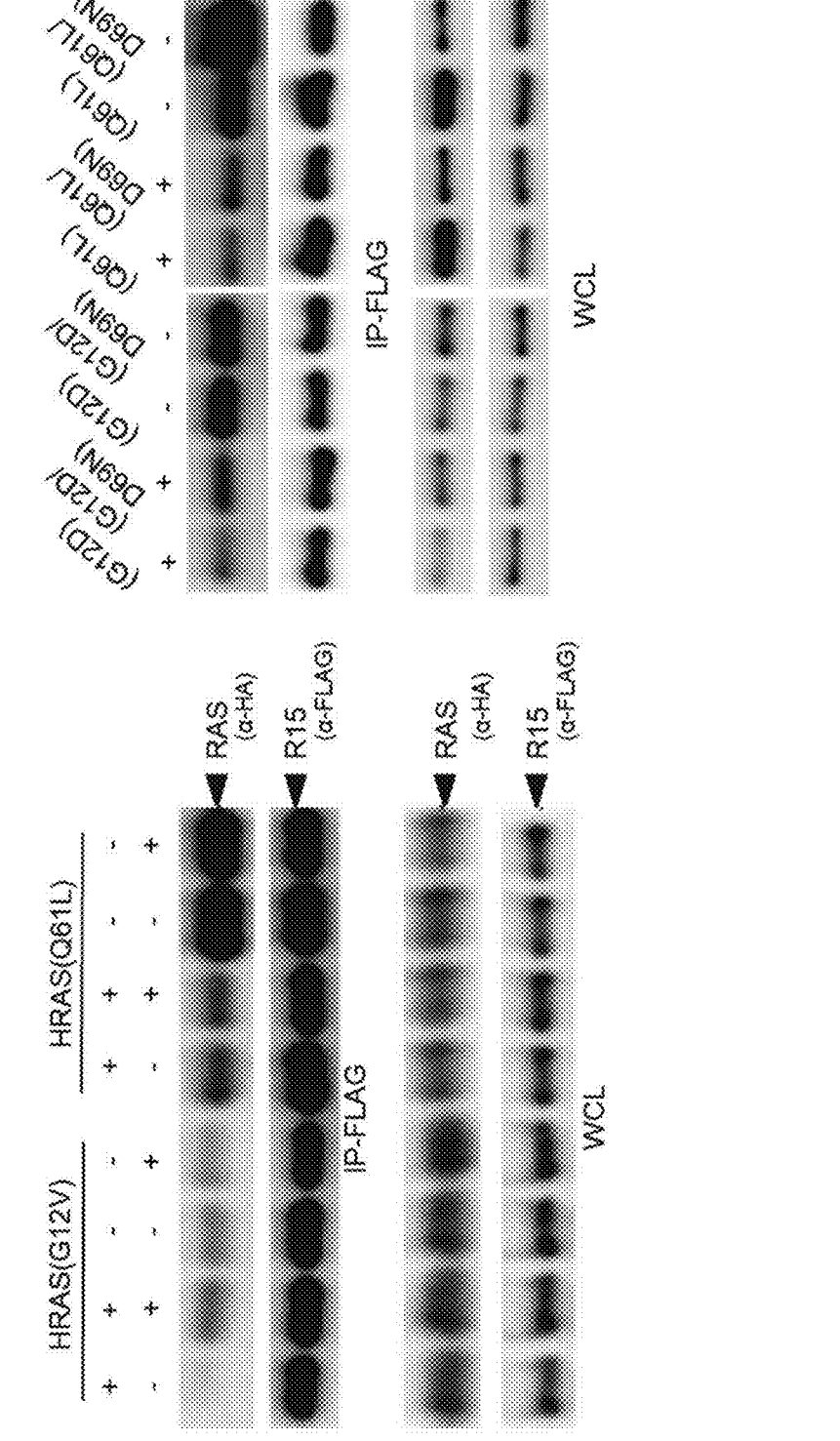
Figure 14A-B

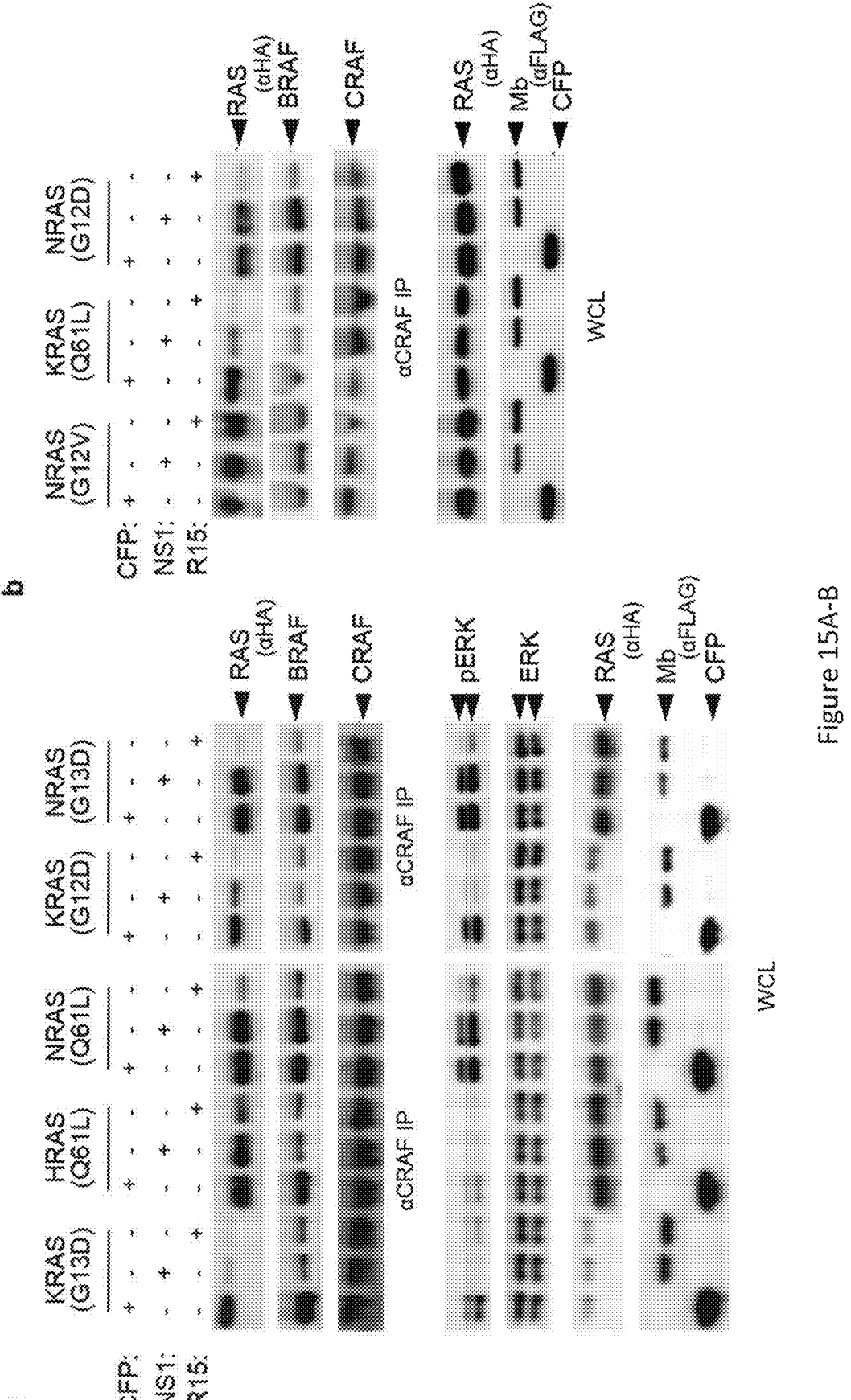
Figure 15A-B

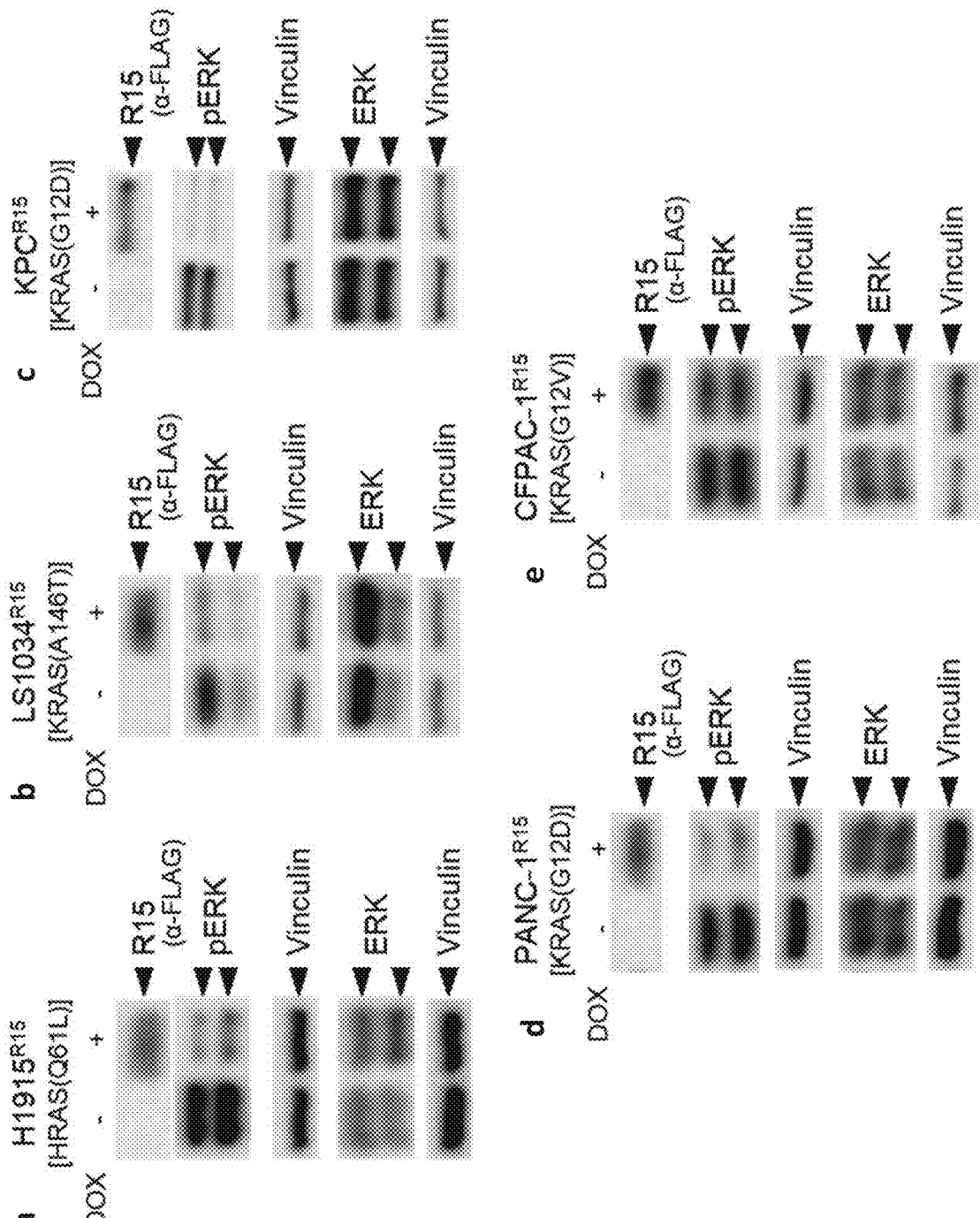
Figure 16A-E

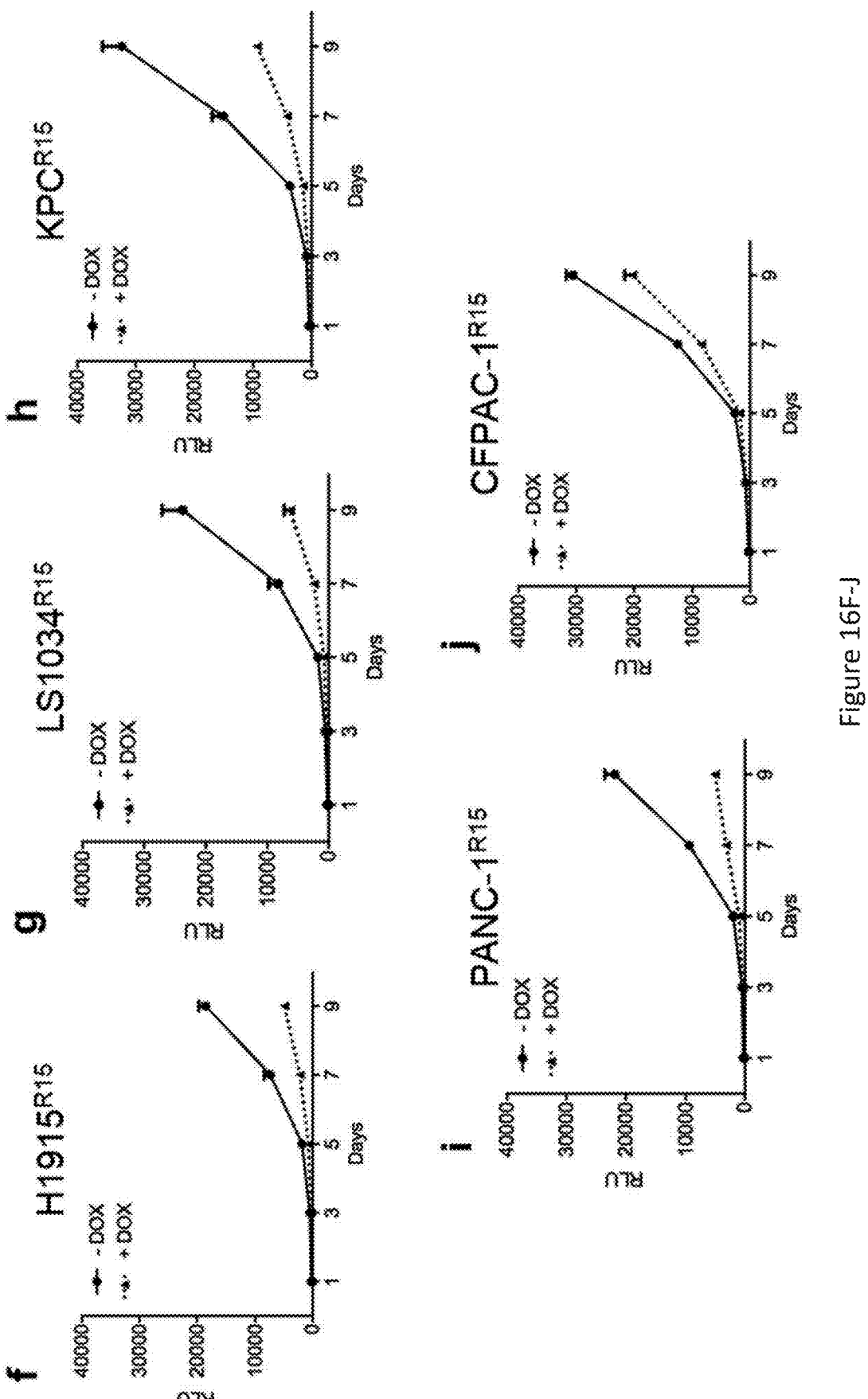
Figure 16F-J

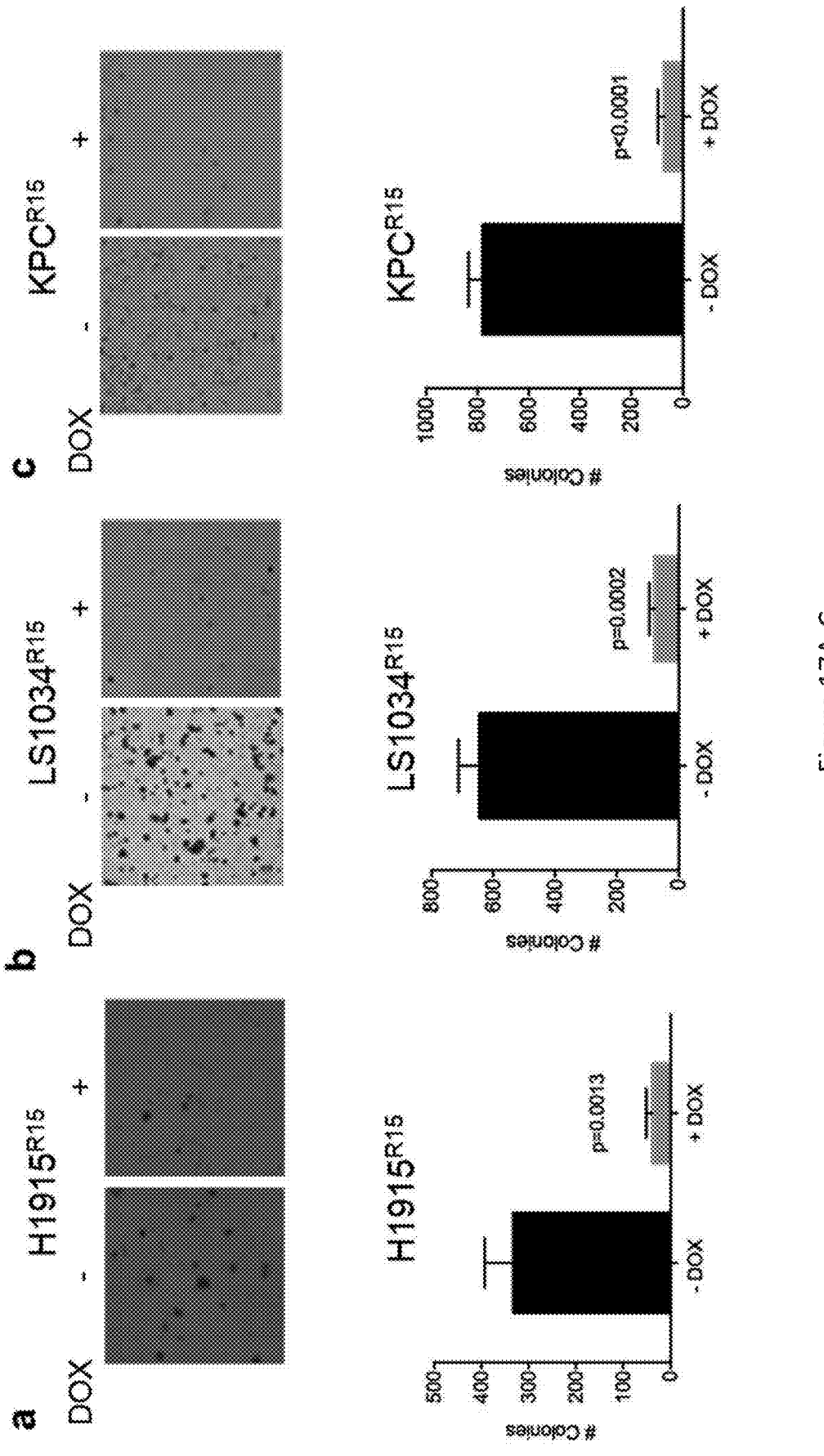
Figure 17A-C

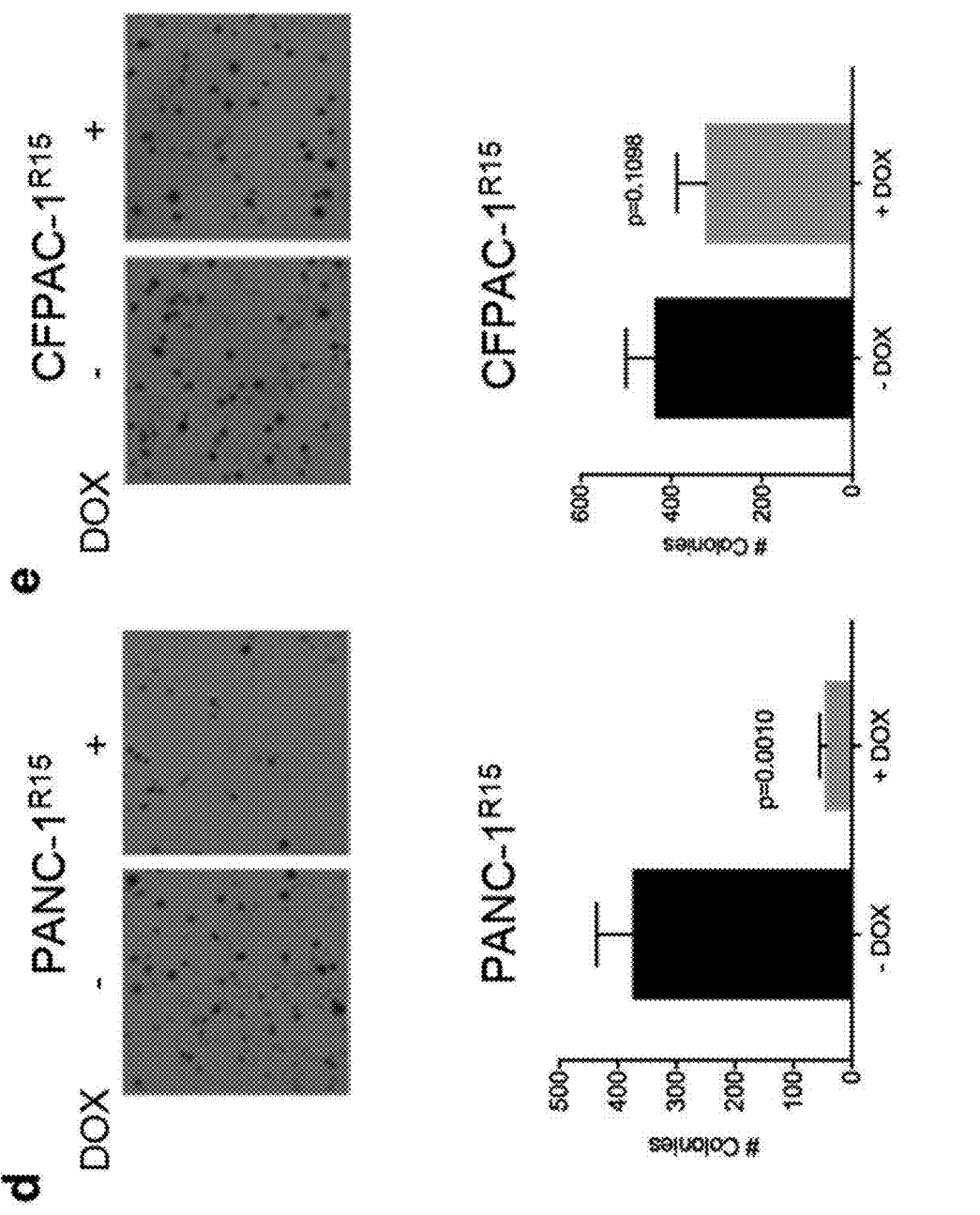
Figure 17D-E

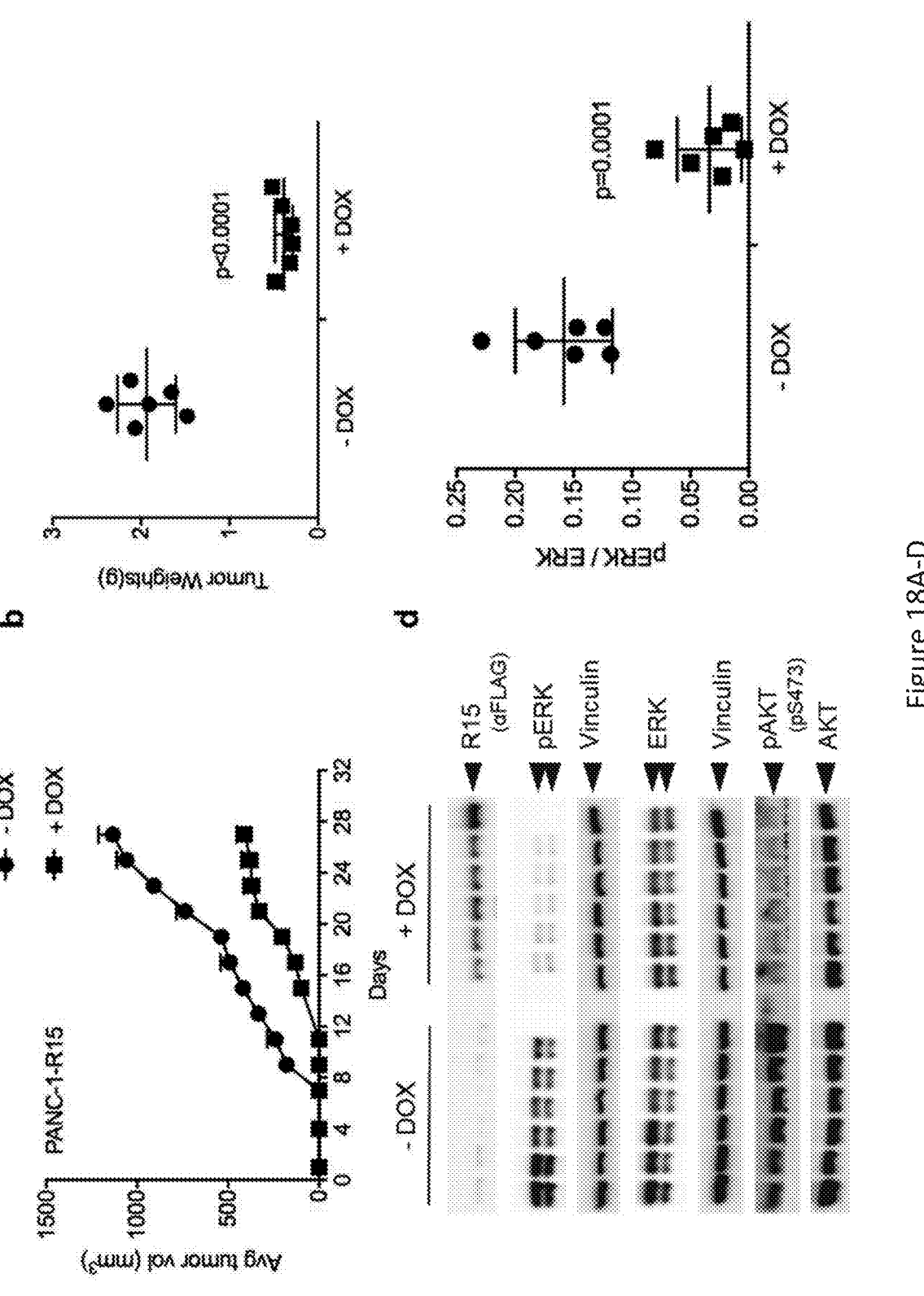
Figure 18A-D

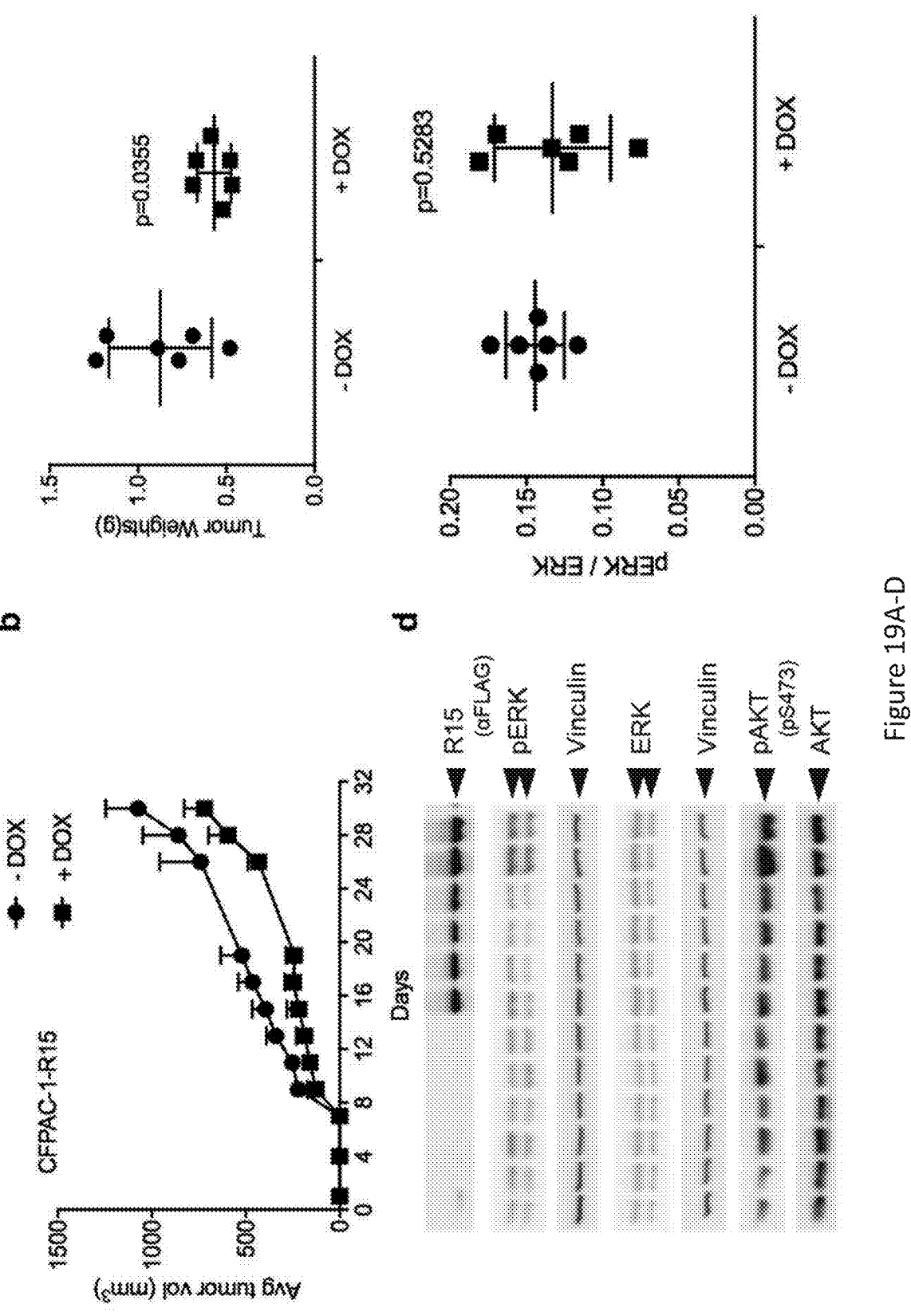
Figure 19A-D

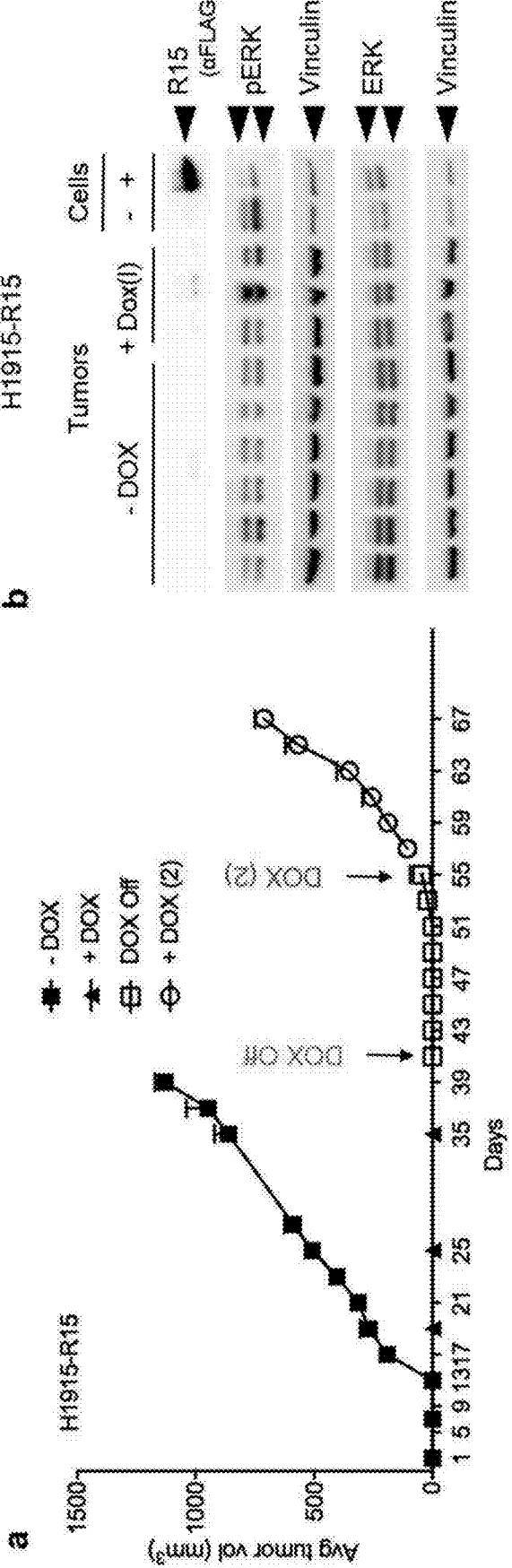
Figure 20A-B

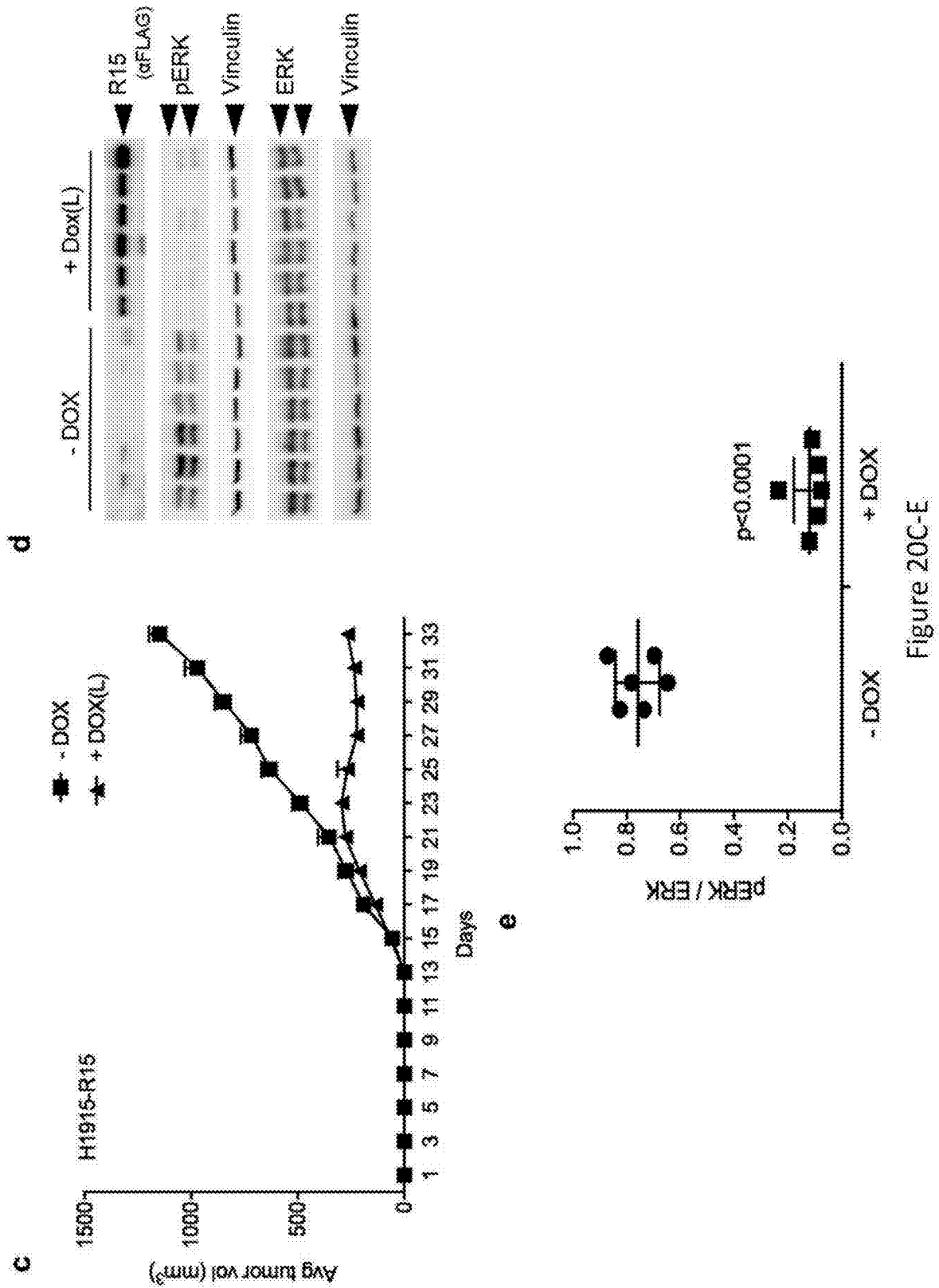
Figure 20C-E

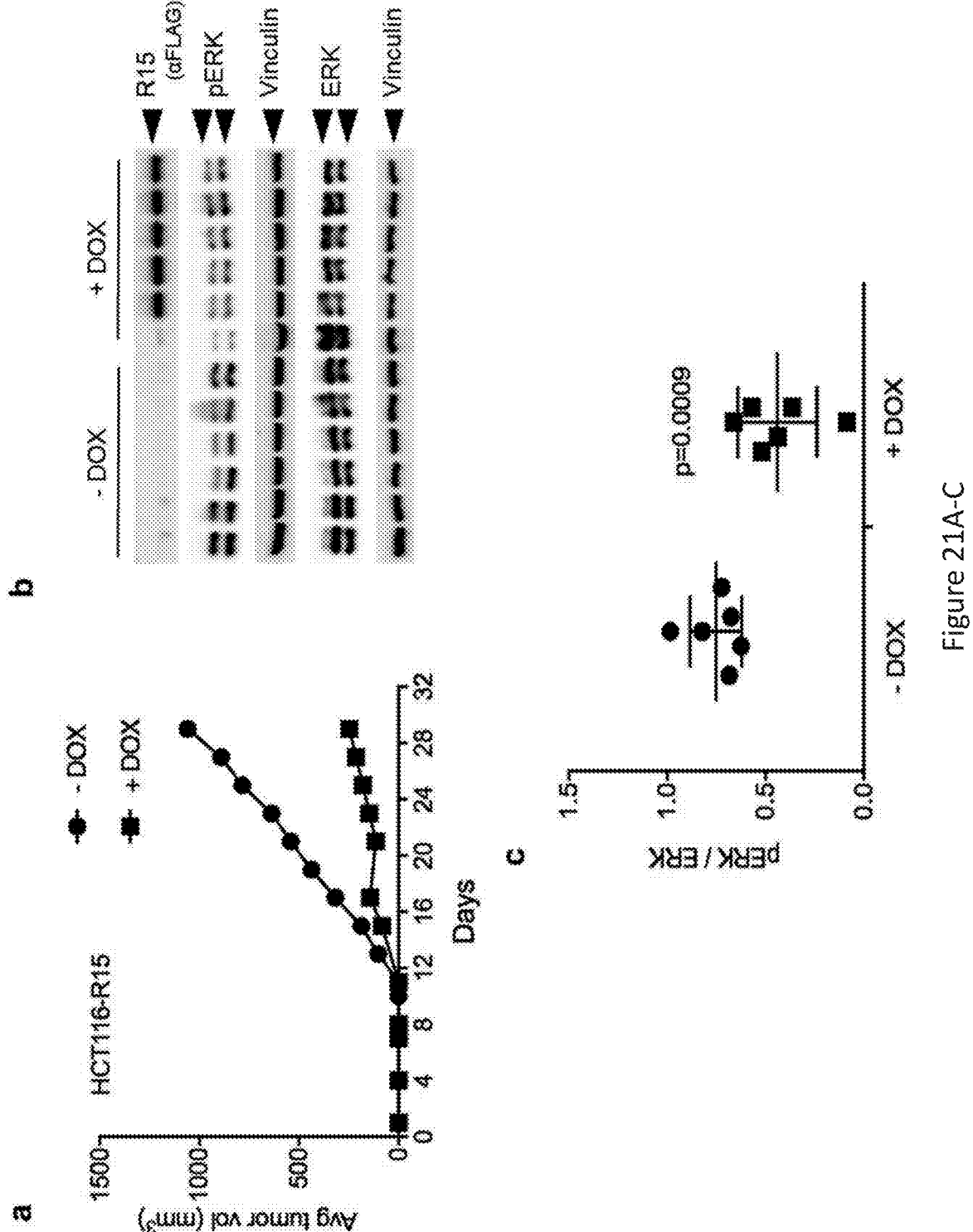
Figure 21A-C

SEQUENCE LISTING

<160> NUMBER OF SEQ ID NOS: 32

<210> SEQ ID NO 1
<211> LENGTH: 92
<212> TYPE: PRT
<213> ORGANISM: Artificial Sequence
<220> FEATURE:
<223> OTHER INFORMATION: R15m1

<400> SEQUENCE: 1

Val Ser Ser Val Pro Thr Lys Leu Glu Val Val Ala Ala Thr Pro Thr
1               5                   10                  15

Ser Leu Leu Ile Ser Trp Asp Ala Ser Ser Ser Val Ser Tyr Tyr
            20                  25                  30

Arg Ile Thr Tyr Gly Glu Thr Gly Gly Asn Pro Pro Val Gln Glu Phe
            35                  40                  45

Thr Val Pro Gly Tyr Tyr Ser Thr Ala Thr Ile Ser Gly Leu Lys Pro
        50                  55                  60

Gly Val Asp Tyr Thr Ile Thr Val Tyr Ala Val Trp Gln Gly Val Trp
65                  70                  75                  80

Arg Tyr Val Ser Pro Ile Ser Ile Asn Tyr Arg Thr
                85                  90

<210> SEQ ID NO 2
<211> LENGTH: 92
<212> TYPE: PRT
<213> ORGANISM: Artificial Sequence
<220> FEATURE:
<223> OTHER INFORMATION: R15m6

<400> SEQUENCE: 2

Val Ser Ser Val Pro Thr Lys Leu Glu Val Val Ala Ala Thr Pro Thr
1               5                   10                  15

Ser Leu Leu Ile Ser Trp Asp Ala Ser Ser Ser Ser Val Ser Tyr Tyr
            20                  25                  30

Arg Ile Thr Tyr Gly Glu Thr Gly Gly Asn Ser Pro Val Gln Glu Phe
            35                  40                  45

Thr Val Pro Gly Tyr Tyr Pro Thr Ala Thr Ile Ser Gly Leu Lys Pro
        50                  55                  60

Gly Val Asp Tyr Thr Ile Thr Val Tyr Ala Val Trp Gln Gly Val Trp
65                  70                  75                  80

Arg Tyr Val Ser Pro Ile Ser Ile Asn Tyr Arg Thr
                85                  90

<210> SEQ ID NO 3
<211> LENGTH: 92
<212> TYPE: PRT
<213> ORGANISM: Artificial Sequence
<220> FEATURE:
<223> OTHER INFORMATION: R15m9

<400> SEQUENCE: 3

Val Ser Ser Val Pro Thr Lys Leu Glu Val Val Ala Ala Thr Pro Thr
1               5                   10                  15

Ser Leu Leu Ile Ser Trp Asp Ala Ser Ser Ser Ser Val Ser Tyr Tyr
            20                  25                  30

Arg Ile Thr Tyr Gly Glu Thr Gly Gly Asn Ser Pro Val Gln Glu Phe
            35                  40                  45

Thr Val Pro Gly Tyr Tyr Ser Thr Ala Thr Ile Ser Gly Leu Lys Pro
        50                  55                  60

```
Gly Val Asp Tyr Thr Ile Thr Val Tyr Ala Val Trp Phe Gly His Trp
65                  70              75              80

Leu Tyr Val Ser Pro Ile Ser Ile Asn Tyr Arg Thr
                85              90

<210> SEQ ID NO 4
<211> LENGTH: 92
<212> TYPE: PRT
<213> ORGANISM: Artificial Sequence
<220> FEATURE:
<223> OTHER INFORMATION: R15m10

<400> SEQUENCE: 4

Val Ser Ser Val Pro Thr Lys Leu Glu Val Val Ala Ala Thr Pro Thr
1               5               10              15

Ser Leu Leu Ile Ser Trp Asp Ala Ser Ser Ser Val Ser Tyr Tyr
                20              25              30

Arg Ile Thr Tyr Gly Glu Thr Gly Gly Asn Ser Pro Val Gln Glu Phe
            35              40              45

Thr Val Pro Gly Tyr Tyr Ser Thr Ala Thr Ile Ser Gly Leu Lys Pro
        50              55              60

Gly Val Asp Tyr Thr Ile Thr Val Tyr Ala Val Trp Gln Gly Val Trp
65                  70              75              80

Arg Tyr Val Ser Pro Ile Ser Ile Asn Tyr Arg Thr
                85              90

<210> SEQ ID NO 5
<211> LENGTH: 92
<212> TYPE: PRT
<213> ORGANISM: Artificial Sequence
<220> FEATURE:
<223> OTHER INFORMATION: R15m11

<400> SEQUENCE: 5

Val Ser Ser Val Pro Thr Lys Leu Glu Val Val Ala Ala Thr Pro Thr
1               5               10              15

Ser Leu Leu Ile Ser Trp Asp Ala Ser Ser Ser Val Ser Tyr Tyr
                20              25              30

Arg Ile Thr Tyr Gly Glu Thr Gly Gly Ser Ser Pro Val Gln Glu Phe
            35              40              45

Thr Val Pro Gly Tyr Tyr Ser Thr Ala Thr Ile Ser Gly Leu Lys Pro
        50              55              60

Gly Val Asp Tyr Thr Ile Thr Val Tyr Ala Thr Trp Val Gly Val Trp
65                  70              75              80

Val Tyr Val Ser Pro Ile Ser Ile Asn Tyr Arg Thr
                85              90

<210> SEQ ID NO 6
<211> LENGTH: 92
<212> TYPE: PRT
<213> ORGANISM: Artificial Sequence
<220> FEATURE:
<223> OTHER INFORMATION: R15m27

<400> SEQUENCE: 6

Val Ser Ser Val Pro Thr Lys Leu Glu Val Val Ala Ala Thr Pro Thr
1               5               10              15

Ser Leu Leu Ile Ser Leu Asp Ala Ser Ser Ser Val Ser Tyr Tyr
                20              25              30
```

```
Arg Ile Thr Tyr Gly Glu Thr Gly Gly Asn Ser Pro Val Gln Glu Phe
        35                  40                  45

Thr Val Pro Gly Tyr Tyr Ser Thr Ala Thr Ile Ser Gly Leu Lys Pro
        50                  55                  60

Gly Val Asp Tyr Thr Ile Thr Val Tyr Ala Phe Arg Arg Lys Lys Trp
65                  70                  75                  80

Ser Tyr Ile Ser Pro Ile Ser Ile Asn Tyr Arg Thr
                85                  90
```

<210> SEQ ID NO 7
<211> LENGTH: 92
<212> TYPE: PRT
<213> ORGANISM: Artificial Sequence
<220> FEATURE:
<223> OTHER INFORMATION: R15m2

<400> SEQUENCE: 7

```
Val Ser Ser Val Pro Thr Lys Leu Glu Val Val Ala Ala Thr Pro Thr
1               5                   10                  15

Ser Leu Leu Ile Ser Trp Asp Ala Ser Ser Ser Ser Val Ser Tyr Tyr
            20                  25                  30

Arg Ile Thr Tyr Gly Glu Thr Gly Gly Asn Ser Pro Val Gln Glu Phe
        35                  40                  45

Thr Val Pro Gly Tyr Tyr Ser Thr Ala Thr Ile Ser Gly Leu Lys Pro
        50                  55                  60

Gly Val Asp Tyr Thr Ile Thr Val Tyr Ala Thr Trp Val Gly Val Trp
65                  70                  75                  80

Val Tyr Val Ser Pro Ile Ser Ile Asn Tyr Arg Thr
                85                  90
```

<210> SEQ ID NO 8
<211> LENGTH: 96
<212> TYPE: PRT
<213> ORGANISM: Artificial Sequence
<220> FEATURE:
<223> OTHER INFORMATION: R15mm2

<400> SEQUENCE: 8

```
Val Ser Ser Val Pro Thr Lys Leu Glu Val Val Ala Ala Thr Pro Thr
1               5                   10                  15

Ser Leu Leu Ile Ser Trp Asp Ala Ser Ser Ser Ser Val Ser Tyr Tyr
            20                  25                  30

Arg Ile Thr Tyr Gly Glu Thr Gly Gly Asn Ser Pro Val Gln Glu Phe
        35                  40                  45

Thr Val Pro Gly Tyr Tyr Ser Thr Ala Thr Ile Ser Gly Leu Lys Pro
        50                  55                  60

Gly Val Asp Tyr Thr Ile Thr Val Tyr Ala Val Trp Phe Lys Lys Trp
65                  70                  75                  80

Leu Tyr Val Ser Pro Ile Ser Ile Asn Tyr Arg Thr Glu Ile Asp Lys
                85                  90                  95
```

<210> SEQ ID NO 9
<211> LENGTH: 96
<212> TYPE: PRT
<213> ORGANISM: Artificial Sequence
<220> FEATURE:
<223> OTHER INFORMATION: R15mm4

-continued

```
<400> SEQUENCE: 9

Val Ser Ser Val Pro Thr Lys Leu Glu Val Val Ala Ala Thr Pro Thr
1               5                   10                  15

Ser Leu Leu Ile Ser Trp Asp Ala Ser Ser Ser Ser Val Ser Tyr Tyr
                20                  25                  30

Arg Ile Thr Tyr Gly Glu Thr Gly Gly Asn Ser Pro Val Gln Glu Phe
            35                  40                  45

Thr Val Pro Gly Tyr Tyr Ser Thr Ala Thr Ile Ser Gly Leu Lys Pro
        50                  55                  60

Gly Val Asp Tyr Thr Ile Thr Val Tyr Ala Val Trp Phe Gly Lys Trp
65                  70                  75                  80

Leu Tyr Val Ser Pro Ile Ser Ile Asn Tyr Arg Thr Glu Ile Asp Lys
                85                  90                  95

<210> SEQ ID NO 10
<211> LENGTH: 96
<212> TYPE: PRT
<213> ORGANISM: Artificial Sequence
<220> FEATURE:
<223> OTHER INFORMATION: R15mm7

<400> SEQUENCE: 10

Val Ser Ser Val Pro Thr Lys Leu Glu Val Val Ala Ala Thr Pro Thr
1               5                   10                  15

Ser Leu Leu Ile Ser Trp Asp Ala Ser Ser Ser Ser Val Ser Tyr Tyr
                20                  25                  30

Arg Ile Thr Tyr Gly Glu Thr Gly Gly Asn Ser Pro Val Gln Glu Phe
            35                  40                  45

Thr Val Pro Gly Tyr Tyr Ser Thr Ala Thr Ile Ser Gly Leu Lys Pro
        50                  55                  60

Gly Val Asp Tyr Thr Ile Thr Val Tyr Ala Val Ser Phe Gly His Trp
65                  70                  75                  80

Leu Tyr Val Ser Pro Ile Ser Ile Asn Tyr Arg Thr Glu Ile Asp Lys
                85                  90                  95

<210> SEQ ID NO 11
<211> LENGTH: 96
<212> TYPE: PRT
<213> ORGANISM: Artificial Sequence
<220> FEATURE:
<223> OTHER INFORMATION: R15mm8

<400> SEQUENCE: 11

Val Ser Ser Val Pro Thr Lys Leu Glu Val Val Ala Ala Thr Pro Thr
1               5                   10                  15

Ser Leu Leu Ile Ser Trp Asp Ala Ser Ser Ser Ser Val Ser Tyr Tyr
                20                  25                  30

Arg Ile Thr Tyr Gly Glu Thr Gly Gly Asn Ser Pro Val Gln Glu Phe
            35                  40                  45

Thr Val Pro Gly Tyr Tyr Ser Thr Ala Thr Ile Ser Gly Leu Lys Pro
        50                  55                  60

Gly Val Asp Tyr Thr Ile Thr Val Tyr Ala Val Trp Ser Gly His Trp
65                  70                  75                  80

Leu Tyr Val Ser Pro Ile Ser Ile Asn Tyr Arg Thr Glu Ile Asp Lys
                85                  90                  95

<210> SEQ ID NO 12
```

<211> LENGTH: 96
<212> TYPE: PRT
<213> ORGANISM: Artificial Sequence
<220> FEATURE:
<223> OTHER INFORMATION: R15mm9

<400> SEQUENCE: 12

```
Val Ser Ser Val Pro Thr Lys Leu Glu Val Val Ala Ala Thr Pro Thr
1               5                   10                  15

Ser Leu Leu Ile Ser Trp Asp Ala Ser Ser Ser Val Ser Tyr Tyr
                20                  25                  30

Arg Ile Thr Tyr Gly Glu Thr Gly Gly Asn Ser Pro Val Gln Glu Phe
            35                  40                  45

Thr Val Pro Gly Tyr Tyr Ser Thr Ala Thr Ile Ser Gly Leu Lys Pro
        50                  55                  60

Gly Val Asp Tyr Thr Ile Thr Val Tyr Ala Val Trp Phe Gly Ser Trp
65                  70                  75                  80

Leu Tyr Val Ser Pro Ile Ser Ile Asn Tyr Arg Thr Glu Ile Asp Lys
                85                  90                  95
```

<210> SEQ ID NO 13
<211> LENGTH: 96
<212> TYPE: PRT
<213> ORGANISM: Artificial Sequence
<220> FEATURE:
<223> OTHER INFORMATION: R15mm11

<400> SEQUENCE: 13

```
Val Ser Ser Val Pro Thr Lys Leu Glu Val Val Ala Ala Thr Pro Thr
1               5                   10                  15

Ser Leu Leu Ile Ser Trp Asp Ala Ser Ser Ser Val Ser Tyr Tyr
                20                  25                  30

Arg Ile Thr Tyr Gly Glu Thr Gly Gly Asn Ser Pro Val Gln Glu Phe
            35                  40                  45

Thr Val Pro Gly Tyr Tyr Ser Thr Ala Thr Ile Ser Gly Leu Lys Pro
        50                  55                  60

Gly Val Asp Tyr Thr Ile Thr Val Tyr Ala Val Trp Phe Gly His Trp
65                  70                  75                  80

Ser Tyr Val Ser Pro Ile Ser Ile Asn Tyr Arg Thr Glu Ile Asp Lys
                85                  90                  95
```

<210> SEQ ID NO 14
<211> LENGTH: 96
<212> TYPE: PRT
<213> ORGANISM: Artificial Sequence
<220> FEATURE:
<223> OTHER INFORMATION: R15mm13

<400> SEQUENCE: 14

```
Val Ser Ser Val Pro Thr Lys Leu Glu Val Val Ala Ala Thr Pro Thr
1               5                   10                  15

Ser Leu Leu Ile Ser Trp Asp Ala Ser Ser Ser Val Ser Tyr Tyr
                20                  25                  30

Arg Ile Thr Tyr Gly Glu Thr Gly Gly Asn Ser Pro Val Gln Glu Phe
            35                  40                  45

Thr Val Pro Gly Tyr Tyr Ser Thr Ala Thr Ile Ser Gly Leu Lys Pro
        50                  55                  60

Gly Val Asp Tyr Thr Ile Thr Val Tyr Ala Val Trp Phe Gly His Trp
65                  70                  75                  80
```

-continued

```
Leu Tyr Ser Ser Pro Ile Ser Ile Asn Tyr Arg Thr Glu Ile Asp Lys
                85              90              95

<210> SEQ ID NO 15
<211> LENGTH: 92
<212> TYPE: PRT
<213> ORGANISM: Artificial Sequence
<220> FEATURE:
<223> OTHER INFORMATION: R15m9-8

<400> SEQUENCE: 15

Val Ser Ser Val Pro Thr Lys Leu Glu Val Val Ala Ala Thr Pro Thr
1               5                   10                  15

Ser Leu Leu Ile Ser Trp Asp Ala Ser Ser Ser Ser Val Ser Tyr Tyr
                20                  25                  30

Arg Ile Thr Tyr Gly Glu Thr Gly Gly Asn Ser Pro Val Gln Glu Phe
            35                  40                  45

Thr Val Pro Gly Tyr Tyr Ser Thr Ala Thr Ile Ser Gly Leu Lys Pro
        50                  55                  60

Gly Val Asp Tyr Thr Ile Thr Val Tyr Ala Val Trp Glu Gly Lys Trp
65                  70                  75                  80

Leu Tyr Val Ser Pro Ile Ser Ile Asn Tyr Arg Thr
                85                  90

<210> SEQ ID NO 16
<211> LENGTH: 92
<212> TYPE: PRT
<213> ORGANISM: Artificial Sequence
<220> FEATURE:
<223> OTHER INFORMATION: R15m9-17

<400> SEQUENCE: 16

Val Ser Ser Val Pro Thr Lys Leu Glu Val Val Ala Ala Thr Pro Thr
1               5                   10                  15

Ser Leu Leu Ile Ser Trp Asp Ala Ser Ser Ser Ser Val Ser Tyr Tyr
                20                  25                  30

Arg Ile Thr Tyr Gly Glu Thr Gly Gly Asn Ser Pro Val Gln Glu Phe
            35                  40                  45

Thr Val Pro Gly Tyr Tyr Ser Thr Ala Thr Ile Ser Gly Leu Lys Pro
        50                  55                  60

Gly Val Asp Tyr Thr Ile Thr Val Tyr Ala Ile Ser Ala Gly Tyr Trp
65                  70                  75                  80

Leu Tyr Val Ser Pro Ile Ser Ile Asn Tyr Arg Thr
                85                  90

<210> SEQ ID NO 17
<211> LENGTH: 92
<212> TYPE: PRT
<213> ORGANISM: Artificial Sequence
<220> FEATURE:
<223> OTHER INFORMATION: R15m9-19

<400> SEQUENCE: 17

Val Ser Ser Val Pro Thr Lys Leu Glu Val Val Ala Ala Thr Pro Thr
1               5                   10                  15

Ser Leu Leu Ile Ser Trp Asp Ala Ser Ser Ser Ser Val Ser Tyr Tyr
                20                  25                  30

Arg Ile Thr Tyr Gly Glu Thr Gly Gly Asn Ser Pro Val Gln Glu Phe
            35                  40                  45
```

-continued

```
Thr Val Pro Gly Tyr Tyr Ser Thr Ala Thr Ile Ser Gly Leu Lys Pro
    50                  55                  60

Gly Val Asp Tyr Thr Ile Thr Val Tyr Ala Val Ser Ser Gly Tyr Trp
65                  70                  75                  80

Leu Tyr Val Ser Pro Ile Ser Ile Asn Tyr Arg Thr
                85                  90
```

```
<210> SEQ ID NO 18
<211> LENGTH: 92
<212> TYPE: PRT
<213> ORGANISM: Artificial Sequence
<220> FEATURE:
<223> OTHER INFORMATION: R15m9-30

<400> SEQUENCE: 18
```

```
Val Ser Ser Val Pro Thr Lys Leu Glu Val Val Ala Ala Thr Pro Thr
1               5                   10                  15

Ser Leu Leu Ile Ser Trp Asp Ala Ser Ser Ser Val Ser Tyr Tyr
                20                  25                  30

Arg Ile Thr Tyr Gly Glu Thr Gly Gly Asn Ser Pro Val Gln Glu Phe
        35                  40                  45

Thr Val Pro Gly Tyr Tyr Ser Thr Ala Thr Ile Ser Gly Leu Lys Pro
    50                  55                  60

Gly Val Asp Tyr Thr Ile Thr Val Tyr Ala Ile Trp Ser Gly His Trp
65                  70                  75                  80

Leu Tyr Val Ser Pro Ile Ser Ile Asn Tyr Arg Thr
                85                  90
```

```
<210> SEQ ID NO 19
<211> LENGTH: 92
<212> TYPE: PRT
<213> ORGANISM: Artificial Sequence
<220> FEATURE:
<223> OTHER INFORMATION: R15m9-38

<400> SEQUENCE: 19
```

```
Val Ser Ser Val Pro Thr Lys Leu Glu Val Val Ala Ala Thr Pro Thr
1               5                   10                  15

Ser Leu Leu Ile Ser Trp Asp Ala Ser Ser Ser Val Ser Tyr Tyr
                20                  25                  30

Arg Ile Thr Tyr Gly Glu Thr Gly Gly Asn Ser Pro Val Gln Glu Phe
        35                  40                  45

Thr Val Pro Gly Tyr Tyr Ser Thr Ala Thr Ile Ser Gly Leu Lys Pro
    50                  55                  60

Gly Val Asp Tyr Thr Ile Thr Val Tyr Ala Ser Trp Glu Gly Arg Trp
65                  70                  75                  80

Leu Tyr Val Ser Pro Ile Ser Ile Asn Tyr Arg Thr
                85                  90
```

```
<210> SEQ ID NO 20
<211> LENGTH: 92
<212> TYPE: PRT
<213> ORGANISM: Artificial Sequence
<220> FEATURE:
<223> OTHER INFORMATION: R15m9-49

<400> SEQUENCE: 20
```

```
Val Ser Ser Val Pro Thr Lys Leu Glu Val Val Ala Ala Thr Pro Thr
1               5                   10                  15
```

```
Ser Leu Leu Ile Ser Trp Asp Ala Ser Ser Ser Ser Val Ser Tyr Tyr
        20              25              30

Arg Ile Thr Tyr Gly Glu Thr Gly Gly Asn Ser Pro Val Gln Glu Phe
        35              40              45

Thr Val Pro Gly Tyr Tyr Ser Thr Ala Thr Ile Ser Gly Leu Lys Pro
    50              55              60

Gly Val Asp Tyr Thr Ile Thr Val Tyr Ala Ser Trp Glu Gly Lys Trp
65              70              75              80

Leu Tyr Val Ser Pro Ile Ser Ile Asn Tyr Arg Thr
                85              90
```

<210> SEQ ID NO 21
<211> LENGTH: 92
<212> TYPE: PRT
<213> ORGANISM: Artificial Sequence
<220> FEATURE:
<223> OTHER INFORMATION: R15m9-8-DE-3

<400> SEQUENCE: 21

```
Val Ser Ser Val Pro Thr Lys Leu Glu Val Val Ala Ala Thr Pro Thr
1               5               10              15

Ser Leu Leu Ile Ser Trp Asp Ala Ser Ser Ser Ser Val Ser Tyr Tyr
        20              25              30

Arg Ile Thr Tyr Gly Glu Thr Gly Gly Asn Ser Pro Val Gln Glu Phe
        35              40              45

Thr Val Pro Gly Tyr Tyr Asp Thr Ala Thr Ile Ser Gly Leu Lys Pro
    50              55              60

Gly Val Asp Tyr Thr Ile Thr Val Tyr Ala Val Trp Glu Gly Lys Trp
65              70              75              80

Leu Tyr Val Ser Pro Ile Ser Ile Asn Tyr Arg Thr
                85              90
```

<210> SEQ ID NO 22
<211> LENGTH: 92
<212> TYPE: PRT
<213> ORGANISM: Artificial Sequence
<220> FEATURE:
<223> OTHER INFORMATION: R15m9-8-DE-9

<400> SEQUENCE: 22

```
Val Ser Ser Val Pro Thr Lys Leu Glu Val Val Ala Ala Thr Pro Thr
1               5               10              15

Ser Leu Leu Ile Ser Trp Asp Ala Ser Ser Ser Ser Val Ser Tyr Tyr
        20              25              30

Arg Ile Thr Tyr Gly Glu Thr Gly Gly Asn Ser Pro Val Gln Glu Phe
        35              40              45

Thr Val Pro Gly Ser Asp His Thr Ala Thr Ile Ser Gly Leu Lys Pro
    50              55              60

Gly Val Asp Tyr Thr Ile Thr Val Tyr Ala Val Trp Glu Gly Lys Trp
65              70              75              80

Leu Tyr Val Ser Pro Ile Ser Ile Asn Tyr Arg Thr
                85              90
```

<210> SEQ ID NO 23
<211> LENGTH: 92
<212> TYPE: PRT
<213> ORGANISM: Artificial Sequence
<220> FEATURE:
<223> OTHER INFORMATION: R15m9-8-DE-12

<400> SEQUENCE: 23

```
Val Ser Ser Val Pro Thr Lys Leu Glu Val Val Ala Ala Thr Pro Thr
1               5                   10                  15

Ser Leu Leu Ile Ser Trp Asp Ala Ser Ser Ser Ser Val Ser Tyr Tyr
                20                  25                  30

Arg Ile Thr Tyr Gly Glu Thr Gly Gly Asn Ser Pro Val Gln Glu Phe
            35                  40                  45

Thr Val Pro Gly Tyr Ser His Thr Ala Thr Ile Ser Gly Leu Lys Pro
        50                  55                  60

Gly Val Asp Tyr Thr Ile Thr Val Tyr Ala Val Trp Glu Gly Lys Trp
65                  70                  75                  80

Leu Tyr Val Ser Pro Ile Ser Ile Asn Tyr Arg Thr
                85                  90
```

<210> SEQ ID NO 24
<211> LENGTH: 92
<212> TYPE: PRT
<213> ORGANISM: Artificial Sequence
<220> FEATURE:
<223> OTHER INFORMATION: R15m9-8-DE-15

<400> SEQUENCE: 24

```
Val Ser Ser Val Pro Thr Lys Leu Glu Val Val Ala Ala Thr Pro Thr
1               5                   10                  15

Ser Leu Leu Ile Ser Trp Asp Ala Ser Ser Ser Ser Val Ser Tyr Tyr
                20                  25                  30

Arg Ile Thr Tyr Gly Glu Thr Gly Gly Asn Ser Pro Val Gln Glu Phe
            35                  40                  45

Thr Val Pro Gly Asp Tyr Ala Thr Ala Thr Ile Ser Gly Leu Lys Pro
        50                  55                  60

Gly Val Asp Tyr Thr Ile Thr Val Tyr Ala Val Trp Glu Gly Lys Trp
65                  70                  75                  80

Leu Tyr Val Ser Pro Ile Ser Ile Asn Tyr Arg Thr
                85                  90
```

<210> SEQ ID NO 25
<211> LENGTH: 92
<212> TYPE: PRT
<213> ORGANISM: Artificial Sequence
<220> FEATURE:
<223> OTHER INFORMATION: R15m9-8-DE-16

<400> SEQUENCE: 25

```
Val Ser Ser Val Pro Thr Lys Leu Glu Val Val Ala Ala Thr Pro Thr
1               5                   10                  15

Ser Leu Leu Ile Ser Trp Asp Ala Ser Ser Ser Ser Val Ser Tyr Tyr
                20                  25                  30

Arg Ile Thr Tyr Gly Glu Thr Gly Gly Asn Ser Pro Val Gln Glu Phe
            35                  40                  45

Thr Val Pro Gly Ala Ala Ala Thr Ala Thr Ile Ser Gly Leu Lys Pro
        50                  55                  60

Gly Val Asp Tyr Thr Ile Thr Val Tyr Ala Val Trp Glu Gly Lys Trp
65                  70                  75                  80

Leu Tyr Val Ser Pro Ile Ser Ile Asn Tyr Arg Thr
                85                  90
```

<210> SEQ ID NO 26
<211> LENGTH: 92

```
<212> TYPE: PRT
<213> ORGANISM: Artificial Sequence
<220> FEATURE:
<223> OTHER INFORMATION: R15m9-8-DE-19

<400> SEQUENCE: 26

Val Ser Ser Val Pro Thr Lys Leu Glu Val Val Ala Ala Thr Pro Thr
1               5                   10                  15

Ser Leu Leu Ile Ser Trp Asp Ala Ser Ser Ser Ser Val Ser Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Ala Ser Thr Ala Thr Ile Ser Gly Leu Lys Pro
    50                  55                  60

Gly Val Asp Tyr Thr Ile Thr Val Tyr Ala Val Trp Glu Gly Lys Trp
65                  70                  75                  80

Leu Tyr Val Ser Pro Ile Ser Ile Asn Tyr Arg Thr
                85                  90

<210> SEQ ID NO 27
<211> LENGTH: 92
<212> TYPE: PRT
<213> ORGANISM: Artificial Sequence
<220> FEATURE:
<223> OTHER INFORMATION: R15m9-8-FG7-8

<400> SEQUENCE: 27

Val Ser Ser Val Pro Thr Lys Leu Glu Val Val Ala Ala Thr Pro Thr
1               5                   10                  15

Ser Leu Leu Ile Ser Trp Asp Ala Ser Ser Ser Ser Val Ser Tyr Tyr
            20                  25                  30

Arg Ile Thr Tyr Gly Glu Thr Gly Gly Asn Ser Pro Val Gln Glu Phe
        35                  40                  45

Thr Val Pro Gly Tyr Ser His Thr Ala Thr Ile Ser Gly Leu Lys Pro
    50                  55                  60

Gly Val Asp Tyr Thr Ile Thr Val Tyr Ala Val Trp Glu Gly Lys Trp
65                  70                  75                  80

Val Tyr Val Ser Pro Ile Ser Ile Asn Tyr Arg Thr
                85                  90

<210> SEQ ID NO 28
<211> LENGTH: 92
<212> TYPE: PRT
<213> ORGANISM: Artificial Sequence
<220> FEATURE:
<223> OTHER INFORMATION: R15m9-8-FG7-10

<400> SEQUENCE: 28

Val Ser Ser Val Pro Thr Lys Leu Glu Val Val Ala Ala Thr Pro Thr
1               5                   10                  15

Ser Leu Leu Ile Ser Trp Asp Ala Ser Ser Ser Ser Val Ser Tyr Tyr
            20                  25                  30

Arg Ile Thr Tyr Gly Glu Thr Gly Gly Asn Ser Pro Val Gln Glu Phe
        35                  40                  45

Thr Val Pro Gly Asp Tyr Ala Thr Ala Thr Ile Ser Gly Leu Lys Pro
    50                  55                  60

Gly Val Asp Tyr Thr Ile Thr Val Tyr Ala Val Trp Glu Gly Lys Trp
65                  70                  75                  80
```

-continued

```
Thr Tyr Val Ser Pro Ile Ser Ile Asn Tyr Arg Thr
                85                  90

<210> SEQ ID NO 29
<211> LENGTH: 92
<212> TYPE: PRT
<213> ORGANISM: Artificial Sequence
<220> FEATURE:
<223> OTHER INFORMATION: R15m9-8-FG7-16

<400> SEQUENCE: 29

Val Ser Ser Val Pro Thr Lys Leu Glu Val Val Ala Ala Thr Pro Thr
1               5                   10                  15

Ser Leu Leu Ile Ser Trp Asp Ala Ser Ser Ser Ser Val Ser Tyr Tyr
            20                  25                  30

Arg Ile Thr Tyr Gly Glu Thr Gly Gly Asn Ser Pro Val Gln Glu Phe
        35                  40                  45

Thr Val Pro Gly Tyr Ser His Thr Ala Thr Ile Ser Gly Leu Lys Pro
    50                  55                  60

Gly Val Asp Tyr Thr Ile Thr Val Tyr Ala Val Trp Glu Gly Lys Trp
65                  70                  75                  80

Lys Tyr Val Ser Pro Ile Ser Ile Asn Tyr Arg Thr
                85                  90

<210> SEQ ID NO 30
<211> LENGTH: 92
<212> TYPE: PRT
<213> ORGANISM: Artificial Sequence
<220> FEATURE:
<223> OTHER INFORMATION: R15m9-8-FG7-17

<400> SEQUENCE: 30

Val Ser Ser Val Pro Thr Lys Leu Glu Val Val Ala Ala Thr Pro Thr
1               5                   10                  15

Ser Leu Leu Ile Ser Trp Asp Ala Ser Ser Ser Ser Val Ser Tyr Tyr
            20                  25                  30

Arg Ile Thr Tyr Gly Glu Thr Gly Gly Asn Ser Pro Val Gln Glu Phe
        35                  40                  45

Thr Val Pro Gly Asp Tyr Ala Thr Ala Thr Ile Ser Gly Leu Lys Pro
    50                  55                  60

Gly Val Asp Tyr Thr Ile Thr Val Tyr Ala Val Trp Glu Gly Lys Trp
65                  70                  75                  80

Ala Tyr Val Ser Pro Ile Ser Ile Asn Tyr Arg Thr
                85                  90

<210> SEQ ID NO 31
<211> LENGTH: 92
<212> TYPE: PRT
<213> ORGANISM: Artificial Sequence
<220> FEATURE:
<223> OTHER INFORMATION: R15m9-8-FG7-34

<400> SEQUENCE: 31

Val Ser Ser Val Pro Thr Lys Leu Glu Val Val Ala Ala Thr Pro Thr
1               5                   10                  15

Ser Leu Leu Ile Ser Trp Asp Ala Ser Ser Ser Ser Val Ser Tyr Tyr
            20                  25                  30

Arg Ile Thr Tyr Gly Glu Thr Gly Gly Asn Ser Pro Val Gln Glu Phe
        35                  40                  45
```

```
Thr Val Pro Gly Tyr Ser His Thr Ala Thr Ile Ser Gly Leu Lys Pro
    50              55                  60

Gly Val Asp Tyr Thr Ile Thr Val Tyr Ala Val Trp Glu Gly Lys Trp
65              70                  75                  80

Arg Tyr Val Ser Pro Ile Ser Ile Asn Tyr Arg Thr
                85                  90

<210> SEQ ID NO 32
<211> LENGTH: 92
<212> TYPE: PRT
<213> ORGANISM: Artificial Sequence
<220> FEATURE:
<223> OTHER INFORMATION: R15m9-8-FG7-42

<400> SEQUENCE: 32

Val Ser Ser Val Pro Thr Lys Leu Glu Val Val Ala Ala Thr Pro Thr
1               5                   10                  15

Ser Leu Leu Ile Ser Trp Asp Ala Ser Ser Ser Ser Val Ser Tyr Tyr
                20                  25                  30

Arg Ile Thr Tyr Gly Glu Thr Gly Gly Asn Ser Pro Val Gln Glu Phe
            35                  40                  45

Thr Val Pro Gly Ser Asp His Thr Ala Thr Ile Ser Gly Leu Lys Pro
    50              55                  60

Gly Val Asp Tyr Thr Ile Thr Val Tyr Ala Val Trp Glu Gly Lys Trp
65              70                  75                  80

Val Tyr Val Ser Pro Ile Ser Ile Asn Tyr Arg Thr
                85                  90
```

COMPOSITIONS AND METHODS TARGETING THE NUCLEOTIDE FREE STATE OF RAS TO BLOCK ONCOGENIC SIGNALING AND TRANSFORMATION

CROSS-REFERENCE TO RELATED APPLICATIONS

This application is the U.S. national phase application filed under 35 U.S.C. § 371 claiming benefit to International Patent Application No. PCT/US2020/038363, filed on Jun. 18, 2020, which is entitled to priority to U.S. Provisional Patent Application No. 62/862,924, filed Jun. 18, 2019, the disclosure of which is incorporated herein by reference in its entirety.

STATEMENT REGARDING FEDERALLY SPONSORED RESEARCH OR DEVELOPMENT

This invention was made with Government support under Grant Nos. R21CA201717-0251, and RO1CA212608 awarded by the National Institutes of Health, and by 2101BX002095 awarded by the U.S. Department of Veteran Affairs. The Government has certain rights in this invention

REFERENCE TO A "SEQUENCE LISTING," A TABLE, OR A COMPUTER PROGRAM LISTING APPENDIX SUBMITTED AS AN ASCII TEXT FILE

The Sequence Listing written in the ASCII text file:
"206085-0071-00US SequenceListing.txt";
created on Dec. 2, 2021, and 29,156 bytes in size, is
hereby incorporated by reference.

BACKGROUND OF THE INVENTION

Nucleotide-free RAS has a role in regulating specific signaling proteins (Wong et al., 2012, PlosOne, PLoS One. 2012; 7(9): e45360). The ability to inhibit RAS signaling is clinically very important given that Ras proteins are essential components of signaling networks controlling cellular proliferation, differentiation, and survival. Further, oncogenic mutations of the H-ras, N-ras, or K-ras genes are frequently found in human tumors and are known to be oncogenic. Conventional wisdom in the field regarded nucleotide-free RAS as a highly transient state of the RAS protein. Monobodies are single-domain synthetic protein scaffolds that achieve affinity and selectivity similar to antibodies but are refractory to the reducing environment of cells and thus can be utilized as genetically encoded reagents (Koide et al., 2012, J Mol Biol, 415:393-405; Spencer-Smith et al., 2017, Nat Chem Biol, 13(1):62-8; Wojcik et al., 2010, Nat Struct Mol Biol, 17(4):519-27).

Accordingly, there exists a need for improved methods and compositions that that prevent RAS loading with GTP by binding nucleotide-free RAS, for the detection, diagnosis, prevention and treatment of diseases or disorders, including cancer. The present invention meets this need.

SUMMARY

In one embodiment, the invention relates to a composition comprising at least one molecule that specifically binds Ras in a nucleotide free state (apo RAS). In one embodiment, the apo RAS binding molecule is a chemical compound, a protein, a peptide, a peptidomemetic, an antibody, an antibody fragment, an antibody mimetic, a monobody, a fusion protein comprising a monobody domain, an aptamer, a ribozyme, a small molecule chemical compound, an short hairpin RNA, an antisense nucleic acid molecule, siRNA, miRNA, a nucleic acid encoding an antisense nucleic acid molecule, or a nucleic acid sequence encoding a protein.

In one embodiment, the molecule that specifically binds apo RAS a monobody or a fusion protein comprising a monobody domain. In one embodiment, the monobody or monobody domain comprises a peptide sequence of SEQ ID NO: 1-32, a variant thereof, or a fragment thereof. In one embodiment, the fusion protein comprising a monobody domain further comprises a therapeutic agent or a detection moiety.

In one embodiment, the invention relates to a method of treating or preventing a disease or disorder associated with increased levels of apo RAS in a subject, the method comprising the step of administering to the subject a composition comprising at least one molecule that specifically binds Ras in a nucleotide free state (apo RAS). In one embodiment, the apo RAS binding molecule is a chemical compound, a protein, a peptide, a peptidomemetic, an antibody, an antibody fragment, an antibody mimetic, a monobody, a fusion protein comprising a monobody domain, an aptamer, a ribozyme, a small molecule chemical compound, an short hairpin RNA, an antisense nucleic acid molecule, siRNA, miRNA, a nucleic acid encoding an antisense nucleic acid molecule, or a nucleic acid sequence encoding a protein. In one embodiment, the molecule that specifically binds apo RAS a monobody or a fusion protein comprising a monobody domain. In one embodiment, the monobody or monobody domain comprises a peptide sequence of SEQ ID NO: 1-32, a variant thereof, or a fragment thereof. In one embodiment, the fusion protein comprising a monobody domain further comprises a therapeutic agent or a detection moiety.

In one embodiment, the composition is administered to the subject in combination with a second therapeutic agent.

In one embodiment, the disease or disorder associated with increased levels of apo RAS is cancer.

In one embodiment, the invention relates to an isolated nucleic acid molecule encoding at least one molecule that specifically binds Ras in a nucleotide free state (apo RAS). In one embodiment, the apo RAS binding molecule is a chemical compound, a protein, a peptide, a peptidomemetic, an antibody, an antibody fragment, an antibody mimetic, a monobody, a fusion protein comprising a monobody domain, an aptamer, a ribozyme, a small molecule chemical compound, an short hairpin RNA, an antisense nucleic acid molecule, siRNA, miRNA, a nucleic acid encoding an antisense nucleic acid molecule, or a nucleic acid sequence encoding a protein.

In one embodiment, the isolated nucleic acid molecule encodes a monobody or a fusion protein comprising a monobody domain. In one embodiment, the monobody or monobody domain comprises a peptide sequence of SEQ ID NO: 1-32, a variant thereof, or a fragment thereof.

In one embodiment, the invention relates to an expression vector comprising an isolated nucleic acid molecule encoding at least one molecule that specifically binds Ras in a nucleotide free state (apo RAS). In one embodiment, the apo RAS binding molecule is a chemical compound, a protein, a peptide, a peptidomemetic, an antibody, an antibody fragment, an antibody mimetic, a monobody, a fusion protein comprising a monobody domain, an aptamer, a ribozyme, a small molecule chemical compound, an short hairpin RNA, an antisense nucleic acid molecule, siRNA, miRNA, a nucleic acid encoding an antisense nucleic acid molecule, or a nucleic acid sequence encoding a protein.

In one embodiment, the isolated nucleic acid molecule encodes a monobody or a fusion protein comprising a monobody domain. In one embodiment, the monobody or monobody domain comprises a peptide sequence of SEQ ID NO: 1-32, a variant thereof, or a fragment thereof.

In one embodiment, the invention relates to a host cell comprising an isolated nucleic acid molecule encoding at least one molecule that specifically binds Ras in a nucleotide free state (apo RAS). In one embodiment, the apo RAS binding molecule is a chemical compound, a protein, a peptide, a peptidomemetic, an antibody, an antibody fragment, an antibody mimetic, a monobody, a fusion protein comprising a monobody domain, an aptamer, a ribozyme, a small molecule chemical compound, an short hairpin RNA, an antisense nucleic acid molecule, siRNA, miRNA, a nucleic acid encoding an antisense nucleic acid molecule, or a nucleic acid sequence encoding a protein.

In one embodiment, the isolated nucleic acid molecule encodes a monobody or a fusion protein comprising a monobody domain. In one embodiment, the monobody or monobody domain comprises a peptide sequence of SEQ ID NO: 1-32, a variant thereof, or a fragment thereof.

In one embodiment, the invention relates to a method of diagnosing a disease or disorder in a subject in need thereof, the method comprising: determining the level of apo RAS in a biological sample of the subject, comparing the level of apo RAS in the biological sample of the subject with a comparator control, and diagnosing the subject with a disease or disorder when the level of apo RAS in the biological sample of subject is elevated when compared with the level of apo RAS of the comparator control. In one embodiment, the method further comprises administering a treatment to the subject that was diagnosed as having a disease or disorder.

In one embodiment, the level of apo RAS in the biological sample is determined by contacting the sample with a composition comprising at least one molecule that specifically binds Ras in a nucleotide free state (apo RAS), selected from the group consisting of a chemical compound, a protein, a peptide, a peptidomemetic, an antibody, an antibody fragment, an antibody mimetic, a monobody, a fusion protein comprising a monobody domain, an aptamer, a ribozyme, a small molecule chemical compound, an short hairpin RNA, an antisense nucleic acid molecule, siRNA, miRNA, a nucleic acid encoding an antisense nucleic acid molecule, a nucleic acid sequence encoding a protein.

In one embodiment, the molecule that specifically binds apo RAS is a monobody or a fusion protein comprising a monobody domain. In one embodiment, the monobody or monobody domain comprises a peptide sequence of SEQ ID NO: 1-32, a variant thereof, or a fragment thereof.

In one embodiment, the level of apo RAS in the biological sample is determined to be elevated when the level of apo RAS is increased by at least 10%, by at least 20%, by at least 30%, by at least 40%, by at least 50%, by at least 60%, by at least 70%, by at least 80%, by at least 90%, by at least 100%, by at least 200%, by at least 300%, by at least 400%, by at least 500%, by at least 600%, by at least 700%, by at least 800%, by at least 900%, or by at least 1000%, when compared with a comparator control.

In one embodiment, the comparator control is a positive control, a negative control, a historical control, a historical norm, or the level of a reference molecule in the biological sample.

In one embodiment, the disease or disorder is cancer.

In one embodiment, the subject is human.

In one embodiment, the invention relates to a method of identifying a modulator of Ras signaling, the method comprising: contacting a sample comprising a Ras polypeptide with a test compound, contacting the sample with a composition comprising at least one molecule that specifically binds Ras in a nucleotide free state (apo RAS). determining the level of apo RAS, and comparing the level of apo RAS in the sample with a comparator control. In one embodiment, the apo RAS binding molecule is a chemical compound, a protein, a peptide, a peptidomemetic, an antibody, an antibody fragment, an antibody mimetic, a monobody, a fusion protein comprising a monobody domain, an aptamer, a ribozyme, a small molecule chemical compound, an short hairpin RNA, an antisense nucleic acid molecule, siRNA, miRNA, a nucleic acid encoding an antisense nucleic acid molecule, or a nucleic acid sequence encoding a protein.

In one embodiment, the molecule that specifically binds apo RAS a monobody or a fusion protein comprising a monobody domain. In one embodiment, the monobody or monobody domain comprises a peptide sequence of SEQ ID NO: 1-32, a variant thereof, or a fragment thereof. In one embodiment, the fusion protein comprising a monobody domain further comprises a therapeutic agent or a detection moiety.

BRIEF DESCRIPTION OF THE DRAWINGS

The foregoing summary, as well as the following detailed description of preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1A depicts exemplary data demonstrating the in vitro affinity of R15 and R18 monobodies for HRAS1-166 using yeast display. FIGS. 1B and 1C depict the binding of FLAG-tagged Monobody fusion proteins CFP-R15 and CFP-R18, respectively, to HA-tagged RAS mutants co-expressed in HEK cells via immunoprecipitation (IP). FLAG IPs are in the top two panels. The bottom two panels represent Western blots of whole cell lysates to confirm protein expression. Antibodies used in Western blots are shown to the right of each panel.

FIG. 2A through FIG. 2E depicts exemplary data demonstrating the in vitro binding of R15m Monobody clones for apo RAS. FIG. 2A depicts the in vitro binding titrations of R15m Monobody clones to NRAS1-174. FIG. 2B depicts the in vitro binding titrations of R15m Monobody clones to KRAS1-174. FIG. 2C depicts the in vitro binding titrations of R15m Monobody clones to HRAS1-174. FIG. 2D depicts the in vitro binding titrations of R15m Monobody clones to HRAS1-166. FIG. 2E depicts the dissociation constant values and associated errors for binding to apo RAS, derived from binding titration experiments depicted in FIG. 2A-2D.

FIG. 4 depicts dissociation constant values and associated errors for the in vitro binding of R15m Monobody clones and NS1 Monobody clone (as reference) for various KRAS mutants in an apo or GTP-bound state, derived from titration experiments depicted in FIG. 3. N.B., no substantial binding sufficient for determining dissociation constant values.

FIG. 9A through FIG. 9D depict exemplary data demonstrating the effects of R15m10 Monobody on RAS activation of ERK-MAPK. FIG. 9A demonstrates that expression of R15m10 in HEK cells inhibits EGF-mediated activation of ERK-MAPK. Following EGF stimulation, MYC-ERK was immunoprecipitated and probed for pERK or total ERK. Expression of Monobodies in whole cell lysates is shown in bottom panel. FIG. 9B demonstrates that expression of R15m10 inhibits activation of ERK-MAPK by RAS mutants which have high intrinsic nucleotide release rates. FIG. 9C demonstrates the effect of CFP-R15m10 on ERK activation. FIG. 9D depicts the quantification of ERK activation. Dotted line indicates level of ERK activation in CFP-transfected cells for each mutant which was normalized to 1.

FIG. 11A through 11F depict exemplary data demonstrating binding of R15 Monobody to nucleotide free RAS in cells. FIG. 11A depicts KRAS(Q61L) co-expression with NS1 and R15. FIG. 11B depicts KRAS(G12D) co-expression with NS1 and R15. FIG. 11C depicts KRAS(G13D) co-expression with NS1 and R15. FIG. 11D depicts HRAS (G12V) co-expression with NS1 and R15. FIGS. 11E and 11F depict total expression of proteins with NS1 and R15, respectively, in whole cell lysates (WCL). HEK cells were co-transfected with the indicated Mb and HA-tagged RAS mutant. Monobodies were subsequently immunoprecipitated with FLAG antibodies to purify the associated RAS mutant protein. IPs were washed extensively with buffer containing high Mg2+ and lacking nucleotide. RAS proteins were then eluted from the immune complex with buffer containing low concentrations of SDS and deoxycholate (DOC). Eluted RAS proteins were then recovered and diluted 10-fold with buffer lacking SDS and DOC. Purified RAS proteins were then normalized to equivalent levels and incubated with GST-RAF-RBD to determine the level of active GTP-loaded RAS. As indicated, NS1 purified RAS-GTP as the purified RAS proteins robustly bound GST-RAF RBD both in the absence and presence of added GTPγS. In contrast, R15m10 purified RAS proteins did not interact with GST-RAF RBD indicating that they were not in the active, GTP-bound state despite being oncogenic RAS mutants. However, addition of GTPγS (+GTP) to the R15m10 purified RAS proteins reconstituted binding to the RAF-RBD.

FIG. 12A through FIG. 12D depict exemplary data demonstrating that R15m10 Monobody binds nucleotide free RAS in cells. FIG. 12A depicts data demonstrating that R15m10 Monobody binds RAS mutants in the nucleotide-free state in cells. Lanes 1-4 depict the amount of RAS protein purified from cell lysates during an anti-FLAG immunoprecipitation and then released from the immuno-precipicated protein. Lanes 5-6 depict the amount of RAS protein eluted from NS1 Monobody IP that binds to the GST-RAF-RBD protein in vitro in the absence of added nucleotide. Lanes 7-8 depict the amount of RAS protein eluted from NS1 Monobody IP that binds to the GST-RAF-RBD protein in vitro in the presence of added GTPgS. Lanes 9-10 depict the amount of RAS protein eluted from R15m$^{10}$ Monobody IP that binds to the GST-RAF-RBD protein in vitro in the absence of added nucleotide. Lanes 11-12 depicts the amount of RAS protein eluted from R15m$^{10}$ Monobody IP that binds to the GST-RAF-RBD protein in vitro in the presence of GTPγS. FIG. 12B demonstrates that Monobody purified RAS proteins do not spontaneously exchange nucleotide in vitro under these defined experimental conditions. RAS proteins were co-IPed with NS1. Following extensive washing, the purified KRAS protein was incubated in the absence (−) or presence of GDP or GTPγS and then tested for binding to GST-RAF-RBD. Addition of GDP did not affect binding of NS1-purified KRAS to RAF indicating that GDP did not displace bound nucleotide on the purified RAS protein. FIG. 12C depicts the amount of RAS protein immunoprecipitated with the indicated Monobody protein co-expressed in cells. FIG. 12D depicts the expression of the indicated proteins in whole cell lysates (WCL).

FIG. 13A depicts NIH/3T3 cells that were transfected with the indicated RAS mutants along with CFP or CFP-tagged Monobody and allowed to sit at confluence for 2-3 weeks. Foci were stained with crystal violet. NS1 was used as a control for inhibition of KRAS and HRAS mutants. R15m10 selectively inhibited Q61L mutants of all three RAS isoforms but did not affect G12V mutants. Neither monobody affected transformation by oncogenic BRAF or MEK mutants further demonstrating selectivity and lack of off-target effects. FIG. 13B depicts the quantification of focus-formation assays. Results represent the ratio of foci number in the presence of CFP-NS1 or CFP-R15m10 to that with CFP alone and are mean±s.d. of 3 independent experiments performed in triplicate.

FIG. 14A through FIG. 14C depict exemplary data demonstrating binding of apo-specific Monobodies to RAS. FIG. 14A depicts the effect of serum on the co-precipitation of FLAG-tagged Monobodies with KRAS mutant proteins. Co-immunoprecipitation of FLAG-tagged CFP-R15m10 with the indicated HRAS mutant was examined in the presence (+) or absence (−) of serum. Serum depletion significantly enhances R15m10 binding to HRAS(Q61L), a fast cycling RAS mutant suggesting that exchange factors are not needed for creation of apoRAS and binding R15m10.

FIG. 14B demonstrates that mutation of the GEF binding interface on RAS enhances RAS interaction with apo-specific monobody R15m10. Experiments were performed both in the presence and absence of serum. Disrupting KRAS interactions with exchange factors by mutation D69N increased interaction of KRAS with apo-specific Monobody R15. FIG. 14C depicts experiments performed as in FIG. 14B with HRAS mutants but only under serum-starved conditions.

FIG. 15A through FIG. 15B depict exemplary data demonstrating that R15m10 disrupts interactions of fast cycling RAS mutants with CRAF and heterodimerization of CRAF-BRAF. HEK cells were co-transfected with CFP or the indicated CFP-tagged Mb. Cells were then serum starved and then cell lysates immunoprecipitated with antibodies to CRAF. These CRAF IPs were then fractionated on SDS-denaturing gels and analyzed by Western blot for the co-association of CRAF with the indicated proteins. FIG. 15A demonstrates that R15m10 disrupts interaction of CRAF with fast-cycling RAS mutants (top panel) and the heterodimerization with BRAF (2nd panel from top). NS1 does not affect NRAS interaction with CRAF or CRAF:BRAF heterodimerization as previously described (Spencer-Smith et al (2017) Nat Cell Biol). FIG. 15B demonstrates that R15m10 disrupts RAS:CRAF interaction and CRAF:BRAF heterodimerization by KRAS(Q61L) and NRAS(G12D) fast cycling mutants but not NRAS(G12V) slow cycling mutant. NS1 does not affect CRAF interactions with NRAS as expected.

FIGS. 16A through 16J depict exemplary data demonstrating that chemical induction of R15m10 inhibits signaling and growth of tumor cell lines driven by fast cycling RAS mutants. Applicants generated stable cell lines in which R15m10 expression was induced by treatment with doxycycline (DOX). ERK-MAPK activation was then measured in the absence (−DOX) or presence (+DOX) of R15 expression. The mutant RAS protein expressed in each cell line is indicated below the cell name. FIG. 16A depicts H1915, a human lung tumor line, with an HRAS(Q61L) mutation; FIG. 16B depicts LS1034, a human colorectal cell line, with a KRAS(A146T) mutation; FIG. 16C depicts KPC, mouse pancreatic tumor cell line, generated from the KPC mouse model bearing a KRAS(G12D) mutation; FIG. 16D depicts PANC-1, a human pancreatic ductal adenocarcinoma tumor cell line, with a KRAS(G12D) mutation; FIG. 16E depicts CFPAC-1, a human pancreatic ductal adenocarcinoma tumor cell line, with a KRAS(G12V) mutation. FIGS. 16F through 16J demonstrate that induction of R15m10 expression inhibits proliferation of tumor lines with fast cycling RAS mutations. Proliferation was measured using CellTiterGlo over the indicated time periods in the absence (−DOX) or presence (+DOX) of R15 expression. NOTE: Doxycycline treatment does not affect pERK levels or proliferation in parental cells that have not been transfected with R15m10 (data not shown).

FIGS. 17A through 17E depict exemplary data demonstrating that chemical induction of R15m10 inhibits anchorage-independent growth of tumor cell lines driven by fast cycling RAS mutants. Cell lines generated in FIG. 16 were plated in soft agar in the absence or presence of DOX and allowed to grow for 3-4 weeks. Expression of R15 (+DOX) reduces anchorage independent growth in lines expressing fast cycling RAS mutants, as shown in FIGS. 17A through 17D, but not in a cell line expressing a slow cycling mutant, shown in 17E. Quantification of soft agar colonies is shown in the graphs below the images. Results represent the average number of colonies in triplicate wells +/−std. dev. P values are shown from Student's t-test. NOTE: Doxycycline treatment does not affect anchorage independent growth in parental cells that have not been transfected with R15m10 (data not shown).

FIGS. 18A through 18D depict exemplary data demonstrating that chemical induction of R15m10 inhibits tumor development of tumor cell lines driven by fast cycling RAS mutants. R15m10 expressing PANC-1 cells generated in FIG. 16 were injected subcutaneously into the flanks of athymic nude mice. A cohort of mice were provided DOX in their drinking water (+DOX) on the day following injection to induce R15m10 expression which reduced growth of the tumors, as shown in FIG. 18A. (n=6 mice per condition). FIG. 18B depicts weights of tumors from mice in the absence (−DOX) or presence (+DOX) of R15 expression. FIG. 18C depicts Western blot analysis of tumor lysates. R15 was expressed in tumors treated with DOX resulting in a decrease in pERK and pAKT levels compared to untreated mice. FIG. 18D depicts quantification of pERK levels from FIG. 18C.

FIGS. 19A through 19D depict exemplary data demonstrating that chemical induction of R15m10 does not inhibit tumor development of tumor cell lines driven by slow cycling RAS mutants. R15m10 expressing CFPAC-1 cells generated in FIG. 16 were injected subcutaneously into the flanks of athymic nude mice. A cohort of mice were provided DOX in their drinking water (+DOX) on the day following injection to induce R15m10 expression which reduced growth of the tumors, as shown in FIG. 19A (n=6 per condition). FIG. 19B depicts weights of tumors from mice in the absence (−DOX) or presence (+DOX) of R15 expression. FIG. 19C depicts Western blot analysis of tumor lysates. R15 was expressed in tumors treated with DOX resulting in a decrease in pERK levels compared to untreated mice. FIG. 19D depicts quantification of pERK levels from FIG. 19C.

FIGS. 20A through 20E further depict exemplary data demonstrating that chemical induction of R15m10 inhibits tumor development of tumor cell lines driven by fast cycling RAS mutants. R15m10 expressing H1915 cells generated in FIG. 16 were injected subcutaneously into the flanks of athymic nude mice. A cohort of mice were provided DOX in their drinking water (+DOX) to induce R15m10 expression which reduced growth of the tumors, as shown in FIG. 20A (n=6 mice per condition). No tumors were detected in DOX treated mice at 39 days when −DOX mice were sacrificed. The +DOX mice were then removed from DOX treatment and observed. Three of the 6 mice developed tumors by Day 53. On Day 55 these three mice were again treated with DOX to induced R15 expression. These 3 mice were sacrificed at Day 67 along with the remaining 3 mice that did not subsequently develop tumors upon removal from DOX. FIG. 20B depicts Western blot analysis of tumor lysates. Note: the +Dox(1) represent lysates from tumors arising in 3 mice that were initially treated with DOX, removed from treatment, and then re-treated upon tumor emergence. These tumors did not express detectable levels of R15 suggesting that tumors that developed had lost expression of the R15 monobody. FIG. 20C depicts xenograft tumor development. Experiments were performed as in FIG. 20A except a cohort of mice (n=6) were not treated with DOX until tumors reached 50-70 mm3 (+DOX). R15 induction results in a decrease in tumor size. FIG. 20D depicts Western blot analysis of tumor lysates. R15 was expressed in tumors treated with DOX resulting in a decrease in pERK levels compared to untreated mice. FIG. 20E depicts quantification of pERK levels from FIG. 20D.

FIGS. 21A through 21C further depict exemplary data demonstrating that chemical induction of R15m10 inhibits tumor development of tumor cell lines driven by fast cycling RAS mutants. R15m10 expressing HCT116 cells harboring a KRAS(G13D) mutation were injected subcutaneously into the flanks of athymic nude mice. A cohort of mice were provided DOX in their drinking water (+DOX) on the day following injection to induce R15m10 expression which reduced growth of the tumors, as shown in FIG. 21A (n=6 mice per condition). FIG. 21B depicts Western blot analysis of tumor lysates. R15 was expressed in tumors treated with DOX resulting in a decrease in pERK levels compared to untreated mice. FIG. 21C depicts quantification of pERK levels from FIG. 21B.

DETAILED DESCRIPTION OF THE INVENTION

Figure 1C:
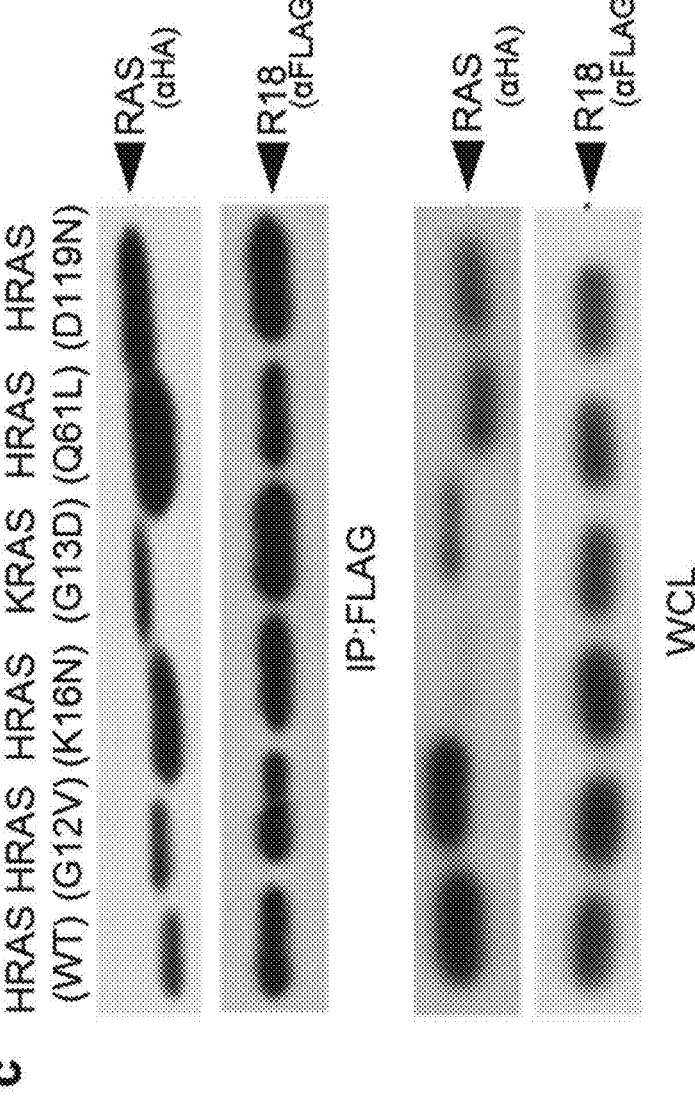

This invention relates to the detection and measurement of nucleotide-free Ras (apo RAS) using an agent that specifically binds to apo RAS. In various embodiments, the invention is directed to compositions and methods for diagnosing, preventing, or treating a disease or disorder associated with aberrant Ras signaling in an individual by performing an assay that measures apo RAS in a biological sample. In various embodiments, the diseases and disorders diagnosable, preventable and treatable using the compositions and methods of the invention include cancers, RASopathies including, but not limited to, neurofibromatosis type 1, Noonan syndrome, Noonan syndrome with multiple lentigines, capillary malformation-arteriovenous malformation syndrome, Costello syndrome, cardio-facio-cutaneous syndrome, and Legius syndrome, and mental disorders including, but not limited to, Alzheimer's disease, Angelman syndrome, autism, cardio-facio-cutaneous syndrome, Coffin-Lowry syndrome, Costello syndrome, Cowden and Bannayan-Riley-Ruvalcaba syndromes, fragile X syndrome, neurofibromatosis type 1, Noonan syndrome, schizophrenia, tuberous sclerosis, and X-linked mental retardation.

In one aspect, the present invention relates to a composition that specifically binds to apo RAS. In one embodiment, the composition comprises an agent that specifically binds to apo RAS, wherein the agent is an apo RAS monobody. In one embodiment, the apo RAS monobody comprises a polypeptide sequence as set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, or SEQ ID NO:32. Therefore, in various embodiments, the invention relates to the detection and measurement of nucleotide free Ras (apo RAS) using an apo RAS monobody. In various embodiments, the invention relates to use of at least one apo RAS monobody of the invention in methods for diagnosing, preventing, or treating a disease or disorder associated with aberrant Ras signaling in an individual. In various embodiments, the diseases and disorders diagnosable, preventable and treatable using at least one apo RAS monobody of the invention include cancers, RASopathies and mental disorders.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

Generally, the nomenclature used herein and the laboratory procedures in cell culture, molecular genetics, organic chemistry, and nucleic acid chemistry and hybridization are those well-known and commonly employed in the art.

Standard techniques are used for nucleic acid and peptide synthesis. The techniques and procedures are generally performed according to conventional methods in the art and various general references (e.g., Sambrook and Russell, 2012, Molecular Cloning, A Laboratory Approach, Cold Spring Harbor Press, Cold Spring Harbor, NY, and Ausubel et al., 2012, Current Protocols in Molecular Biology, John Wiley & Sons, NY), which are provided throughout this document.

The nomenclature used herein and the laboratory procedures used in analytical chemistry and organic syntheses described below are those well-known and commonly employed in the art. Standard techniques or modifications thereof are used for chemical syntheses and chemical analyses.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, or ±10%, or ±5%, or ±1%, or ±0.1% from the specified value, as such variations are appropriate to perform the disclosed methods.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected/homeostatic) respective characteristic. Characteristics which are normal or expected for one cell, tissue type, or subject, might be abnormal for a different cell or tissue type.

The term "analog" as used herein generally refers to compounds that are generally structurally similar to the compound of which they are an analog, or "parent" compound. Generally, analogs will retain certain characteristics of the parent compound, e.g., a biological or pharmacological activity. An analog may lack other, less desirable characteristics, e.g., antigenicity, proteolytic instability, toxicity, and the like. An analog includes compounds in which a particular biological activity of the parent is reduced, while one or more distinct biological activities of the parent are unaffected in the "analog." As applied to polypeptides, the term "analog" may have varying ranges of amino acid sequence identity to the parent compound, for example at least about 70%, more preferably at least about 80%-85% or about 86%-89%, and still more preferably at least about 90%, about 92%, about 94%, about 96%, about 98% or about 99% of the amino acids in a given amino acid sequence the parent or a selected portion or domain of the parent. As applied to polypeptides, the term "analog" generally refers to polypeptides which are comprised of a segment of about at least 3 amino acids that has substantial identity to at least a portion of a binding domain fusion protein. Analogs typically are at least 5 amino acids long, at least 20 amino acids long or longer, at least 50 amino acids long or longer, at least 100 amino acids long or longer, at least 150 amino acids long or longer, at least 200 amino acids long or longer, and more typically at least 250 amino acids long or longer. Some analogs may lack substantial biological activity but may still be employed for various uses, such as for raising antibodies to predetermined epitopes, as an immunological reagent to detect and/or purify reactive antibodies by affinity chromatography, or as a competitive or noncompetitive agonist, antagonist, or partial agonist of a binding domain fusion protein function. The term "antibody," as used herein, refers to an immunoglobulin molecule which is able to specifically bind to a specific epitope of a binding partner molecule. Antibodies can be intact immunoglobulins derived from natural sources, or from recombinant sources and can be immunoreactive portions of intact immunoglobulins. The antibodies in the present invention may exist in a variety of forms including, for example, polyclonal antibodies, monoclonal antibodies, intracellular antibodies ("intrabodies"), Fv, Fab, Fab', F(ab)2 and F(ab')2, as well as single chain antibodies (scFv), heavy chain antibodies, such as camelid antibodies, and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, New York; Houston et al., 1988, Proc. Natl. Acad. Sci. USA 85:5879-5883; Bird et al., 1988, Science 242:423-426).

The term "antibody fragment" refers to at least one portion of an intact antibody and refers to the antigenic determining variable regions of an intact antibody. Examples of antibody fragments include, but are not limited to, Fab, Fab', F(ab')2, and Fv fragments, linear antibodies, sdAb (either VL or VH), camelid VHH domains, scFv antibodies, and multi-specific antibodies formed from antibody fragments. The term "scFv" refers to a fusion protein comprising at least one antibody fragment comprising a variable region of a light chain and at least one antibody fragment comprising a variable region of a heavy chain, wherein the light and heavy chain variable regions are contiguously linked via a short flexible polypeptide linker, and capable of being expressed as a single chain polypeptide, and wherein the scFv retains the specificity of the intact antibody from which it was derived. Unless specified, as used herein an scFv may have the VL and VH variable regions in either order, e.g., with respect to the N-terminal and C-terminal ends of the polypeptide, the scFv may comprise VL-linker-VH or may comprise VH-linker-VL. An "antibody heavy chain," as used herein, refers to the larger of the two types of polypeptide chains present in antibody molecules in their naturally occurring conformations, and which normally determines the class to which the antibody belongs.

An "antibody light chain," as used herein, refers to the smaller of the two types of polypeptide chains present in antibody molecules in their naturally occurring conformations. Kappa (κ) and lambda (λ) light chains refer to the two major antibody light chain isotypes.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

A "chimeric antibody" refers to a type of engineered antibody which contains a naturally-occurring variable region (light chain and heavy chains) derived from a donor antibody in association with light and heavy chain constant regions derived from an acceptor antibody.

A "humanized antibody" refers to a type of engineered antibody having its CDRs derived from a non-human donor immunoglobulin, the remaining immunoglobulin-derived parts of the molecule being derived from one (or more) human immunoglobulin(s). In addition, framework support residues may be altered to preserve binding affinity (see, e.g., 1989, Queen et al., Proc. Natl. Acad Sci USA, 86:10029-10032; 1991, Hodgson et al., Bio/Technology, 9:421). A suitable human acceptor antibody may be one selected from a conventional database, e.g., the KABAT database, Los Alamos database, and Swiss Protein database, by homology to the nucleotide and amino acid sequences of the donor antibody. A human antibody characterized by a homology to the framework regions of the donor antibody (on an amino acid basis) may be suitable to provide a heavy chain constant region and/or a heavy chain variable framework region for insertion of the donor CDRs. A suitable acceptor antibody capable of donating light chain constant or variable framework regions may be selected in a similar manner. It should be noted that the acceptor antibody heavy and light chains are not required to originate from the same acceptor antibody. The prior art describes several ways of producing such humanized antibodies (see for example EP-A-0239400 and EP-A-054951).

The term "monobody" as used herein refers to an antibody mimetic or synthetic binding proteins that are constructed using a fibronectin type III domain (FN3) as a molecular scaffold.

"CDRs" are defined as the complementarity determining region amino acid sequences of an antibody which are the hypervariable regions of immunoglobulin heavy and light chains. See, e.g., Kabat et al., Sequences of Proteins of Immunological Interest, 4th Ed., U.S. Department of Health and Human Services, National Institutes of Health (1987). There are three heavy chain and three light chain CDRs (or CDR regions) in the variable portion of an immunoglobulin. Thus, "CDRs" as used herein refers to all three heavy chain CDRs, or all three light chain CDRs (or both all heavy and all light chain CDRs, if appropriate). The structure and protein folding of the antibody may mean that other residues are considered part of the binding region and would be understood to be so by a skilled person. See for example Chothia et al., (1989) Conformations of immunoglobulin hypervariable regions; Nature 342, p 877-883.

The term "framework" or "framework sequence" refers to the remaining sequences of a variable region minus the CDRs. Because the exact definition of a CDR sequence may be determined by different systems, the meaning of a framework sequence is subject to correspondingly different interpretations. The six CDRs (CDR-L1, -L2, and -L3 of light chain and CDR-H1, -H2, and -H3 of heavy chain) also divide the framework regions on the light chain and the heavy chain into four sub-regions (FR1, FR2, FR3 and FR4) on each chain, in which CDR1 is positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FR's within the variable region of a single, naturally occurring immunoglobulin chain. An FR represents one of the four sub-regions, and FRs represents two or more of the four sub-regions constituting a framework region.

As used herein, an "immunoassay" refers to any binding assay that uses an antibody capable of binding specifically to a target molecule to detect and quantify the target molecule.

By the term "specifically binds," as used herein with respect to an antibody, is meant an antibody which recognizes a specific binding partner molecule, but does not substantially recognize or bind other molecules in a sample. For example, an antibody that specifically binds to a binding partner molecule from one species may also bind to that binding partner molecule from one or more species. But, such cross-species reactivity does not itself alter the classification of an antibody as specific. In another example, an antibody that specifically binds to binding partner molecule may also bind to different allelic forms of the binding partner molecule. However, such cross reactivity does not itself alter the classification of an antibody as specific.

In some instances, the terms "specific binding" or "specifically binding", can be used in reference to the interaction of an antibody, a protein, or a peptide with a second binding partner molecule, to mean that the interaction is dependent upon the presence of a particular structure (e.g., an antigenic determinant or epitope) on the binding partner molecule; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody. In some instances, the terms "specific binding" and "specifically binding" refers to selective binding, wherein the antibody recognizes a sequence or conformational epitope important for the enhanced affinity of binding to the binding partner molecule.

The term "epitope" has its ordinary meaning of a site on binding partner molecule recognized by an antibody or a binding portion thereof or other binding molecule, such as, for example, a monobody. Epitopes may be molecules or segments of amino acids, including segments that represent a small portion of a whole protein or polypeptide. Epitopes may be conformational (i.e., discontinuous). That is, they may be formed from amino acids encoded by noncontiguous parts of a primary sequence that have been juxtaposed by protein folding.

The phrase "biological sample" as used herein, is intended to include any sample comprising a cell, a tissue, or a bodily fluid in which expression of a nucleic acid or polypeptide can be detected. Examples of such biological samples include but are not limited to blood, lymph, bone marrow, biopsies and smears. Samples that are liquid in nature are referred to herein as "bodily fluids." Biological samples may be obtained from a patient by a variety of techniques including, for example, by scraping or swabbing an area or by using a needle to obtain bodily fluids. Methods for collecting various body samples are well known in the art.

The term "cancer" as used herein is defined as disease characterized by the abnormal growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer (e.g., melanoma), pancreatic cancer, colorectal cancer, renal cancer, liver cancer, brain cancer, lymphoma, leukemia, lung cancer, sarcoma and the like.

As used herein, "conjugated" refers to covalent attachment of one molecule to a second molecule.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

A "coding region" of a mRNA molecule also consists of the nucleotide residues of the mRNA molecule which are matched with an anti-codon region of a transfer RNA molecule during translation of the mRNA molecule or which encode a stop codon. The coding region may thus include nucleotide residues comprising codons for amino acid residues which are not present in the mature protein encoded by the mRNA molecule (e.g., amino acid residues in a protein export signal sequence).

"Complementary" as used herein to refer to a nucleic acid, refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

As used herein, the term "derivative" includes a chemical modification of a polypeptide, polynucleotide, or other molecule. In the context of this invention, a "derivative polypeptide," for example, one modified by glycosylation, pegylation, or any similar process, retains binding activity. For example, the term "derivative" of binding domain includes binding domain fusion proteins, variants, or fragments that have been chemically modified, as, for example, by addition of one or more polyethylene glycol molecules, sugars, phosphates, and/or other such molecules, where the molecule or molecules are not naturally attached to wild-type binding domain fusion proteins. A "derivative" of a polypeptide further includes those polypeptides that are "derived" from a reference polypeptide by having, for example, amino acid substitutions, deletions, or insertions relative to a reference polypeptide. Thus, a polypeptide may be "derived" from a wild-type polypeptide or from any other polypeptide. As used herein, a compound, including polypeptides, may also be "derived" from a particular source, for example from a particular organism, tissue type, or from a particular polypeptide, nucleic acid, or other compound that is present in a particular organism or a particular tissue type.

The term "DNA" as used herein is defined as deoxyribonucleic acid.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting there from. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the noncoding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a sign or symptom of the disease or disorder, the frequency with which such a sign or symptom is experienced by a patient, or both, is reduced.

An "effective amount" or "therapeutically effective amount" of a compound is that amount of compound which is sufficient to provide a beneficial effect to the subject to which the compound is administered.

The term "high affinity" for binding domain polypeptides described herein refers to a dissociation constant (Kd) of at least about $10^{-6}$M, preferably at least about $10^{-7}$M, more preferably at least about $10^{-8}$M or stronger, more preferably at least about $10^{-9}$M or stronger, more preferably at least about $10^{-10}$M or stronger, for example, up to $10^{-12}$M or stronger. However, "high affinity" binding can vary for other binding domain polypeptides.

The term "inhibit," as used herein, means to suppress or block an activity or function, for example, about ten percent relative to a control value. Preferably, the activity is suppressed or blocked by 50% compared to a control value, more preferably by 75%, and even more preferably by 95%. "Inhibit," as used herein, also means to reduce the level of a molecule, a reaction, an interaction, a gene, an mRNA, and/or a protein's expression, stability, function or activity by a measurable amount or to prevent entirely. Inhibitors are compounds that, e.g., bind to, partially or totally block activity, decrease, prevent, delay activation, inactivate, desensitize, or down regulate a protein, a gene, and an mRNA stability, expression, function and activity, e.g., antagonists.

The terms "modulator" and "modulation" of a molecule of interest, as used herein in its various forms, is intended to encompass antagonism, agonism, partial antagonism and/or partial agonism of an activity associated the protease of interest. In various embodiments, "modulators" may inhibit or stimulate protease expression or activity. Such modulators include small molecules agonists and antagonists of a protease molecule, antisense molecules, ribozymes, triplex molecules, and RNAi polynucleotides, and others.

As used herein, an "instructional material" includes a publication, a recording, a diagram, or any other medium of expression which can be used to communicate the usefulness of a compound, composition, vector, or delivery system of the invention in the kit for effecting alleviation of the various diseases or disorders recited herein. Optionally, or alternately, the instructional material can describe one or more methods of alleviating the diseases or disorders in a cell or a tissue of a mammal. The instructional material of the kit of the invention can, for example, be affixed to a container which contains the identified compound, composition, vector, or delivery system of the invention or be shipped together with a container which contains the identified compound, composition, vector, or delivery system. Alternatively, the instructional material can be shipped separately from the container with the intention that the instructional material and the compound be used cooperatively by the recipient.

"Isolated" means altered or removed from the natural state. For example, a nucleic acid or a peptide naturally present in its normal context in a living animal is not "isolated," but the same nucleic acid or peptide partially or completely separated from the coexisting materials of its natural context is "isolated." An isolated nucleic acid or protein can exist in substantially purified form, or can exist in a non-native environment such as, for example, a host cell.

An "isolated nucleic acid" refers to a nucleic acid segment or fragment which has been separated from sequences which flank it in a naturally occurring state, i.e., a DNA fragment which has been removed from the sequences which are normally adjacent to the fragment, i.e., the sequences adjacent to the fragment in a genome in which it naturally occurs. The term also applies to nucleic acids which have been substantially purified from other components which naturally accompany the nucleic acid, i.e., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (i.e., as a cDNA or a genomic or cDNA fragment produced by PCR or restriction enzyme digestion) independent of other sequences. It also includes a recombinant DNA which is part of a hybrid gene encoding additional polypeptide sequence.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine. The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "conservative substitution," when describing a polypeptide, refers to a change in the amino acid composition of the polypeptide that does not substantially alter the activity of the polypeptide, i.e., substitution of amino acids with other amino acids having similar properties. Conservative substitution tables providing functionally similar amino acids are well known in the art. The following six groups each contain amino acids that are generally understood to represent conservative substitutions for one another: (1) Alanine (A), Serine (S), Threonine (T); (2) Aspartic acid (D), Glutamic acid (E); (3) Asparagine (N), Glutamine (Q); (4) Arginine (R), Lysine (K); (5) Isoleucine (I), Leucine (L), Methionine (M), Valine (V); and (6) Phenylalanine (F), Tyrosine (Y), Tryptophan (W) (see also, Creighton, 1984, Proteins, W.H. Freeman and Company). In addition to the above-defined conservative substitutions, other modifications of amino acid residues can also result in "conservatively modified variants." For example, one may regard all charged amino acids as substitutions for each other whether they are positive or negative. In addition, conservatively modified variants can also result from individual substitutions, deletions or additions which alter, add or delete a single amino acid or a small percentage of amino acids, for example, often less than 5%, in an encoded sequence. Further, a conservatively modified variant can be made from a recombinant polypeptide by substituting a codon for an amino acid employed by the native or wild-type gene with a different codon for the same amino acid.

The term "RNA" as used herein is defined as ribonucleic acid.

The term "recombinant DNA" as used herein is defined as DNA produced by joining pieces of DNA from different sources.

The term "recombinant polypeptide" as used herein is defined as a polypeptide produced by using recombinant DNA methods.

By "pharmaceutically acceptable" it is meant, for example, a carrier, diluent or excipient that is compatible with the other ingredients of the formulation and generally safe for administration to a recipient thereof. As used herein, "pharmaceutically acceptable carrier" includes any material, which when combined with the conjugate retains the conjugates' activity and is non-reactive with the subject's immune systems. Examples include, but are not limited to, any of the standard pharmaceutical carriers such as a phosphate buffered saline solution, water, emulsions such as oil/water emulsion, and various types of wetting agents. Other carriers may also include sterile solutions, tablets including coated tablets and capsules. Typically such carriers contain excipients such as starch, milk, sugar, certain types of clay, gelatin, stearic acid or salts thereof, magnesium or calcium stearate, talc, vegetable fats or oils, gums, glycols, or other known excipients. Such carriers may also include flavor and color additives or other ingredients. Compositions comprising such carriers are formulated by well-known conventional methods.

The terms "patient," "subject," "individual," and the like are used interchangeably herein, and refer to any animal, preferably a mammal, and most preferably a human, having a complement system, including a human in need of therapy for, or susceptible to, a condition or its sequelae. Thus, the individual may include, for example, dogs, cats, pigs, cows, sheep, goats, horses, rats, monkeys, and mice and humans.

The phrase "percent (%) identity" refers to the percentage of sequence similarity found in a comparison of two or more amino acid sequences. Percent identity can be determined electronically using any suitable software. Likewise, "similarity" between two polypeptides (or one or more portions of either or both of them) is determined by comparing the amino acid sequence of one polypeptide to the amino acid sequence of a second polypeptide. Any suitable algorithm useful for such comparisons can be adapted for application in the context of the invention.

A "therapeutic" treatment is a treatment administered to a subject who exhibits signs of pathology, for the purpose of diminishing or eliminating those signs.

"Therapeutically effective amount" is an amount of a compound of the invention, that when administered to a patient, ameliorates a symptom of the disease. The amount of a compound of the invention which constitutes a "therapeutically effective amount" will vary depending on the compound, the disease state and its severity, the age of the patient to be treated, and the like. The therapeutically effective amount can be determined routinely by one of ordinary skill in the art having regard to his own knowledge and to this disclosure.

The terms "treat," "treating," and "treatment," refer to therapeutic or preventative measures described herein. The methods of "treatment" employ administration to a subject, in need of such treatment, a composition of the present invention, for example, a subject afflicted a disease or disorder, or a subject who ultimately may acquire such a disease or disorder, in order to prevent, cure, delay, reduce the severity of, or ameliorate one or more symptoms of the disorder or recurring disorder, or in order to prolong the survival of a subject beyond that expected in the absence of such treatment.

"Variant" as the term is used herein, is a nucleic acid sequence or a peptide sequence that differs in sequence from a reference nucleic acid sequence or peptide sequence respectively, but retains essential biological properties of the reference molecule. Changes in the sequence of a nucleic acid variant may not alter the amino acid sequence of a peptide encoded by the reference nucleic acid, or may result in amino acid substitutions, additions, deletions, fusions and truncations. Changes in the sequence of peptide variants are typically limited or conservative, so that the sequences of the reference peptide and the variant are closely similar overall and, in many regions, identical. A variant and reference peptide can differ in amino acid sequence by one or more substitutions, additions, deletions in any combination. A variant of a nucleic acid or peptide can be a naturally occurring such as an allelic variant, or can be a variant that is not known to occur naturally. Non-naturally occurring variants of nucleic acids and peptides may be made by mutagenesis techniques or by direct synthesis Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

This invention relates to a molecule that specifically binds RAS in the nucleotide-free state (apo RAS), and methods of using the molecule to measure apo RAS or to inhibit one or more RAS activity. In various embodiments, the invention is directed to compositions and methods for diagnosing, preventing, or treating a disease or disorder associated with a mutation in one or more allele of the RAS gene in an individual. In some embodiments, the apo RAS binding molecule is a monobody. In various embodiments, the diseases and disorders diagnosable, preventable and treatable using the compositions and methods of the invention include cancers, RASopathies including, but not limited to, neurofibromatosis type 1, Noonan syndrome, Noonan syndrome with multiple lentigines, capillary malformation-arteriovenous malformation syndrome, Costello syndrome, cardio-facio-cutaneous syndrome, and Legius syndrome, and mental disorders including, but not limited to, Alzheimer's disease, Angelman syndrome, autism, cardio-facio-cutaneous syndrome, Coffin-Lowry syndrome, Costello syndrome, Cowden and Bannayan-Riley-Ruvalcaba syndromes, fragile X syndrome, neurofibromatosis type 1, Noonan syndrome, schizophrenia, tuberous sclerosis, and X-linked mental retardation.

Apo RAS Binding Compositions and Methods of Use

In some embodiments, the present invention includes methods of measuring the level of apo RAS in an individual, using the apo RAS binding compositions described herein. In certain embodiments, the method comprises comparing the detected level of apo RAS with a comparator control. Non-limiting examples of comparators include, but are not limited to, a reference standard, a negative control, a positive control, a level of a housekeeping gene or gene product, an expected normal background value of the subject, a historical normal background value of the subject, an expected normal background value of a population that the subject is a member of, or a historical normal background value of a population that the subject is a member of.

It will be understood by one skilled in the art, based upon the disclosure provided herein, that a measurement of the level of apo RAS encompasses measurement of apo RAS at the protein level. The apo RAS measurement compositions and methods of the invention can selectively measure apo RAS, or can measure both apo RAS and another molecule.

Measurement of apo RAS can be performed using a wide variety of methods, including those disclosed herein, as well as methods known in the art or to be developed in the future.

That is, the routine practitioner would appreciate, based upon the disclosure provided herein, that measuring the level of apo RAS can be readily performed using methods that assess the level of a RAS polypeptide in a nucleic-acid free state.

In various embodiments, the present invention includes apo RAS binding compositions and methods of treating or preventing a disease or disorder associated with a mutation in one or more allele of the RAS gene which results in an altered level of apo RAS. In one embodiment, the apo RAS binding compositions and methods of the invention measure the amount of apo RAS polypeptide in a sample. In one embodiment, the apo RAS binding compositions and methods the invention sequesters RAS polypeptide in an apo state.

One skilled in the art, based upon the disclosure provided herein, would understand that the invention is useful in treating or preventing a disease or disorder in a subject in need thereof, whether or not the subject is also being treated with other medication or therapy. Further, the skilled artisan would further appreciate, based upon the teachings provided herein, that the diseases or disorders treatable by the compositions and methods described herein encompass any disease or disorder where RAS plays a role. In various embodiments, the disease or disorder treatable or preventable using the compounds and methods of the invention includes cancers, RASopathies including, but not limited to, neurofibromatosis type 1, Noonan syndrome, Noonan syndrome with multiple lentigines, capillary malformation-arteriovenous malformation syndrome, Costello syndrome, cardio-facio-cutaneous syndrome, and Legius syndrome, and mental disorders including, but not limited to, Alzheimer's disease, Angelman syndrome, autism, cardio-facio-cutaneous syndrome, Coffin-Lowry syndrome, Costello syndrome, Cowden and Bannayan-Riley-Ruvalcaba syndromes, fragile X syndrome, neurofibromatosis type 1, Noonan syndrome, schizophrenia, tuberous sclerosis, and X-linked mental retardation.

One of skill in the art will appreciate that molecules that bind to apo RAS can be utilized acutely (e.g., over a short period of time, such as a day, a week or a month) or chronically (e.g., over a long period of time, such as several months or a year or more). One of skill in the art will appreciate that the compositions and methods disclosed herein can be utilized singly or in any combination with other compositions and methods. Further, apo RAS measurement can be performed singly or in any combination with another assay in a temporal sense, in that they may be performed concurrently, or before, and/or after each other. One of ordinary skill in the art will appreciate, based on the disclosure provided herein, that apo RAS binding molecules can be used in methods to monitor, treat or prevent a disease or disorder in a subject in need thereof, and that apo RAS binding molecules can be used alone or in any combination with another composition to effect a diagnostic or therapeutic result.

It will be appreciated by one of skill in the art, when armed with the present disclosure including the methods detailed herein, that the invention is not limited to treatment of a disease or disorder, such as cancers, RASopathies and mental disorders. Particularly, the disease or disorder need not have manifested to the point of detriment to the subject; indeed, the disease or disorder need not be detected in a subject before apo RAS is measured. That is, significant disease or disorder does not have to occur before the present invention may provide benefit. Therefore, the present invention includes a method for preventing a disease or disorder in a subject, in that an apo RAS binding molecule, as discussed herein, can be used prior to the onset of the disease or disorder, as part of a method of preventing the disease or disorder from developing. The preventive methods described herein also include monitoring or treatment of a subject that is in remission for the prevention of a recurrence of a disease or disorder.

Additionally, as disclosed elsewhere herein, one skilled in the art would understand, once armed with the teaching provided herein, that the present invention encompasses a method of preventing a wide variety of diseases, disorders and pathologies where a change in expression and/or activity of RAS is characteristic of the disease, disorder or pathology. Methods for assessing whether a disease relates to the levels or activity of RAS are known in the art. Further, the invention encompasses treatment or prevention of such diseases discovered in the future.

The invention encompasses use of a composition that binds apo RAS to practice the methods of the invention; the skilled artisan would understand, based on the disclosure provided herein, how to formulate the appropriate apo RAS binding molecule. However, the present invention is not limited to any particular method of formulation.

In some instances, apo RAS can be used as a diagnostic marker for diseases or disorders including, but not limited to, cancers, RASopathies and mental disorders. Patients with mutations in RAS possess altered levels of apo RAS, and are at risk of developing cancers, RASopathies and mental disorders. Accordingly, also included in the invention are methods of diagnosing susceptibility to disorders and diseases, including cancers, RASopathies and mental disorders, based on the detection and/or quantitation of apo RAS using the apo RAS binding agents of the present invention. For example, increased levels of apo RAS would be a diagnostic marker for a disorder associated with oncogenic RAS mutants including, but not limited to, HRAS(Q61L), KRAS (Q61L), NRAS(Q61L), KRAS(G13D), and KRAS(A146T), which spontaneously releases nucleotide at an elevated rate compared to wild type RAS. The compositions and methods of the present invention can be used to treat, prevent, reduce or ameliorate a disease or disorder associated with altered levels of apo RAS.

In one embodiment, the composition of the present invention comprises a molecule that specifically binds apo RAS. Exemplary apo RAS binding molecules, include, but should not be construed as being limited to, a chemical compound, a protein, a peptide, a peptidomemetic, an antibody, an antibody fragment, an antibody mimetic, a nucleic acid sequence encoding a protein, peptide, peptidomemetic, antibody, antibody fragment, or antibody mimetic, or combinations thereof. One of skill in the art would readily appreciate, based on the disclosure provided herein, that an apo RAS binding molecule encompasses any molecule that is used to bind apo RAS. Additionally, an apo RAS binding molecule encompasses a chemically modified compound, and derivatives, as is well known to one of skill in the chemical arts.

Further, one of skill in the art, when equipped with this disclosure and the methods exemplified herein, would appreciate that an apo RAS binding molecule includes such compounds as discovered in the future, as can be identified by well-known criteria in the art of biochemistry. Therefore, the present invention is not limited in any way to any particular apo RAS binding molecules as exemplified or disclosed herein; rather, the invention encompasses those apo RAS binding molecules that would be understood by the routine practitioner to be useful, as are known in the art and as are discovered in the future.

An apo RAS binding molecule includes, but is not limited to, peptide-based target binding molecules (e.g., antibodies, antibody mimetics, and fragments thereof), as well as nucleotide-based target binding molecules (e.g., aptamers.) Antibodies and antibody mimetics include, but are not limited to, polyclonal antibodies, monoclonal antibodies, intracellular antibodies ("intrabodies"), Fv, Fab and F(ab)2, single chain antibodies (scFv), heavy chain antibodies (such as camelid antibodies), synthetic antibodies, chimeric antibodies, monobodies, DARPins, Anticalins and humanized antibodies, and fusion molecules comprising an apo RAS binding domain. In one embodiment, the apo RAS binding composition of the invention is a monobody that specifically binds to apo RAS. In one embodiment, the apo RAS binding composition of the invention is a fusion protein comprising a monobody domain that specifically binds to apo RAS. In some embodiments, the antibodies of the invention are bispecific antibodies, or antibody mimetics, where the first specificity is to apo RAS and the second specificity is to a second molecule.

Further methods of producing apo RAS binding molecules are well known to those of ordinary skill in the art, including, but not limited to, obtaining a composition from a nucleic acid sequence encoding a protein. Numerous vectors and other compositions and methods are well known for administering a nucleic acid construct encoding a protein to cells or tissues. Therefore, the invention includes a method of using a nucleic acid encoding a protein, peptide, antibody or antibody mimetic that binds to apo RAS. (Sambrook et al., 2012, Molecular Cloning: A Laboratory Manual, Cold Spring Harbor Laboratory, New York; Ausubel et al., 1997, Current Protocols in Molecular Biology, John Wiley & Sons, New York).

In one embodiment, anti-apo RAS binding molecule of the invention immunospecifically bind to at least one epitope of the RAS protein specifically when in a nucleotide-free state, and do not specifically bind to RAS in other states or to other polypeptides, other than apo RAS from other species. The at least one epitope can comprise at least one portion of the RAS protein. The term "epitope" as used herein refers to a protein determinant capable of binding to an antibody or antibody mimetic. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents.

In some embodiments, the invention includes compositions comprising an antibody or antibody mimetic that specifically binds to apo RAS. In one embodiment, the anti-apo RAS antibody is a polyclonal antibody. In another embodiment, the anti-apo RAS antibody is a monoclonal antibody. In some embodiments, the anti-apo RAS antibody is a chimeric antibody. In further embodiments, the anti-apo RAS antibody is a humanized antibody. In one embodiment, the apo RAS specific antibody mimetic is an apo RAS monobody. In some embodiments, the apo RAS is human apo RAS.

The binding portion of an antibody comprises one or more fragments of an antibody that retain the ability to specifically bind to binding partner molecule (e.g., apo RAS). It has been shown that the binding function of an antibody can be performed by fragments of a full-length antibody. Examples of binding fragments encompassed within the term "binding portion" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "binding portion" of an antibody. These antibody fragments are obtained using conventional techniques known to those with skill in the art, and the fragments are screened for utility in the same manner as are intact antibodies. Binding portions can be produced by recombinant DNA techniques, or by enzymatic or chemical cleavage of intact immunoglobulins.

An antibody or antibody mimetic that binds to apo RAS of the invention may be an antibody or antibody mimetic that affects at least one RAS activity or function, such as but not limited to, nucleotide binding. Therefore, in one embodiment, the antibody or antibody mimetic that binds to apo RAS of the invention may trap RAS in a nucleotide-free state.

In one embodiment, antibodies of the invention bind RAS. In one embodiment, the antibodies specifically bind to RAS mutants. In another embodiment, the antibodies specifically bind to HRAS(Q61L), KRAS(Q61L), NRAS (Q61L), KRAS(G13D), or KRAS(A146T).

In one embodiment, the apo RAS binding molecule of the invention or fragment thereof may be linked to other types of polypeptides (e.g., a detection moiety or a reporter polypeptide.) These additional polypeptides may be any amino acid sequence useful for the purification, identification, and/or therapeutic or prophylactic application of the apo RAS binding molecule of the invention. In addition, the additional polypeptide can be a signal peptide, or targeting peptide, etc.

In one embodiment, the apo RAS binding molecule of the invention or fragment thereof may comprise one or more additions, substitutions or deletions which may serve to modify one or more property of the apo RAS binding molecule. In some cases, the other additions, substitutions or deletions may increase the stability (including but not limited to, resistance to proteolytic degradation) of the polypeptide or increase affinity of the polypeptide for its appropriate receptor, ligand and/or binding proteins. In some cases, the other additions, substitutions or deletions may increase the solubility of the polypeptide. In some embodiments sites are selected for substitution with a naturally encoded or non-natural amino acid in addition to another site for incorporation of a non-natural amino acid for the purpose of increasing the polypeptide solubility following expression in recombinant host cells. In some embodiments, the polypeptides comprise another addition, substitution, or deletion that modulates affinity for the associated binding partner, modulates circulating half-life, modulates release or bio-availability, facilitates purification, or improves or alters a particular route of administration. Similarly, the non-natural amino acid polypeptide can comprise chemical or enzyme cleavage sequences, protease cleavage sequences, reactive groups, antibody-binding domains (including but not limited to, FLAG or poly-His) or other affinity based sequences (including but not limited to, FLAG, poly-His, GST, etc.) or linked molecules (including but not limited to, biotin) that improve detection (including but not limited to, GFP), purification, transport through tissues or cell membranes, prodrug release or activation, size reduction, or other traits of the polypeptide.

The methods and compositions described herein include incorporation of one or more non-natural amino acids into a polypeptide. One or more non-natural amino acids may be incorporated at one or more particular positions which does not disrupt activity of the polypeptide. This can be achieved by making "conservative" substitutions, including but not limited to, substituting hydrophobic amino acids with non-natural or natural hydrophobic amino acids, bulky amino acids with non-natural or natural bulky amino acids, hydrophilic amino acids with non-natural or natural hydrophilic amino acids) and/or inserting the non-natural amino acid in a location that is not required for activity.

A variety of biochemical and structural approaches can be employed to select the desired sites for substitution with a non-natural amino acid within the polypeptide. Any position of the polypeptide chain is suitable for selection to incorporate a non-natural amino acid, and selection may be based on rational design or by random selection for any or no particular desired purpose. For example, locations in the polypeptide required for biological activity of a polypeptide can be identified using methods including, but not limited to, point mutation analysis, alanine scanning or homolog scanning methods. Residues other than those identified as critical to biological activity by methods including, but not limited to, alanine or homolog scanning mutagenesis may be good candidates for substitution with a non-natural amino acid depending on the desired activity sought for the polypeptide. Alternatively, the sites identified as critical to biological activity may also be good candidates for substitution with a non-natural amino acid, again depending on the desired activity sought for the polypeptide. Another alternative would be to make serial substitutions in each position on the polypeptide chain with a non-natural amino acid and observe the effect on the activities of the polypeptide. Any means, technique, or method for selecting a position for substitution with a non-natural amino acid into any polypeptide is suitable for use in the methods, techniques and compositions described herein.

Apo RAS Monobodies

In one embodiment, the apo RAS binding molecule comprises a monobody, referred to herein as "apo RAS monobody". For example, in one embodiment, the composition of the present invention encompasses a synthetic antibody or antibody mimetic apo RAS monobody that selectively binds to the nucleotide-free state of the RAS protooncogene. Thus, the apo RAS monobodies described herein represent the first tool to inhibit the signaling and oncogenic activity of these RAS mutants. The studies presented herein illustrate a new approach to selectively interfere with the function of certain RAS oncogenic mutants by targeting the nucleotide-free state. Further, the apo RAS monobodies described herein represents a powerful tool for the potential isolation of novel anti-RAS drugs targeting this state of RAS.

As used herein, "polypeptide monobody" is intended to mean a polypeptide which includes a β-strand domain lacking in disulfide bonds and containing a plurality of β-strands, two or more loop regions each connecting one β-strand to another β-strand, and optionally an N-terminal tail, a C-terminal tail, or both, wherein at least one of the two or more loop regions, the N-terminal tail, or the C-terminal tail is characterized by activity in binding a target protein or molecule. More specifically, such polypeptide monobodies of the present invention can include three or more loop regions or, even more specifically, four or more loop regions. The size of such polypeptide monobodies is preferably less than about 30 kDa, more preferably less than about 20 kDa.

The polypeptide monobodies of the present invention are also characterized by specificity for binding to apo RAS. To achieve the specificity in their binding to apo RAS, the amino acid sequence of the polypeptide monobody has been modified relative to the scaffold used for its construction.

Scaffolds for formation of a polypeptide monobody should be highly soluble and stable. It is small enough for structural analysis, yet large enough to accommodate multiple binding domains so as to achieve tight binding and/or high specificity for its target.

An exemplary scaffold for formation of a polypeptide monobody is the fibronectin type III domain (Fn3). Fibronectin is a large protein which plays essential roles in the formation of extracellular matrix and cell-cell interactions; it consists of many repeats of three types (types I, II, and Ill) of small domains (Baron et al., 1991).

Fn3 itself is the paradigm of a large subfamily (Fn3 family or s-type Ig family) of the immunoglobulin superfamily. The Fn3 family includes cell adhesion molecules, cell surface hormone and cytokine receptors, chaperonins, and carbohydrate-binding domains (for reviews, see Bork Doolittle, 1992; Jones, 1993; Bork et al., 1994; Campbell Spitzfaden, 1994; Harpez Chothia, 1994).

Crystallographic studies have revealed that the structure of the DNA binding domains of the transcription factor NF-kB is also closely related to the Fn3 fold (Ghosh et al., 1995; MUller et al., 1995). These proteins are all involved in specific molecular recognition, and in most cases ligand-binding sites are formed by surface loops, suggesting that the Fn3 scaffold is an excellent framework for building specific binding proteins. The 3D structure of Fn3 has been determined by NMR (Main et al., 1992) and by X-ray crystallography (Leahy et al., 1992; Dickinson et al., 1994). The structure is best described as a 3-sandwich similar to that of antibody VH domain except that Fn3 has seven β-strands instead of nine. There are three loops on each end of Fn3; the positions of the BC, DE, and FG loops approximately correspond to those of CDR 1, 2 and 3 of the VH domain.

Fn3 is small (94 residues), monomeric, soluble, and stable. It is one of few members of IgSF that do not have disulfide bonds and, therefore, is stable under reducing conditions. The tenth type III module of fibronectin Fn3) has a fold similar to that of immunoglobulin domains, with seven (3 strands forming two antiparallel (3 sheets, which pack against each other. The structure of the type H module includes seven (3 strands, which form a sandwich of two antiparallel sheets, one containing three strands (ABE) and the other four strands (C'CFG) (Williams Barclay, 1988). The (3 sheet contains residues Glu-9-Thr-14 Ser-17-Asp-23 and Thr-56-Ser-60 The majority of the conserved residues contribute to the hydrophobic core, with the invariant hydrophobic residues Trp-22 and Try-68 lying toward the N-terminal and C-terminal ends of the core, respectively. The (3 strands are much less flexible and appear to provide a rigid framework upon which functional, flexible loops can be built. The topology is similar to that of immunoglobulin C domains.

In one embodiment, polypeptide monobodies of the present invention are fibronectin type III (Fn3)-derived polypeptide monobodies. Fn3 monobodies include at least two Fn3 β-strand domain sequences with a loop region sequence linked between adjacent p-strand domain sequences and optionally, an N-terminal tail of at least about 2 amino acids, a C-terminal tail of at least about 2 amino acids, or both.

The loop region sequence, the N-terminal tail, or the C-terminal tail, or combinations thereof include an amino acid sequence which has binding specificity for apo RAS. To render a loop region sequence, N-terminal tail, or C-terminal tail capable of binding to apo RAS, either the loop region sequence, the N-terminal tail, the C-terminal tail, or a combination thereof varies by deletion, insertion, or replacement of at least two amino acids from a corresponding loop region, N-terminal tail, or C-terminal tail in a wild-type or mutant Fn3 scaffold.

In one embodiment, an Fn3 scaffold is the tenth Fn3 domain of human fibronectin (FNfn10). In one embodiment, an Fn3 scaffold is the tenth Fn3 domain of human fibronectin which has a modified Asp7, which is replaced by a non-negatively charged amino acid residue Asn, Lys, etc.).

In one embodiment, the monobodies of the invention comprise seven β-strand domain sequences (designated A through G) and six loop regions (AB loop, BC loop, CD loop, DE loop, EF loop, and FG loop) which connect the seven β-strand domain sequences.

In one embodiment, the polypeptide monobody of the present invention can be prepared by recombinant techniques, thereby affording the deletion, insertion, or replacement of at least two amino acids from a corresponding loop region, N-terminal tail, or C-terminal tail in a wild-type or mutant Fn3 scaffold. Deletions can be a deletion of at least two amino acid residues up to substantially all but one amino acid residue appearing in a particular loop region or tail. Insertions can be an insertion of at least two amino acid residues up to about 25 amino acid residues, preferably at least two up to about 15 amino acid residues. Replacements can be replacements of at least two up to substantially all amino acid residues appearing in a particular loop region or tail. Alternatively the polypeptide monobody of the present invention can be prepared as described in described in U.S. Pat. No. 9,512,199B2 (Loew et al.), the contents of which are incorporated herein in their entirety.

The deletions, insertions, and replacements (relative to wild-type or previously known mutant) on Fn3 scaffolds can be achieved using recombinant techniques beginning with a known nucleotide sequence. Desired mutations can be introduced to the Fn3 gene using either cassette mutagenesis, oligonucleotide site-directed mutagenesis techniques (Deng Nickoloff, 1992), or Kunkel mutagenesis (Kunkel et al., 1987).

Both cassette mutagenesis and site-directed mutagenesis can be used to prepare specifically desired nucleotide coding sequences. Cassette mutagenesis can be performed using the same protocol for gene construction described above and the double-stranded DNA fragment coding a new sequence can be cloned into a suitable expression vector. Many mutations can be made by combining a newly synthesized strand (coding mutations) and an oligonucleotide used for the gene synthesis.

Regardless of the approach utilized to introduce mutations into the monobody nucleotide sequence, sequencing can be performed to confirm that the designed mutations (and no other mutations) were introduced by mutagenesis reactions.

In one embodiment, an apo RAS monobody comprises a polypeptide sequence as set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, or SEQ ID NO:32. In one embodiment, an apo RAS monobody comprises a variant of a polypeptide sequence as set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, or SEQ ID NO:32, comprising at least 60%, 65%, 70%, 75%, 80%, 85%, 90%, 91%, 92%, 93%, 94%, 95%, 96%, 97%, 98%, or 99% identity to SEQ ID NO:1, SEQ ID NO:2, SEQ ID NO:3, SEQ ID NO:4, SEQ ID NO:5 or SEQ ID NO:6. In one embodiment, an apo RAS monobody comprises a fragment of a polypeptide sequence as set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, or SEQ ID NO:32, comprising at least 60%, 65%, 70%, 75%, 80%, 85%, 90%, 91%, 92%, 93%, 94%, 95%, 96%, 97%, 98%, or 99% of the full length of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, or SEQ ID NO:32.

In one embodiment, the apo RAS monobody comprises linker which, though not required for formation of a polypeptide monobody of the present invention, is useful in forming fusion proteins.

In one embodiment, the invention includes a nucleic acid molecule encoding an apo RAS monobody polypeptide sequence as set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, or SEQ ID NO:32. In one embodiment, the invention includes a nucleic acid molecule encoding a variant of an apo RAS monobody polypeptide sequence as set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, or SEQ ID NO:32, comprising at least 60%, 65%, 70%, 75%, 80%, 85%, 90%, 91%, 92%, 93%, 94%, 95%, 96%, 97%, 98%, or 99% identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, or SEQ ID NO:32. In one embodiment, the invention includes a nucleic acid molecule encoding a fragment of an apo RAS monobody polypeptide sequence as set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, or SEQ ID NO:32, comprising at least 60%, 65%, 70%, 75%, 80%, 85%, 90%, 91%, 92%, 93%, 94%, 95%, 96%, 97%, 98%, or 99% of the full length of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, or SEQ ID NO:32.

Regardless of the approach used to prepare the nucleic acid molecules encoding the polypeptide monobody, the nucleic acid can be incorporated into host cells using conventional recombinant DNA technology. Generally, this involves inserting the DNA molecule into an expression system to which the DNA molecule is heterologous not normally present). The heterologous DNA molecule is inserted into the expression system or vector in sense orientation and correct reading frame.

The vector contains the necessary elements (promoters, suppressers, operators, transcription termination sequences, etc.) for the transcription and translation of the inserted protein-coding sequences.

Alternatively, a recombinant gene or DNA construct can be prepared prior to its insertion into an expression vector. For example, using conventional recombinant DNA techniques, a promoter-effective DNA molecule can be operably coupled 5' of a DNA molecule encoding the polypeptide monobody and a transcription termination polyadenylation sequence) can be operably coupled 3' thereof. U.S. Pat. No. 4,237,224 to Cohen and Boyer describes the production of expression systems in the form of recombinant plasmids using restriction enzyme cleavage and ligation with DNA ligase. These recombinant plasmids are then introduced by means of transformation and replicated in unicellular cultures including prokaryotic organisms and eukaryotic cells grown in tissue culture.

Recombinant molecules can be introduced into cells via transformation, particularly transduction, conjugation, mobilization, or electroporation. The DNA sequences are cloned into the vector using standard cloning procedures in the art, as described by Sambrook et al. (1989).

A variety of host-vector systems may be utilized to express the polypeptide monobody or fusion protein which includes a polypeptide monobody.

Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; and mammalian cell systems infected with virus vaccinia virus, adenovirus, etc.). The expression elements of these vectors vary in their strength and specificities. Depending upon the host-vector system utilized, any one of a number of suitable transcription and translation elements can be used.

Different genetic signals and processing events control many levels of gene expression DNA transcription and messenger RNA (mRNA) translation).

Transcription of DNA is dependent upon the presence of a promoter which is a DNA sequence that directs the binding of RNA polymerase and thereby promotes mRNA synthesis. The DNA sequences of eukaryotic promoters differ from those of prokaryotic promoters. Furthermore, eukaryotic promoters and accompanying genetic signals may not be recognized in or may not function in a prokaryotic system and, further, prokaryotic promoters may not be recognized in or may not function in eukaryotic cells. Promoters suitable for use in each of these systems are well known in the art.

Similarly, translation of mRNA in prokaryotes depends upon the presence of the proper prokaryotic signals which differ from those of eukaryotes.

Efficient translation of mRNA in prokaryotes requires a ribosome binding site called the Shine-Dalgarno (SD) sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome.

In addition, polyadenylation signals suitable for use in a desired host cell can also be employed to effect appropriate translation of the DNA molecule (encoding the polypeptide monobody of the present invention. Polyadenylation signals suitable for use in each of the above-identified systems are well known in the art.

In one embodiment, a DNA molecule encoding the polypeptide monobody is ligated to appropriate promoter and polyadenylation sequences using conventional recombinant techniques, with the promoter being located upstream or 5' to the DNA molecule and the polyadenylation signal being located downstream or 3' of the DNA molecule. As a result of ligating the DNA molecule to the promoter and polyadenylation signal sequences, a DNA construct of the present invention is formed. This DNA construct can be cloned directly into a suitable expression vector plasmid, viral DNA, etc.) or it can be formed upon cloning the DNA molecule into an empty expression vector which includes an appropriate restriction site intermediate the promoter and polyadenylation signals which are present in the empty vector.

Once the DNA molecule encoding the polypeptide monobody has been cloned into an expression system, it is ready to be incorporated into a host cell. Such incorporation can be carried out by the various forms of transformation noted above, depending upon the vector/host cell system. Suitable host cells include, but are not limited to, bacteria, yeast cells, mammalian cells, etc. Upon growing the host cells in a suitable growth medium, the host cells are encouraged to express the polypeptide monobodies of the present invention.

In one embodiment, it is desirable for the polypeptide monobodies to be produced in substantially purified form, particularly when their administration to a patient is contemplated. Purification can be carried out according to previously reported procedures, which involve metal affinity chromatography for monobodies containing a poly-histidine tag (see Koide et al., 1998).

A further aspect of the present invention relates to fusion proteins which include a polypeptide or polypeptide monobody of the present invention and a second polypeptide linked by peptide bond to the polypeptide or polypeptide monobody. The second polypeptide can be an epitope tag polypeptide, e.g., polyhistidine, (ii) a detectable marker polypeptide, (e.g., GFP, alkaline phosphatase), (iii) a metal ion-complexing polypeptide, or (iv) a DNA-binding polypeptide, e.g., polylysine. Each of these fusion proteins can be prepared using recombinant techniques described above to form an in-frame gene fusion that can be expressed in appropriate host cells. Thereafter, the fusion protein can isolated and purified using the techniques described above.

Once a polypeptide, polypeptide monobody, or fusion protein has been obtained, it can be used for therapeutic, preventative, or diagnostic purposes as described herein. Because a polypeptide, polypeptide monobody, or fusion protein of the present invention is capable of binding apo RAS selectively, it can be used for therapeutic, preventative, or diagnostic purposes, or to modify RAS activity. Although references below are made to use of the polypeptide or polypeptide monobody, it should be appreciated that the polypeptide or polypeptide monobody can also be in the form of a fusion protein or conjugate as described elsewhere herein.

Thus, one aspect of the present invention relates to a method of treating or preventing disease or disorder associated with altered RAS activity which includes administering to a patient in need thereof, an effective amount of a polypeptide or polypeptide monobody of the present invention which selectively binds to apo RAS, thereby treating or preventing the disease or disorder. Such administration is carried out under conditions which are effective to treat or prevent the disease or disorder. Typically, this includes administering the polypeptide or polypeptide monobody to the patient in a manner effective to contact one or more cells expressing RAS with a sufficient amount of the polypeptide or polypeptide monobody to sequester RAS in the apo RAS state in one or more cells. As a result of such sequestration, the diseases or disorders are treated or prevented.

As a result of the present invention, a polypeptide or polypeptide monobody of the present invention (with apo RAS selective binding activity) can be used for blocking Ras-dependent signaling, and tumorigenesis. The inventive polypeptide or polypeptide monobody can also be used for mediated targeting and delivery of therapeutics for disrupting or killing variant RAS bearing (e.g. H-RAS, N-RAS, or K-RAS) neoplasms or tumors. In addition, the inventive polypeptide or polypeptide monobody can be used for visualization or imaging of variant RAS bearing (e.g. H-RAS, N-RAS, or K-RAS) neoplasms or tumors, for example, by Mill or immunoscintigraphy.

In addition, the polypeptide or polypeptide monobody can be used to detect apo RAS in solution, in frozen tissue sections, and in cells; therefore, a polypeptide or polypeptide monobody may be used for the detection and characterization of variant RAS bearing (e.g. H-RAS, N-RAS, or K-RAS) tumor and endothelial cells in human malignancies. Accordingly, a polypeptide or polypeptide monobody of the present invention may be used for identification of tumor vasculature.

Consequently, a polypeptide or polypeptide monobody that recognize apo RAS may be used as a diagnostic agent to identify tumors or cancer cells using conventional immunohistochemical techniques. Further, a polypeptide or polypeptide monobody that recognize apo RAS may be used as a component of a diagnostic device or technique to define disease prognosis. Specifically, histologic sections from fresh-frozen or formalin-fixed paraffin embedded tumor tissue are immunostained with an apo RAS-specific polypeptide or polypeptide monobody using techniques and procedures known to those skilled in the art.

In addition to its administration alone, a number of known delivery techniques can be utilized for the delivery, into cells, of either a polypeptide monobody or a nucleic acid molecule which encodes a polypeptide monobody.

Regardless of the particular method of the present invention which is practiced, when it is desirable to contact a cell to be treated) with a polypeptide or polypeptide monobody of the present invention, or its encoding nucleic acid, it is preferred that the contacting be carried out by delivery of the polypeptide monobody or its encoding nucleic acid to the cell.

One approach for delivering the polypeptide or polypeptide monobody to the cell or its encoding nucleic acid into cells involves the use of liposomes. In one embodiment, this involves providing the polypeptide or polypeptide monobody or its encoding nucleic acid to be delivered, and then contacting the target cell with the liposome under conditions effective for delivery of the polypeptide or polypeptide monobody or nucleic acid into the cell.

Liposomes are vesicles comprised of one or more concentrically ordered lipid bilayers which encapsulate an aqueous phase. They are normally not leaky, but can become leaky if a hole or pore occurs in the membrane, if the membrane is dissolved or degrades, or if the membrane temperature is increased to the phase transition temperature. Current methods of drug delivery via liposomes require that the liposome carrier ultimately become permeable and release the encapsulated drug at the target site. This can be accomplished, for example, in a passive manner wherein the liposome bilayer degrades over time through the action of various agents in the body. Every liposome composition will have a characteristic half-life in the circulation or at other sites in the body and, thus, by controlling the half-life of the liposome composition, the rate at which the bilayer degrades can be somewhat regulated.

In contrast to passive drug release, active drug release involves using an agent to induce a permeability change in the liposome vesicle. Liposome membranes can be constructed so that they become destabilized when the environment becomes acidic near the liposome membrane. When liposomes are endocytosed by a target cell, for example, they can be routed to acidic endosomes which will destabilize the liposome and result in drug release. Alternatively, the liposome membrane can be chemically modified such that an enzyme is placed as a coating on the membrane which slowly destabilizes the liposome. Since control of drug release depends on the concentration of enzyme initially placed in the membrane, there is no real effective way to modulate or alter drug release to achieve "on demand" drug delivery. The same problem exists for pH-sensitive liposomes in that as soon as the liposome vesicle comes into contact with a target cell, it will be engulfed and a drop in pH will lead to drug release.

This liposome delivery system can also be made to accumulate at a target organ, tissue, or cell via active targeting by incorporating an antibody or hormone on the surface of the liposomal vehicle). This can be achieved according to known methods.

Different types of liposomes can be prepared according to Bangham et al., 1965, J Mol Biol, 13:238-252; U.S. Pat. No. 5,653,996 to Hsu et al.; U.S. Pat. No. 5,643,599 to Lee et al.; U.S. Pat. No. 5,885,613 to Holland et al.; U.S. Pat. No. 5,631,237 to Dzau et al.; and U.S. Pat. No. 5,059,421 to Loughrey et al., as well as any other approach demonstrated in the art.

From the foregoing, it should be apparent that the polypeptide or polypeptide monobody can either be delivered in a liposome or, when incorporated into the lipid bilayer(s), used as a means for targeting a liposome to cells.

An alternative approach for delivery of a polypeptide monobody involves the conjugation of the desired polypeptide or polypeptide monobody to a polymer that is stabilized to avoid enzymatic degradation of the conjugated polypeptide or polypeptide monobody. Conjugated proteins or polypeptides of this type are described in U.S. Pat. No. 5,681,811 to Ekwuribe.

When it is desirable to achieve heterologous expression of a desirable polypeptide or polypeptide monobody of the present invention in a target cell, DNA molecules encoding the polypeptide or polypeptide monobody can be delivered into the cell. Basically, this includes providing a nucleic acid molecule encoding the polypeptide or polypeptide monobody and then introducing the nucleic acid molecule into the cell under conditions effective to express the polypeptide monobody in the cell. Preferably, this is achieved by inserting the nucleic acid molecule into an expression vector before it is introduced into the cell. For intracellular expression in this manner, use of a polypeptide monobody is preferred because such monobodies are enzymatically stable within cells.

When transforming mammalian cells for heterologous expression of a polypeptide or polypeptide monobody of the present invention, an adenovirus vector can be employed. Adenovirus gene delivery vehicles can be readily prepared and utilized given the disclosure provided in Berkner, 1988, Biotechniques, 6(7):616-629 and Rosenfeld et al., 1991, Science, 252(5004):431-434.

Adeno-associated viral gene delivery vehicles can be constructed and used to deliver a gene to cells. The use of adeno-associated viral gene delivery vehicles in vivo is described in Flotte et al., 1993, Proc Natl Acad Sci USA., 90(22):10613-10617 and Kaplitt et al., 1994, Nat Genet., 8:148-154. Additional types of adenovirus vectors are described in U.S. Pat. No. 6,057,155 to Wickham et al.; U.S. Pat. No. 6,033,908 to Bout et al.; U.S. Pat. No. 6,001,557 to Wilson et al.; U.S. Pat. No. 5,994,132 to Chamberlain et al.; U.S. Pat. No. 5,981,225 to Kochanek et al.; U.S. Pat. No. 5,885,808 to Spooner et al.; and U.S. Pat. No. 5,871,727 to Curiel.

Retroviral vectors which have been modified to form infective transformation systems can also be used to deliver nucleic acid encoding a desired polypeptide monobody into a target cell. One such type of retroviral vector is disclosed in U.S. Pat. No. 5,849,586 to Kriegler et al.

Regardless of the type of infective transformation system employed, it should be targeted for delivery of the nucleic acid to a specific cell type. For example, for delivery of the nucleic acid into tumor cells, a high titer of the infective transformation system can be injected directly within the tumor site so as to enhance the likelihood of tumor cell infection. The infected cells will then express the desired polypeptide or polypeptide monobody, allowing the polypeptide or polypeptide monobody to bind to apo RAS.

Whether a polypeptide or polypeptide monobody of the present invention (or encoding nucleic acids) is administered alone or in combination with pharmaceutically or physiologically acceptable carriers, excipients, or stabilizers, or in solid or liquid form such as, tablets, capsules, powders, solutions, suspensions, or emulsions, they can be administered orally, parenterally, subcutaneously, intravenously, intramuscularly, intraperitoneally, by intranasal instillation, by intracavitary or intravesical instillation, intraocularly, intraarterially, intralesionally, or by application to mucous membranes, such as, that of the nose, throat, and bronchial tubes. For most therapeutic purposes, a polypeptide or polypeptide monobody (or an encoding nucleic acid) can be administered intravenously.

For injectable dosages, solutions or suspensions of these materials can be prepared in a physiologically acceptable diluent with a pharmaceutical carrier. Such carriers include sterile liquids, such as water and oils, with or without the addition of a surfactant and other pharmaceutically and physiologically acceptable carrier, including adjuvants, excipients or stabilizers. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions.

For use as aerosols, a polypeptide monobody or nucleic acid in solution or suspension may be packaged in a pressurized aerosol container together with suitable propellants, for example, hydrocarbon propellants like propane, butane, or isobutane with conventional adjuvants. The materials of the present invention also may be administered in a nonpressurized form such as in a nebulizer or atomizer.

Dosages to be administered can be determined according to known procedures, including those which balance both drug efficacy and degree of side effects.

From the foregoing, it should be appreciated that therapeutic methods and compositions are contemplated for detecting and inhibiting RAS. These methods are useful to inhibit RAS mediated signaling find application in a wide variety of cell types, tissues and systems where RAS signaling is not desired. Thus, in general, the invention contemplates a method for inhibiting RAS signaling by contacting RAS with an inhibiting amount of an apo RAS binding polypeptide or polypeptide monobody (or fusion protein/conjugate containing them) of the present invention.

An inhibiting amount of apo RAS binding molecule is an amount sufficient to produce the desired result, namely to inhibit RAS signaling to a degree sufficient to reduce signaling of at least one of the mitogen-activated protein kinases (MAPK) and phosphoinositide-3 kinase (PI3K) pathways.

In one embodiment, an inhibiting amount of apo RAS binding molecule is an amount sufficient to reduce RAS pathway signaling by at least 1.1 fold, 1.2 fold, 1.3 fold, 1.4 fold, 1.5 fold, 1.6 fold, 1.7 fold, 1.8 fold, 1.9 fold, 2.0 fold, 2.5 fold, 3.0 fold, 3.5 fold, 4.0 fold, 4.5 fold, 5.0 fold, 10 fold, 15 fold, 20 fold, 30 fold, 40 fold 50 fold, 100 fold, 150 fold, 200 fold, 300 fold, 400 fold, 500 fold, 1000 fold, or greater than 1000 fold.

The apo RAS binding molecule may be combined with other pharmaceutical compositions and/or excipients. For example, an apo RAS binding molecule may be co-administered or added to established anti-cancer chemotherapeutic regimens.

Combination Therapy

The apo RAS binding molecule of the invention (e.g. an apo RAS monobody) can be used alone or in combination with another therapeutic treatment or agent to treat a disease or disorder. For example, the apo RAS binding molecule may be administered alone, or in combination with one or more therapeutically effective agents or treatments. The other therapeutically effective agent may be conjugated to the apo RAS binding molecule, incorporated into the same composition as the apo RAS binding molecule, or may be administered as a separate composition. The other therapeutically agent or treatment may be administered prior to, during and/or after the administration of the apo RAS binding molecule or related compound.

In certain embodiments, the apo RAS binding molecule of the invention is co-administered with one or more other therapeutic agents or treatments. In other embodiments, the apo RAS binding molecule administered independently from the administration of one or more other therapeutic agents or treatments. For example, the apo RAS binding molecule of the invention is administered first, followed by the administration of one or more other therapeutic agents or treatments. Alternatively, one or more other therapeutic agents are administered first, followed by the administration of an apo RAS binding molecule. As another example, a treatment (e.g, a surgery, radiation, etc.) is carried out first, followed by the administration of the apo RAS binding molecule.

Other therapeutically effective agents/treatments include surgery, anti-neoplastics (including chemotherapeutic agents and radiation), anti-angiogenesis agents, antibodies to other targets, small molecules, photodynamic therapy, immunotherapy, immunity enhancing therapy, cytotoxic agents, cytokines, chemokines, growth inhibitory agents, anti-hormonal agents, kinase inhibitors, cardioprotectants, immunostimulatory agents, immunosuppressive agents, and agents that promote proliferation of hematological cells.

In one embodiment, the "another therapeutic agent," as used herein, are second, distinct therapeutic agents or anti-cancer agents, i.e., therapeutic agents or anti-cancer agents "other than" the apo RAS binding molecule of the invention. Any secondary therapeutic agent may be used in the combination therapies of the present invention. Also, secondary therapeutic agents or "second anti-cancer agents" may be selected with a view to achieving additive, greater than additive and potentially synergistic effects, according to the following guidance.

To practice combined anti-tumor therapy, one would administer to a subject an apo RAS binding molecule in combination with another, i.e., a second, distinct anti-cancer agent in a manner effective to result in their combined anti-tumor actions within subject. The agents would therefore be provided in amounts effective and for periods of time effective to result in their combined, or concurrent, presence within the tumor or tumor vasculature and their combined actions in the tumor environment. To achieve this goal, the apo RAS binding molecule and the second, distinct anti-cancer agents may be administered to the animal substantially simultaneously, either in a single composition, or as two distinct compositions using different administration routes.

Alternatively, administration of the apo RAS binding molecule may precede, or follow, the second, distinct anticancer agent by, e.g., intervals ranging from minutes to weeks. In certain embodiments where the apo RAS binding molecule and the second, distinct anti-cancer agents are applied separately to the animal, one would ensure that a significant period of time did not expire between the time of each delivery, such that each agent would still be able to exert an advantageously combined effect on the tumor. In such instances, it is contemplated that one would contact the tumor with both agents within about 5 minutes to about one week of each other and, more preferably, within about 12-72 hours of each other, with a delay time of only about 12-48 hours being most preferred.

The secondary therapeutic agents for separately timed combination therapies may be selected based upon certain criteria, including those discussed elsewhere herein. However, a preference for selecting one or more second, distinct anti-cancer agents for prior or subsequent administration does not preclude their use in substantially simultaneous administration if desired. Second, distinct anti-cancer agents selected for administration "prior to" the primary therapeutic agents of the present invention, and designed to achieve increased and potentially synergistic effects.

Second, distinct anti-cancer agents selected for administration "subsequent to" the primary therapeutic agents of the present invention, and designed to achieve increased and potentially synergistic effects, include agents that benefit from the effects of the primary therapeutic agent. Accordingly, effective second, distinct anti-cancer agents for subsequent administration include anti-angiogenic agents, which inhibit metastasis; agents targeting necrotic tumor cells, such as antibodies specific for intracellular binding partner molecules that become accessible from malignant cells in vivo (U.S. Pat. Nos. 5,019,368, 4,861,581 and 5,882,626, each specifically incorporated herein by reference); chemotherapeutic agents; and anti-tumor cell immunoconjugates, which attack any tumor cells.

The apo RAS binding molecule can also be administered in combination with a cancer immunotherapy. The cancer immunotherapy can be one designed to elicit a humoral immune response against the subject's cancer cells, or a cell-mediated immune response against the subject's cancer cells, or a combination of a humoral response and a cell-response against the subject's cancer cells. Non-limiting examples of cancer immunotherapy useful in combination with the apo RAS binding molecule include a cancer vaccine, a DNA cancer vaccine, adoptive cellular therapy, adoptive immunotherapy, CAR T-cell therapy, antibodies, immunity enhancing compounds, cytokines, interleukins (e.g., IL-2, etc.), interferons (IFN-α, etc.), and checkpoint inhibitors (e.g., PD-1 inhibitor, CTLA-4 inhibitor, etc.).

In some situations, it may be desirable to extend the time period for treatment significantly, where several days (2, 3, 4, 5, 6 or 7), several weeks (1, 2, 3, 4, 5, 6, 7 or 8) or even several months (1, 2, 3, 4, 5, 6, 7 or 8) lapse between the respective administrations. This would be advantageous in circumstances where one treatment was intended to substantially destroy the tumor, such as the primary therapeutic agent of the present invention, and another treatment was intended to prevent micrometastasis or tumor re-growth, such as the administration of an anti-angiogenic agent. Anti-angiogenics should be administered at a careful time after surgery, however, to allow effective wound healing. Anti-angiogenic agents may then be administered for the lifetime of the patient.

It is also envisioned that, in some instances, more than one administration of either the apo RAS binding molecule of the invention or the second, distinct anti-cancer agent will be utilized. The apo RAS binding molecule and the second, distinct anti-cancer agent may be administered interchangeably, on alternate days or weeks; or a sequence of one agent treatment may be given, followed by a sequence of the other treatment. In any event, to achieve tumor regression using a combined therapy, all that is required is to deliver both agents in a combined amount effective to exert an anti-tumor effect, irrespective of the times for administration.

Chemotherapeutic drugs can be used in combination with the apo RAS binding molecule. Chemotherapeutic drugs can kill proliferating tumor cells, enhancing the necrotic areas created by the overall treatment.

One aspect of the invention provides a method of treating or preventing cancer using an apo RAS binding molecule of the invention. In one embodiment, the cancer is associated with increased levels of Ras signaling. In one embodiment, the cancer is associated with increased levels of mitogen-activated protein kinases (MAPK) and/or phosphoinositide-3 kinase (PI3K) signaling. The skilled artisan will understand that treating or preventing cancer in a patient includes, by way of non-limiting examples, killing and destroying a cancer cell, as well as reducing the proliferation of or cell division rate of a cancer cell. The skilled artisan will also understand that a cancer cell can be, by way of non-limiting examples, a primary cancer cell, a cancer stem cell, a metastatic cancer cell. The following are non-limiting examples of cancers that can be treated by the disclosed methods and compositions: Acute Lymphoblastic; Acute Myeloid Leukemia; Adrenocortical Carcinoma; Adrenocortical Carcinoma, Childhood; Appendix Cancer; Basal Cell Carcinoma; Bile Duct Cancer, Extrahepatic; Bladder Cancer; Bone Cancer; Osteosarcoma and Malignant Fibrous Histiocytoma; Brain Stem Glioma, Childhood; Brain Tumor, Adult; Brain Tumor, Brain Stem Glioma, Childhood; Brain Tumor, Central Nervous System Atypical Teratoid/Rhabdoid Tumor, Childhood; Central Nervous System Embryonal Tumors; Cerebellar Astrocytoma; Cerebral Astrocytotna/Malignant Glioma; Craniopharyngioma; Ependymoblastoma; Ependymoma; Medulloblastoma; Medulloepithelioma; Pineal Parenchymal Tumors of intermediate Differentiation; Supratentorial Primitive Neuroectodermal Tumors and Pineoblastoma; Visual Pathway and Hypothalamic Glioma; Brain and Spinal Cord Tumors; Breast Cancer; Bronchial Tumors; Burkitt Lymphoma; Carcinoid Tumor; Carcinoid Tumor, Gastrointestinal; Central Nervous System Atypical Teratoid/Rhabdoid Tumor; Central Nervous System Embryonal Tumors; Central Nervous System Lymphoma; Cerebellar Astrocytoma Cerebral Astrocytoma/Malignant Glioma, Childhood; Cervical Cancer; Chordoma, Childhood; Chronic Lymphocytic Leukemia; Chronic Myelogenous Leukemia; Chronic Myeloproliferative Disorders; Colon Cancer; Colorectal Cancer; Craniopharyngioma; Cutaneous T-Cell Lymphoma; Esophageal Cancer; Ewing Family of Tumors; Extragonadal Germ Cell Tumor; Extrahepatic Bile Duct Cancer; Eye Cancer, intraocular Melanoma; Eye Cancer, Retinoblastoma; Gallbladder Cancer; Gastric (Stomach) Cancer; Gastrointestinal Carcinoid Tumor; Gastrointestinal Stromal Tumor (GIST); Germ Cell Tumor, Extracranial; Germ Cell Tumor, Extragonadal; Germ Cell Tumor, Ovarian; Gestational Trophoblastic Tumor; Glioma; Glioma, Childhood Brain Stem; Glioma, Childhood Cerebral Astrocytoma; Glioma, Childhood Visual Pathway and Hypothalamic; Hairy Cell Leukemia; Head and Neck Cancer; Hepatocellular (Liver) Cancer; Histiocytosis, Langerhans Cell; Hodgkin Lymphoma; Hypopharyngeal Cancer; Hypothalamic and Visual Pathway Glioma; intraocular Melanoma; Islet Cell Tumors; Kidney (Renal Cell) Cancer; Langerhans Cell Histiocytosis; Laryngeal Cancer; Leukemia, Acute Lymphoblastic; Leukemia, Acute Myeloid; Leukemia, Chronic Lymphocytic; Leukemia, Chronic Myelogenous; Leukemia, Hairy Cell; Lip and Oral Cavity Cancer; Liver Cancer; Lung Cancer, Non-Small Cell; Lung Cancer, Small Cell; Lymphoma, AIDS-Related; Lymphoma, Burkitt; Lymphoma, Cutaneous T-Cell; Lymphoma, Hodgkin; Lymphoma, Non-Hodgkin; Lymphoma, Primary Central Nervous System; Macroglobulinemia, Waldenstrom; Malignant Fibrous Histiocvtoma of Bone and Osteosarcoma; Medulloblastoma; Melanoma; Melanoma, intraocular (Eye); Merkel Cell Carcinoma; Mesothelioma; Metastatic Squamous Neck Cancer with Occult Primary; Mouth Cancer; Multiple Endocrine Neoplasia Syndrome, (Childhood); Multiple Myeloma/Plasma Cell Neoplasm; Mycosis; Fungoides; Myelodysplastic Syndromes; Myelodysplastic/Myeloproliferative Diseases; Myelogenous Leukemia, Chronic; Myeloid Leukemia, Adult Acute; Myeloid Leukemia, Childhood Acute; Myeloma, Multiple; Myeloproliferative Disorders, Chronic; Nasal Cavity and Paranasal Sinus Cancer; Nasopharyngeal Cancer; Neuroblastoma; Non-Small Cell Lung Cancer; Oral Cancer; Oral Cavity Cancer; Oropharyngeal Cancer; Osteosarcoma and Malignant Fibrous Histiocytoma of Bone; Ovarian Cancer; Ovarian Epithelial Cancer; Ovarian Germ Cell Tumor; Ovarian Low Malignant Potential Tumor; Pancreatic Cancer; Pancreatic Cancer, Islet Cell Tumors; Papillomatosis; Parathyroid Cancer; Penile Cancer; Pharyngeal Cancer; Pheochromocytoma; Paraganglioma; Pineal Parenchymal Tumors of Intermediate Differentiation; Pineoblastoma and Supratentorial Primitive Neuroectodermal Tumors; Pituitary Tumor; Plasma Celt Neoplasm/Multiple Myeloma; Pleuropulmonary Blastoma; Primary Central Nervous System Lymphoma; Prostate Cancer; Rectal Cancer; Renal Cell (Kidney) Cancer; Renal Pelvis and Ureter, Transitional Cell Cancer; Respiratory Tract Carcinoma Involving the NUT Gene on Chromosome 15; Retinoblastoma; Rhabdomyosarcoma; Salivary Gland Cancer; Sarcoma, Ewing Family of Tumors; Sarcoma, Kaposi; Sarcoma, Soft Tissue; Sarcoma, Uterine; Sezary Syndrome; Skin Cancer (Nonmelanoma); Skin Cancer (Melanoma); Skin Carcinoma, Merkel Cell; Small Cell Lung Cancer; Small Intestine Cancer; Soft Tissue Sarcoma; Squamous Cell Carcinoma, Squamous Neck Cancer with Occult Primary, Metastatic; Stomach (Gastric) Cancer; Supratentorial Primitive Neuroectodermal Tumors; T-Cell Lymphoma, Cutaneous; Testicular Cancer; Throat Cancer; Thymoma and Thymic Carcinoma; Thyroid Cancer; Transitional Cell Cancer of the Renal Pelvis and Ureter; Trophoblastic Tumor, Gestational; Urethral Cancer; Uterine Cancer, Endometrial; Uterine Sarcoma; Vaginal Cancer; Vulvar Cancer; Waldenstrom Macroglobulinemia; and Wilms Tumor.

In one embodiment, the invention provides a method to treat cancer comprising treating the subject prior to, concurrently with, or subsequently to the administration of the apo RAS binding molecule, with a complementary therapy for the cancer, such as surgery, chemotherapy, chemotherapeutic agent, radiation therapy, or hormonal therapy or a combination thereof.

Chemotherapeutic agents include cytotoxic agents (e.g., 5-fluorouracil, cisplatin, carboplatin, methotrexate, daunorubicin, doxorubicin, vincristine, vinblastine, oxorubicin, carmustine (BCNU), lomustine (CCNU), cytarabine USP, cyclophosphamide, estramucine phosphate sodium, altretamine, hydroxyurea, ifosfamide, procarbazine, mitomycin, busulfan, cyclophosphamide, mitoxantrone, carboplatin, cisplatin, interferon alfa-2a recombinant, paclitaxel, teniposide, and streptozoci), cytotoxic alkylating agents (e.g., busulfan, chlorambucil, cyclophosphamide, melphalan, or ethylesulfonic acid), alkylating agents (e.g., asaley, AZQ, BCNU, busulfan, bisulphan, carboxyphthalatoplatinum, CBDCA, CCNU, CHIP, chlorambucil, chlorozotocin, cisplatinum, clomesone, cyanomorpholinodoxorubicin, cyclodisone, cyclophosphamide, dianhydrogalactitol, fluorodopan, hepsulfam, hycanthone, iphosphamide, melphalan, methyl CCNU, mitomycin C, mitozolamide, nitrogen mustard, PCNU, piperazine, piperazinedione, pipobroman, porfiromycin, spirohydantoin mustard, streptozotocin, teroxirone, tetraplatin, thiotepa, triethylenemelamine, uracil nitrogen mustard, and Yoshi-864), antimitotic agents (e.g., allocolchicine, Halichondrin M, colchicine, colchicine derivatives, dolastatin 10, maytansine, rhizoxin, paclitaxel derivatives, paclitaxel, thiocolchicine, trityl cysteine, vinblastine sulfate, and vincristine sulfate), plant alkaloids (e.g., actinomycin D, bleomycin, L-asparaginase, idarubicin, vinblastine sulfate, vincristine sulfate, mitramycin, mitomycin, daunorubicin, VP-16-213, VM-26, navelbine and taxotere), biologicals (e.g., alpha interferon, BCG, G-CSF, GM-CSF, and interleukin-2), topoisomerase I inhibitors (e.g., camptothecin, camptothecin derivatives, and morpholinodoxorubicin), topoisomerase II inhibitors (e.g., mitoxantron, amonafide, m-AMSA, anthrapyrazole derivatives, pyrazoloacridine, bisantrene HCL, daunorubicin, deoxydoxorubicin, menogaril, N,N-dibenzyl daunomycin, oxanthrazole, rubidazone, VM-26 and VP-16), and synthetics (e.g., hydroxyurea, procarbazine, o,p'-DDD, dacarbazine, CCNU, BCNU, cis-diamminedichloroplatimun, mitoxantrone, CBDCA, levamisole, hexamethylmelamine, all-trans retinoic acid, gliadel and porfimer sodium).

Antiproliferative agents are compounds that decrease the proliferation of cells. Antiproliferative agents include alkylating agents, antimetabolites, enzymes, biological response modifiers, miscellaneous agents, hormones and antagonists, androgen inhibitors (e.g., flutamide and leuprolide acetate), antiestrogens (e.g., tamoxifen citrate and analogs thereof, toremifene, droloxifene and roloxifene), Additional examples of specific antiproliferative agents include, but are not limited to levamisole, gallium nitrate, granisetron, sargramostim strontium-89 chloride, filgrastim, pilocarpine, dexrazoxane, and ondansetron.

The apo RAS binding molecule can be administered alone or in combination with other anti-tumor agents, including cytotoxic/antineoplastic agents and anti-angiogenic agents. Cytotoxic/anti-neoplastic agents are defined as agents which attack and kill cancer cells. Some cytotoxic/anti-neoplastic agents are alkylating agents, which alkylate the genetic material in tumor cells, e.g., cis-platin, cyclophosphamide, nitrogen mustard, trimethylene thiophosphoramide, carmustine, busulfan, chlorambucil, belustine, uracil mustard, chlomaphazin, and dacabazine. Other cytotoxic/anti-neoplastic agents are antimetabolites for tumor cells, e.g., cytosine arabinoside, fluorouracil, methotrexate, mercaptopuirine, azathioprime, and procarbazine. Other cytotoxic/anti-neoplastic agents are antibiotics, e.g., doxorubicin, bleomycin, dactinomycin, daunorubicin, mithramycin, mitomycin, mytomycin C, and daunomycin. There are numerous liposomal formulations commercially available for these compounds. Still other cytotoxic/anti-neoplastic agents are mitotic inhibitors (vinca alkaloids). These include vincristine, vinblastine and etoposide. Miscellaneous cytotoxic/anti-neoplastic agents include taxol and its derivatives, L-asparaginase, anti-tumor antibodies, dacarbazine, azacytidine, amsacrine, melphalan, VM-26, ifosfamide, mitoxantrone, and vindesine.

Anti-angiogenic agents are well known to those of skill in the art. Suitable anti-angiogenic agents for use in the methods and compositions of the present disclosure include anti-VEGF antibodies, including humanized and chimeric antibodies, anti-VEGF aptamers and antisense oligonucleotides. Other known inhibitors of angiogenesis include angiostatin, endostatin, interferons, interleukin 1 (including alpha and beta) interleukin 12, retinoic acid, and tissue inhibitors of metalloproteinase-1 and -2. (TIMP-1 and -2). Small molecules, including topoisomerases such as razoxane, a topoisomerase II inhibitor with anti-angiogenic activity, can also be used.

Other anti-cancer agents that can be used in combination with the disclosed compounds include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; albumin-bound paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur;

teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine; vinorelbine tartrate; vinrosidine sulfate; vinzolidine sulfate; vorozole; zeniplatin; zinostatin; zorubicin hydrochloride. Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; beta-clamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole;

linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RH retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stemcell division inhibitors; stipiamide; stromely sin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors;

ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; imilimumab; mirtazapine; BrUOG 278; BrUOG 292; RAD0001; CT-011; folfirinox; tipifarnib; R115777; LDE225; calcitriol; AZD6244; AMG 655; AMG 479; BKM120; mFOLFOX6; NC-6004; cetuximab; IM-C225; LGX818; MEK162; BBI608; MEDI4736; vemurafenib; ipilimumab; ivolumab; nivolumab; panobinostat; leflunomide; CEP-32496; alemtuzumab; bevacizumab; ofatumumab; panitumumab; pembrolizumab; rituximab; trastuzumab; STAT3 inhibitors (e.g., STA-21, LLL-3, LLL12, XZH-5, S31-201, SF-1066, SF-1087, STX-0119, cryptotanshinone, curcumin, diferuloylmethane, FLLL11, FLLL12, FLLL32, FLLL62, C3, C30, C188, C188-9, LY5, OPB-31121, pyrimethamine, OPB-51602, AZD9150, etc.); hypoxia inducing factor 1 (HIF-1) inhibitors (e.g., LW6, digoxin, laurenditerpenol, PX-478, RX-0047, vitexin, KC7F2, YC-1, etc.) and zinostatin stimalamer. In one embodiment, the anti-cancer drug is 5-fluorouracil, taxol, or leucovorin.

Methods of Diagnosis

In some embodiments, an increase in the level of the nucleotide free state of RAS (apo RAS) in a subject's cell, tissue, or bodily fluid, compared with a comparator is used in the methods of the invention as marker for the diagnosis of a disease or disorder, assessing the severity of a disease or disorder, and for monitoring the effect or effectiveness of a treatment of a disease or disorder. In various embodiments, the disease or disorder is cancer associated with an increased level of Ras signaling.

In one embodiment, the invention is a method of diagnosing a disease or disorder of a subject by assessing the level of apo RAS, in a biological sample of the subject. In one embodiment, the biological sample of the subject is a cell, tissue, or bodily fluid. Non-limiting examples of bodily fluids in which the level of apo RAS, can be assessed include, but are not limited to, blood, serum, plasma and urine. In various embodiments, the level of apo RAS, in the biological sample of the subject is compared with the apo RAS level in a comparator. Non-limiting examples of comparators include, but are not limited to, a negative control, a positive control, an expected normal background value of the subject, a historical normal background value of the subject, an expected normal background value of a population that the subject is a member of, or a historical normal background value of a population that the subject is a member of. In various embodiments, the disease or disorder is associated with an increased level of Ras signaling (e.g., cancers, RASopathies and mental disorders.) In some embodiments, the method of diagnosing includes a further step of treating the patient for the diagnosed disease or disorder.

In another embodiment, the invention is a method of assessing the severity of a disease or disorder of a subject by assessing the level of apo RAS in a biological sample of the subject. In one embodiment, the biological sample of the subject is a cell, tissue, or bodily fluid. Non-limiting examples of bodily fluids in which the level of apo RAS can be assessed include, but are not limited to, blood, serum, plasma and urine. In various embodiments, the level of apo RAS in the biological sample of the subject is compared with the apo RAS level in a comparator. Non-limiting examples of comparators include, but are not limited to, a negative control, a positive control, an expected normal background value of the subject, a historical normal background value of the subject, an expected normal background value of a population that the subject is a member of, or a historical normal background value of a population that the subject is a member of. In various embodiments, the disease or disorder is cancer associated with an increased level of Ras signaling (e.g., cancers, RASopathies and mental disorders.) In some embodiments, the method of assessing the severity includes a further step of treating the patient for the disease or disorder.

In another embodiment, the invention is a method of monitoring the effect of a treatment of a disease or disorder of a subject by assessing the level of apo RAS in a biological sample of the subject. In one embodiment, the biological sample of the subject is a cell, tissue, or bodily fluid. Non-limiting examples of bodily fluids in which the level of apo RAS can be assessed include, but are not limited to, blood, serum, plasma and urine. In various embodiments, the level of apo RAS in the biological sample of the subject is compared with apo RAS level in a comparator. Non-limiting examples of comparators include, but are not limited to, a negative control, a positive control, an expected normal background value of the subject, a historical normal background value of the subject, an expected normal background value of a population that the subject is a member of, or a historical normal background value of a population that the subject is a member of. In various embodiments, the disease or disorder is cancer associated with an increased level of Ras signaling (e.g., cancers, RASopathies and mental disorders.) In some embodiments, the method of monitoring the effect of a treatment includes a further step of treating the patient for the disease or disorder.

In various embodiments, the subject is a human subject, and may be of any race, sex and age. Representative subjects include those who are suspected of having experienced a disease or disorder, those who have been diagnosed as having experienced a disease or disorder, those who have been diagnosed as having a disease or disorder, and those who are at risk of developing a disease or disorder.

Information obtained from the methods of the invention described herein can be used alone, or in combination with other information (e.g., disease status, disease history, vital signs, blood chemistry, etc.) from the subject or from the biological sample obtained from the subject.

In the diagnostic methods of the invention, a biological sample obtained from a subject is assessed for the level of apo RAS contained therein.

In other various embodiments of the methods of the invention, the level of apo RAS is determined to be increased when the apo RAS is increased by at least 10%, by at least 20%, by at least 30%, by at least 40%, by at least 50%, by at least 60%, by at least 70%, by at least 80%, by at least 90%, by at least 100%, by at least 200%, by at least 300%, by at least 400%, by at least 500%, by at least 600%, by at least 700%, by at least 800%, by at least 900%, by at least 1000%, when compared to with a comparator control In other various embodiments of the methods of the invention, the level of apo RAS is determined to be decreased when the apo RAS is decreased by at least 10%, by at least 20%, by at least 30%, by at least 40%, by at least 50%, by at least 60%, by at least 70%, by at least 80%, by at least 90%, by at least 100%, by at least 200%, by at least 300%, by at least 400%, by at least 500%, by at least 600%, by at least 700%, by at least 800%, by at least 900%, by at least 1000%, when compared to with a comparator control.

In various embodiments, an increased or decreased level of apo RAS is indicative of a disease or disorder. In various embodiments, the disease or disorder is cancer.

In the methods of the invention, a biological sample from a subject is assessed for the level of apo RAS in the biological sample obtained from the patient. The level of apo RAS in the biological sample can be determined by assessing the amount of apo RAS in the biological sample. In some embodiments, the level of apo RAS in the biological sample is determined in an assay using at least one apo RAS binding molecule (e.g. at least one apo RAS monobody) of the invention described elsewhere herein.

In various embodiments, methods of measuring apo RAS levels in a biological sample obtained from a patient include, but are not limited to, an immunochromatography assay, an immunodot assay, a Luminex assay, an ELISA assay, an ELISPOT assay, a protein microarray assay, a Western blot assay, a mass spectrophotometry assay, a radioimmunoassay (MA), a radioimmunodiffusion assay, a liquid chromatography-tandem mass spectrometry assay, an ouchterlony immunodiffusion assay, reverse phase protein microarray, a rocket immunoelectrophoresis assay, an immunohistostaining assay, an immunoprecipitation assay, a complement fixation assay, FACS, an enzyme-substrate binding assay, an enzymatic assay, an enzymatic assay employing a detectable molecule, such as a chromophore, fluorophore, or radioactive substrate, a substrate binding assay employing such a substrate, a substrate displacement assay employing such a substrate, and a protein chip assay (see also, 2007, Van Emon, Immunoassay and Other Bioanalytical Techniques, CRC Press; 2005, Wild, Immunoassay Handbook, Gulf Professional Publishing; 1996, Diamandis and Christopoulos, Immunoassay, Academic Press; 2005, Joos, Microarrays in Clinical Diagnosis, Humana Press; 2005, Hamdan and Righetti, Proteomics Today, John Wiley and Sons; 2007). In some embodiments, the level of apo RAS in the biological sample is measured with an assay that uses at least one R15 monobody of the invention that are described elsewhere herein.

Screening

In one aspect, the present invention is directed to a method for identifying compounds that regulate Ras signaling. The present invention is based, in part, as described elsewhere herein, on the use of an apo RAS binding molecule (e.g. apo RAS monobody) in assays identifying compositions that modulate Ras signaling. In one embodiment, the method is useful for identifying Ras inhibitors or compositions that decrease Ras signaling.

In one embodiment, the method is useful for identifying compositions that treat a disease or disorder is associated with abnormal Ras activity (e.g., increased levels of apo RAS).

In one embodiment, the method comprises contacting a test composition with a sample; detecting the level of apo RAS, and identifying a modulator of Ras signaling. In one embodiment, the modulator of Ras signaling is an inhibitor of Ras signaling. In one embodiment, the inhibitor of Ras signaling decreases at least one of Ras signaling, MAPK signaling and PI3K signaling, or another target downstream of RAS. In one embodiment, the inhibitor of Ras signaling is useful for treating a disease or disorder associated with increased levels of Ras signaling.

In one embodiment, the modulator of Ras signaling is an activator of Ras signaling. In one embodiment, the activator of Ras signaling increases at least one of Ras signaling, MAPK signaling and PI3K signaling, or another target downstream of RAS. In one embodiment, the activator of Ras signaling is useful for treating a disease or disorder associated with decreased levels of Ras signaling.

In one embodiment, the screening method of the present invention is an in vitro assay. For example, in one embodiment, the method comprises contacting at least one Ras polypeptide with a test compound and detecting the level of apo RAS using an apo RAS binding molecule of the invention.

In one embodiment, the screening method of the present invention is a cell-based assay. For example, in one embodiment the method comprises contacting a cell with a test composition and detecting the level of apo RAS using an apo RAS binding molecule. The cell may be cultured with the test composition for a defined time period prior to determining activity or expression. For example, in certain embodiments, the cell may be cultured with the test composition for about 1 second, 5 seconds, 10 seconds, 30 seconds, 1 minute, 2 minutes, 5 minutes, 10 minutes, 30 minutes, 1 hour, 2 hours, 6 hours, 12 hours, 24 hours, 3 days, 7 days, 2 weeks, 1 month, 3 months, or longer. It can be determined if the test composition alters the level of apo RAS as compared to a similar cell which is not cultured with the test composition. Aside from the particular composition or condition being screened, the cell may be cultured using any standard culture conditions or cell culture media known in the art.

Any suitable cell may be used for the cell-based assay including, but not limited to, prokaryotic cells, eukaryotic cells, and mammalian cells. In one embodiment, the cell is a cell that expresses Ras. In one embodiment, the cell is modified to express at least one variant Ras allele. In one embodiment, the cell-based assay comprises one or more cells derived from a cell line including, but not limited to, HEK 293T, CHO, BHK, VERO, HeLa, COS, MDCK, NS0 and W138. In one embodiment, the cell based assay comprises one or more primary cells isolated from a subject (e.g. a mammal). For example, in one embodiment, the assay comprises the use of a tumor cell isolated from a subject. In one embodiment, the cell based screen comprises an in vivo screening assay, wherein the recombinant protein is introduced into one or more cells in animal. In some embodiments, a cell based assay is used as a secondary screen on test compounds identified as modulators of Ras signaling in an in vitro screening assay.

In certain embodiments, the method is a high throughput method, where a plurality of test compositions or conditions are screened. For example, in certain embodiments, a library of compositions is screened, where each composition of the library is individually contacted to a sample in order to identify which compositions modulate or do not modulate the Ras signaling.

The test compounds can be obtained using any of the numerous approaches in combinatorial-library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam et al., 1997, Anticancer Drug Des. 12:45).

Examples of methods for the synthesis of molecular libraries can be found in the art, for example, in: DeWitt et al., 1993, Proc. Natl. Acad. USA 90:6909; Erb et al., 1994, Proc. Natl. Acad. Sci. USA 91:11422; Zuckermann et al., 1994, J. Med. Chem. 37:2678; Cho et al., 1993, Science 261:1303; Carrell et al., 1994, Angew. Chem. Int. Ed. Engl. 33:2059; Carell et al., 1994, Angew. Chem. Int. Ed. Engl. 33:2061; and Gallop et al., 1994, J. Med. Chem. 37:1233.

Libraries of compounds may be presented in solution (e.g., Houghten, 1992, Biotechniques 13:412-421), or on beads (Lam, 1991, Nature 354:82-84), chips (Fodor, 1993, Nature 364:555-556), bacteria (Ladner U.S. Pat. No. 5,223,409), spores (Ladner U.S. Pat. No. '409), plasmids (Cull et al., 1992, Proc. Natl. Acad. Sci. USA 89:1865-1869) or on phage (Scott and Smith, 1990, Science 249:386-390; Devlin, 1990, Science 249:404-406; Cwirla et al., 1990, Proc. Natl. Acad. Sci. USA 87:6378-6382; Felici, 1991, J. Mol. Biol. 222:301-310; and Ladner supra).

In situations where "high-throughput" modalities are preferred, it is typical that new chemical entities with useful properties are generated by identifying a chemical compound (called a "lead compound") with some desirable property or activity, creating variants of the lead compound, and evaluating the property and activity of those variant compounds. The current trend is to shorten the time scale for all aspects of drug discovery.

In one embodiment, high throughput screening methods involve providing a library containing a large number of compounds (candidate compounds) potentially having the desired activity. Such "combinatorial chemical libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

Kits

The invention also includes a kit comprising an apo RAS binding molecule of the invention and an instructional material which describes, for instance, administering the apo RAS binding molecule to an individual as a therapeutic treatment or a non-treatment use as described elsewhere herein. In an embodiment, this kit further comprises a (preferably sterile) pharmaceutically acceptable carrier suitable for dissolving or suspending the therapeutic composition, comprising an apo RAS binding molecule, for instance, prior to administering the apo RAS binding molecule to an individual. Optionally, the kit comprises an applicator for administering the apo RAS binding molecule.

EXPERIMENTAL EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1: Development of Apo RAS Monobodies

New monobodies (R15m1, R15m6, R15m9, R15m10, R15m11, and R15m27) have been isolated and characterized that selectively bind the nucleotide free state of RAS. R15

Monobodies represent the first experimental tools to allow for direct capture of nucleotide-free RAS in cells. Further, the experiments provided herein suggest that certain oncogenic RAS mutants transit through the nucleotide-free state and can be trapped in this state by R15.

These experiments have demonstrated that R15m Monobodies can be used to detect and purify nucleotide free RAS from mammalian cells. This is the first experimental reagent that allows for such detection and purification of this specific state of RAS. More importantly, the experiments demonstrate the utility of R15m Monobodies for specifically inhibiting the signaling and oncogenic activity of specific mutant RAS proteins. The specificity of R15m Monobodies for a particular RAS mutant is determined by the structure of that mutant, i.e., whether it adopts a nucleotide-free like state. It is shown that R15m Monobodies specifically inhibit the following oncogenic RAS mutants: HRAS(Q61L), KRAS (Q61L), NRAS(Q61L), KRAS(G13D), and KRAS(A146T). Each of these mutant RAS proteins spontaneously releases nucleotide at an elevated rate compared to wild type RAS and thus transitions through the nucleotide free state. It is also shown that R15m Monobodies inhibit KRAS(G12D) and NRAS(G12D). Prior studies by others have reported that this particular mutation in RAS proteins induces a conformation that resembles the nucleotide free state thus explaining why R15 targets this mutant. The ability to inhibit the G12D mutant RAS protein is clinically very important given that nearly 100% of pancreatic cancers possess mutant KRAS alleles and the majority of those mutation is G12D mutation. Thus, R15m Monobodies have the potential to serve as a potent inhibitor of pancreatic cancer tumors.

The results of the experiments are now described.

R15m10 Monobody Binds Common Oncogenic RAS Mutants.

Figure 3:
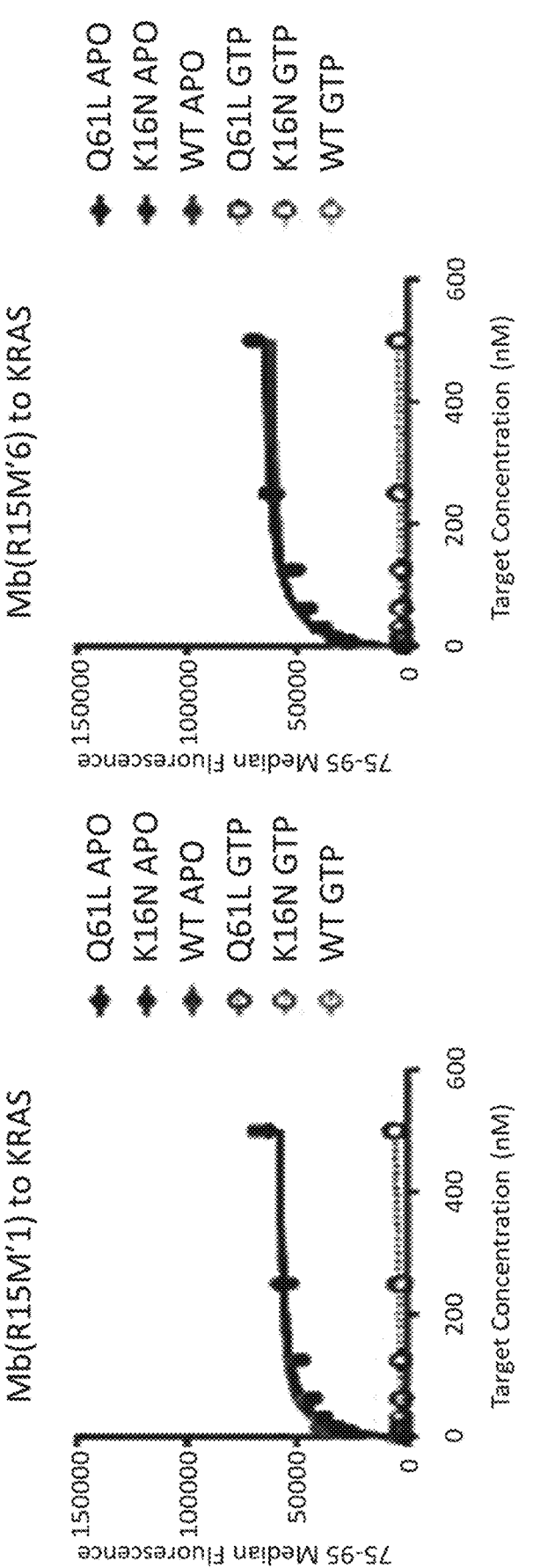
FIG. 3 depicts the in vitro binding titrations of R15m Monobody clones and NS1 Monobody clone as reference for various KRAS mutants in apo or GTP-bound state.
Figure 3:
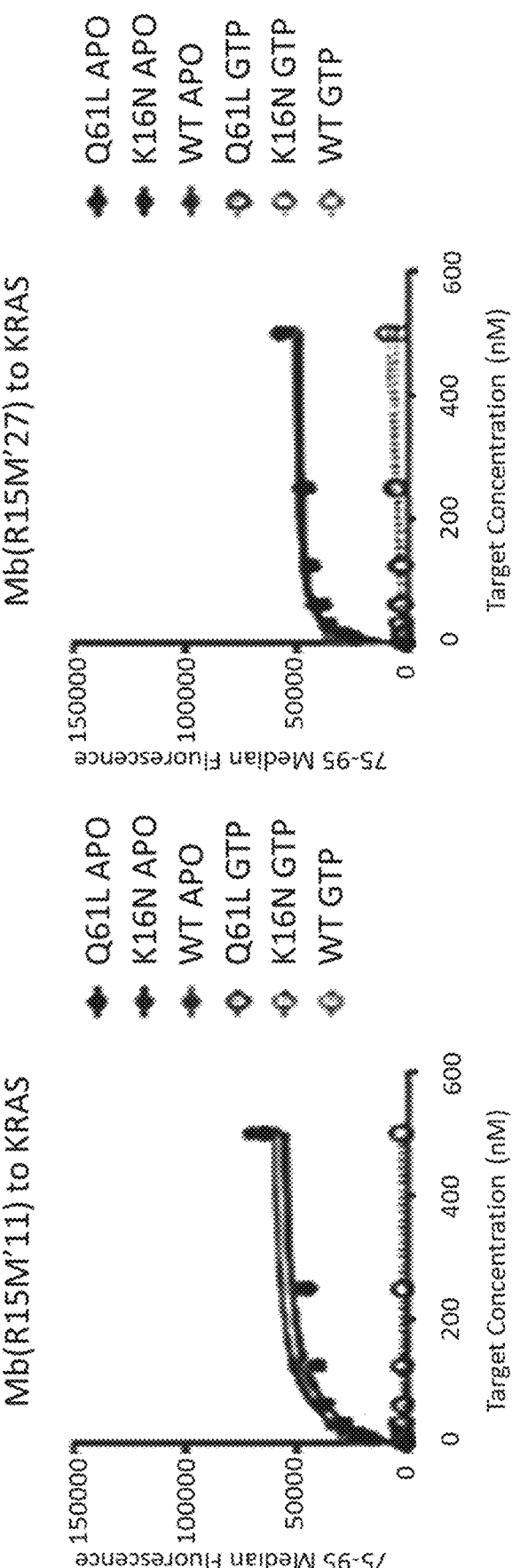
Figure 3:
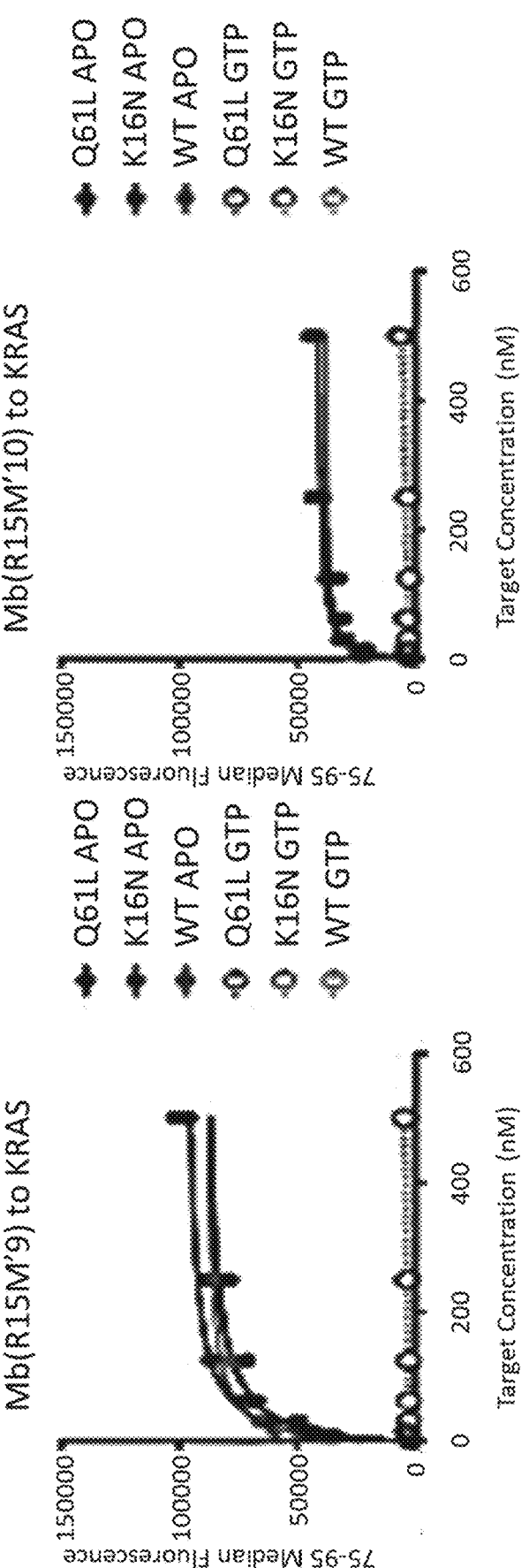
Figure 3:
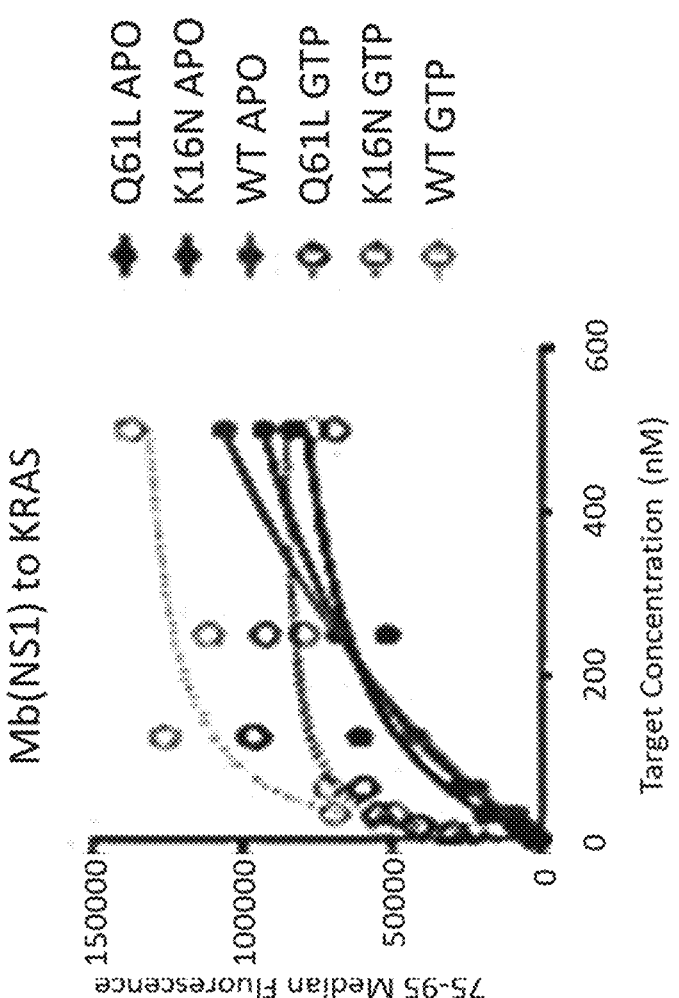

The in vitro binding affinity of apoHRAS for R15 (FIG. 1A and FIG. 2) and R18 (FIG. 1A) was determined using yeast display. The in vitro binding affinity of R15-derived clones (R15m #) for various KRAS mutants in apo or GTP bound state was also determined (FIG. 3 and FIG. 4). R15 clones bind all KRAS mutants in apo state but not GTP-loaded state. Binding of the NS1 monobody (which is agnostic toward the nucleotide state of RAS) was also evaluated for comparison.

Figure 5:
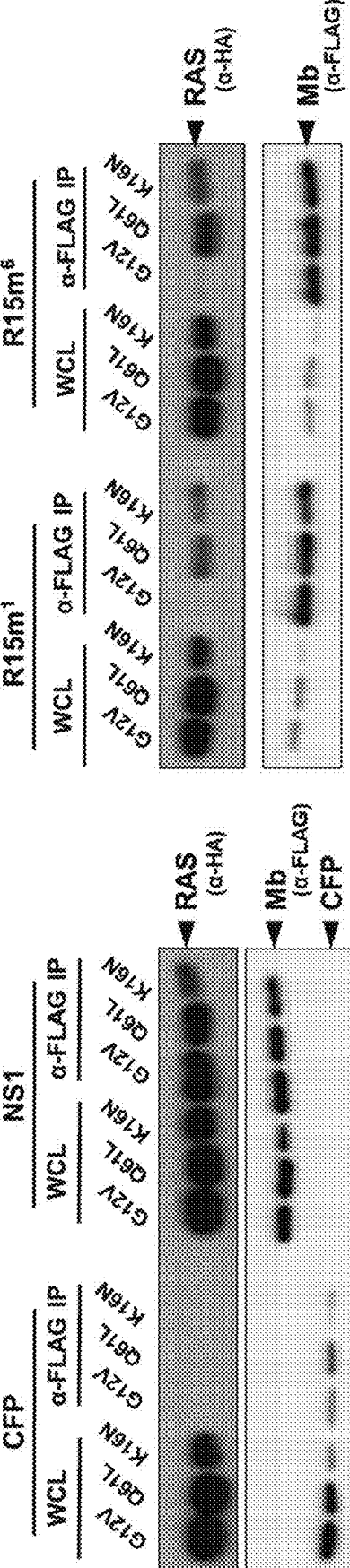
FIG. 5 depicts exemplary data demonstrating the in cell binding profile of modified R15m Monobody clones to HRAS. R15m clones were expressed as CFP-FLAG fusion proteins in HEK cells along with various HA-tagged mutants of HRAS. CFP and NS1 Monobody were used as controls. CFP-FLAG and CFP-FLAG-tagged Monobodies (Mb) were immunoprecipitated, fractioned on SDSPAGE, and probed for binding to HRAS mutants. Antibodies used in Western blots are shown to the right of each panel.
Figure 5:
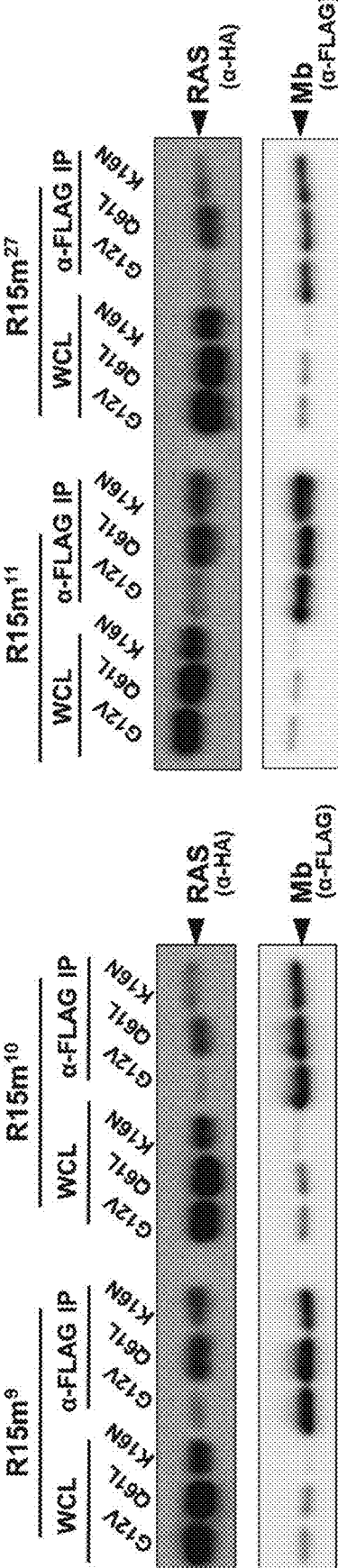
Figure 6:
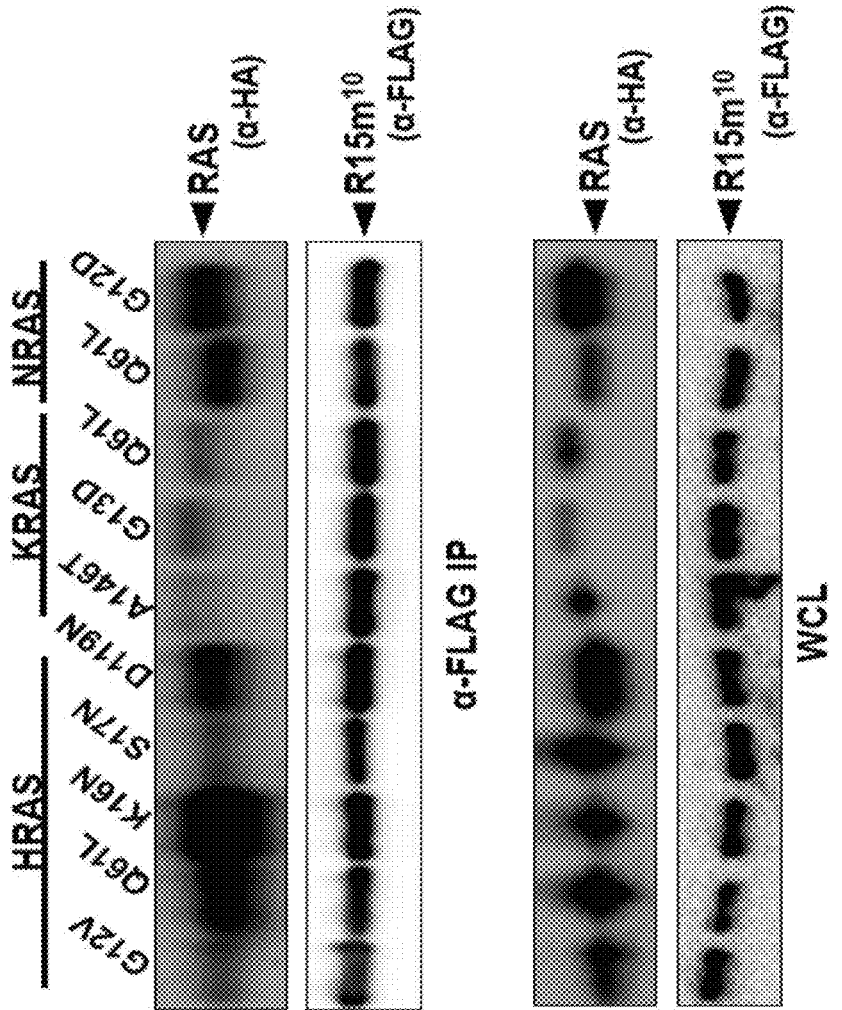
FIG. 6 depicts exemplary data demonstrating in cell binding of R15m10 Monobody to RAS mutants. Experiments were performed as in FIG. 5. FLAG IPs are in the top two panels. The bottom two panels represent Western blots of whole cell lysates to confirm protein expression. Antibodies used in Western blots are shown to the right of each panel.
Figure 7:
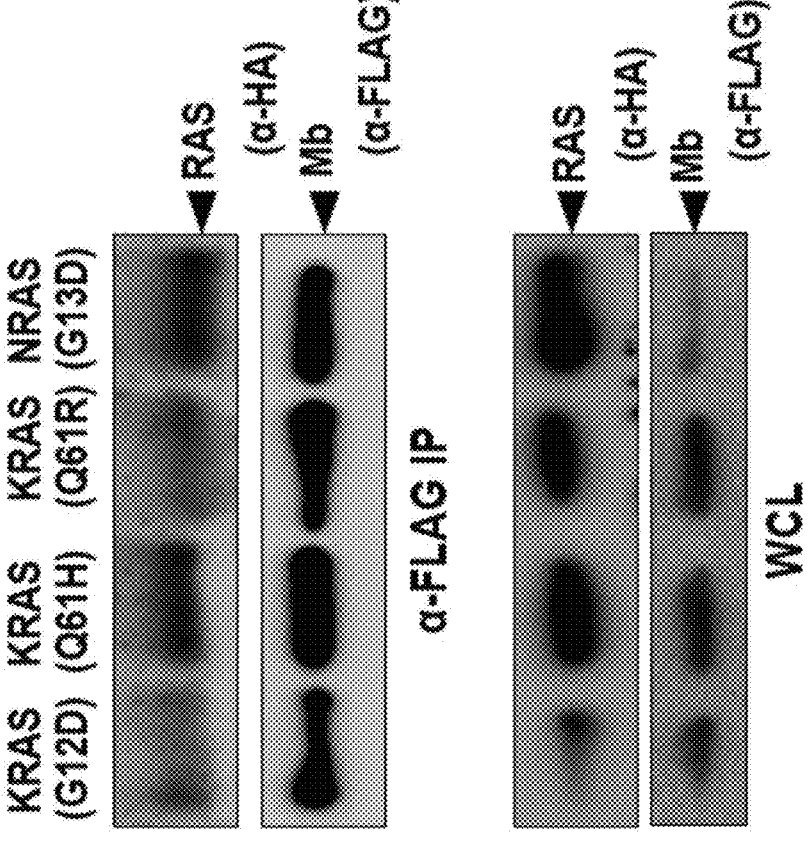
FIG. 7 depicts exemplary data demonstrating that R15m10 Monobody binds common oncogenic KRAS mutants. FLAG IPs are in the top two panels. The bottom two panels represent Western blots of whole cell lysates to confirm protein expression. Antibodies used in Western blots are shown to the right of each panel.
Figure 8:
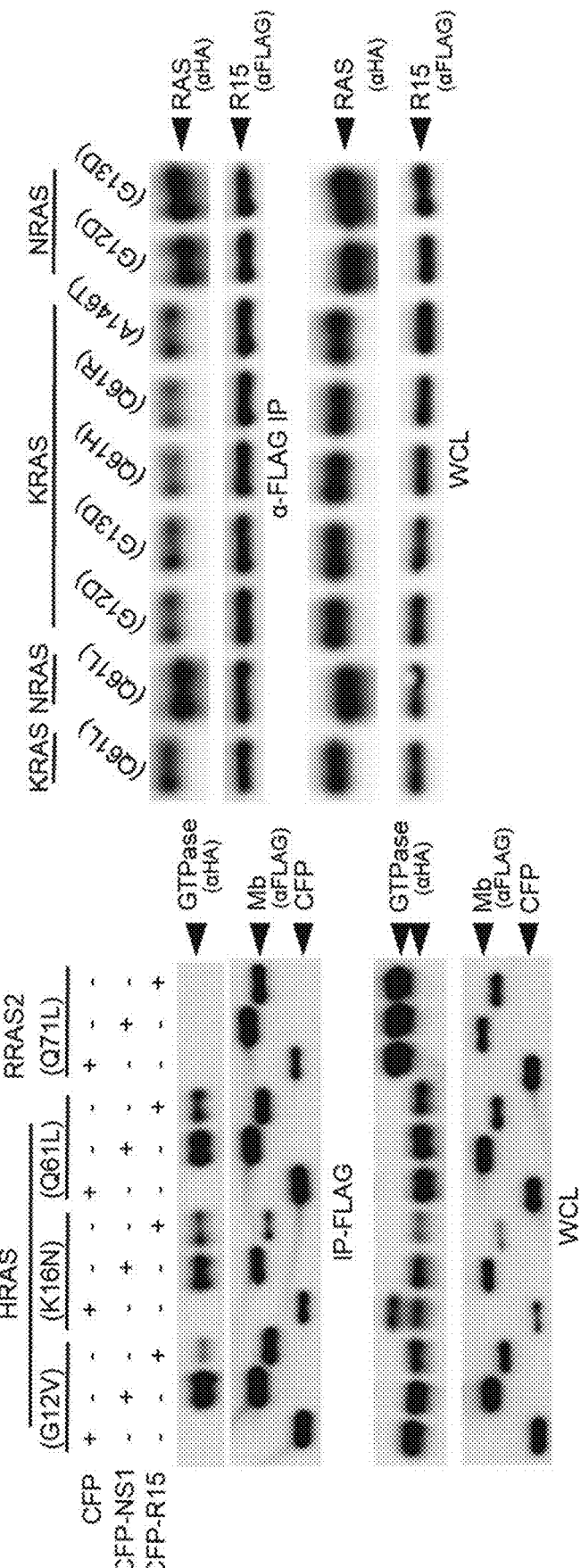
FIG. 8 depicts exemplary data comparing the binding of FLAG-tagged CFP-R15m10 Monobody, CFP or CFP-NS1 to various mutant GTPases. FLAG IPs are in the top two panels. The bottom two panels represent Western blots of whole cell lysates to confirm protein expression. Antibodies used in Western blots are shown to the right of each panel.

R15 or R18 Monobody was expressed as CFP-FLAG fusion proteins in HEK cells along with various HA-tagged mutants of HRAS or KRAS, immunoprecipitated, and probed for binding to RAS mutants (FIGS. 1B and 1C). Additionally, various R15-derivative (R15m #) Monobody clones were expressed as CFP-FLAG fusion proteins in HEK cells along with various HA-tagged mutants of HRAS, immunoprecipitated, and probed for binding to RAS mutants (FIG. 5). R15 and R18 clones bound predominantly to Q61L, D119N, and K16N mutants with little binding to wild type (WT) or G12V mutant. K16N purifies from bacteria in a nucleotide free state. D119N has reduced affinity for nucleotides and Q61L mutant has high intrinsic nucleotide release rate suggesting that R15m Monobodies are trapping these mutants in the nucleotide free (apo) state. R15m10 binds Q61L mutants of all three RAS isoforms in addition to binding to NRAS(G12D) mutant (FIG. 6). Further R15m10 binds common oncogenic RAS mutants (FIG. 7 and FIG. 8).

Expression of R15m10 Monobody Inhibits EGF-Mediated Activation of ERK-MAPK.

HEK cells were transfected with CFP or the indicated CFP-tagged Mb along with MYC-tagged ERK (FIG. 9A).

Cells were then serum starved and stimulated with EGF (100 ng/ml) for 10 min. MYC-ERK was then immunoprecipitated and probed for pERK or total ERK. Expression of Monobodies in whole cell lysates is shown in the bottom panel of FIG. 9A. Both NS1 and R15m10 inhibit ERK activation by EGF.

Intracellular Expression of R15m10 Monobody Inhibits Activation of ERK-MAPK by RAS Mutants which have High Intrinsic Nucleotide Release Rates.

HEK cells were transfected with CFP or the indicated CFP-tagged Mb along with MYC-tagged ERK (FIG. 9B). In addition, various RAS mutants were co-transfected as well. As controls for off-target effects, oncogenic MEK(DD) and BRAF(V600E) were also examined. MYC-ERK was then immunoprecipitated and probed for pERK or total ERK. Expression of the transfected proteins in whole cell lysates (WCL) is shown in the bottom two panels of FIG. 9B. FIG. 9C further demonstrates the effect of CFP-R15m10 on ERK activation by various KRAS and NRAS mutants. FIG. 9D depicts the quantification of ERK activation, where the dotted line indicates the level of ERK activation in CFP-transfected cells for each mutant (normalized to 1). R15m10 selectively inhibits ERK activation by A146T, Q61H, Q61R, Q61L, G13D and G12D mutants but not G12V, MEK(DD) or BRAF(V600E) indicating selectivity toward mutants with fast exchange rates. NS1 selectively inhibits only H and KRAS.

Intracellular Expression of R15m10 Monobody Inhibits Activation of ERK-MAPK by Prominent RAS Mutants.

Figure 10:
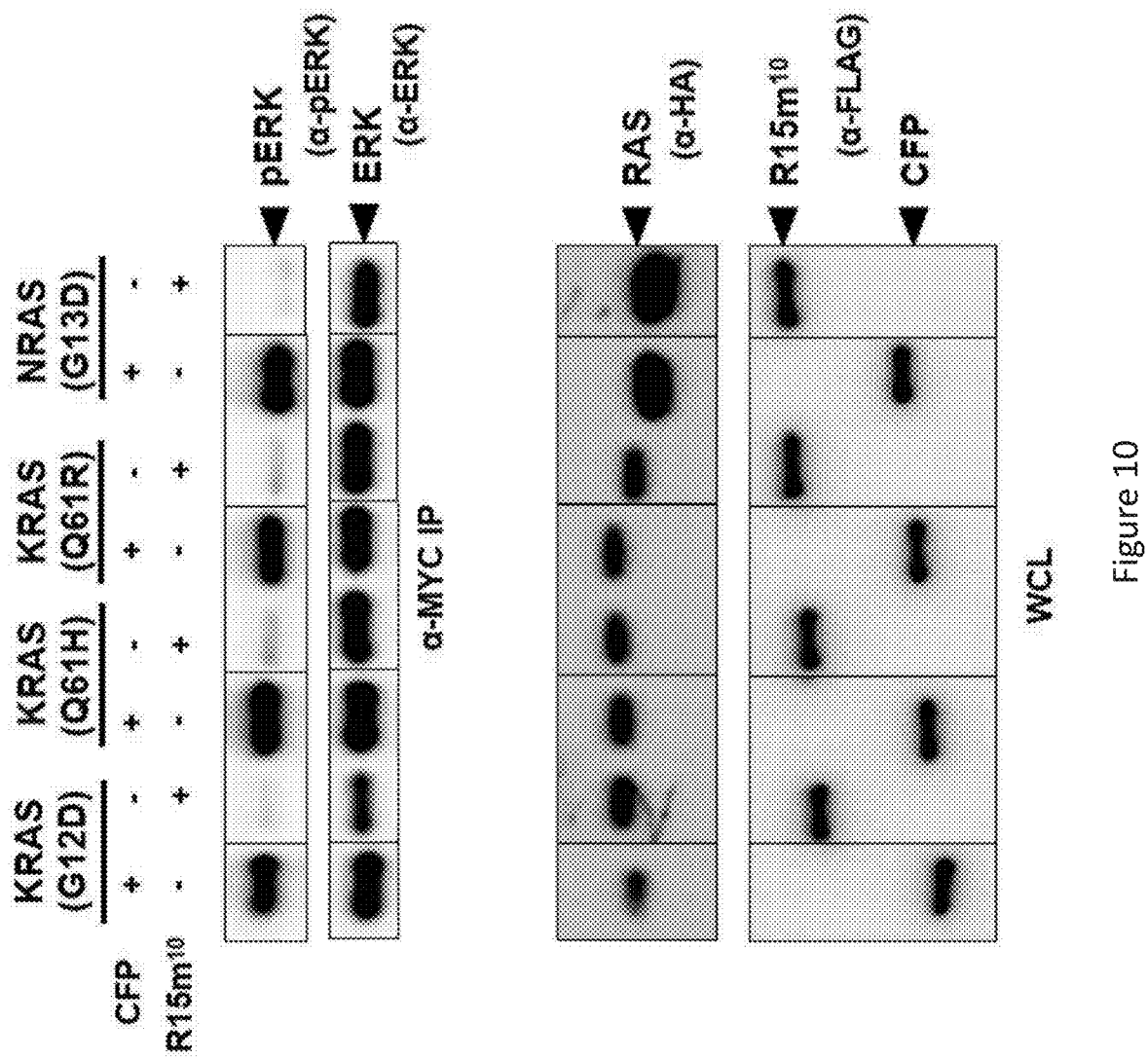
FIG. 10 depicts exemplary data demonstrating that R15m10 Monobody inhibits MAPK activation by high frequency RAS oncogenic mutants All samples in a particular panel were run on same gel and probed at same time. Vertical line indicates a lane containing an irrelevant sample was deleted from the image.

Experiments were performed as in FIG. 9 with RAS mutants that are present at high frequency in human tumors. Expression of R15m10 inhibits activation of ERK-MAPK by these RAS mutants (FIG. 10). Expression of the transfected proteins in whole cell lysates (WCL) is shown in the bottom 2 panels of FIG. 10.

R15m10 Binds Nucleotide Free RAS in Cells

HEK cells were co-transfected with the indicated Mb and HA-tagged RAS mutant. Monobodies were subsequently immunoprecipitated with FLAG antibodies to purify the associated RAS mutant protein. IPs were washed extensively with buffer containing high Mg2+ and lacking nucleotide. RAS proteins were then eluted from the immune complex with buffer containing low concentrations of SDS and deoxycholate (DOC). Eluted RAS proteins were then recovered and diluted 10-fold with buffer lacking SDS and DOC. Purified RAS proteins were then normalized to equivalent levels and incubated with GST-RAF-RBD to determine the level of active GTP-loaded RAS. As indicated, NS1 purified RAS-GTP as the purified RAS proteins robustly bound GST-RAF RBD both in the absence and presence of added GTPγS (FIG. 11A-D). In contrast, R15m10 purified RAS proteins did not interact with GST-RAF RBD indicating that they were not in the active, GTP-bound state despite being oncogenic RAS mutants. However, addition of GTPγS (+GTP) to the R15m10 purified RAS proteins reconstituted binding to the RAF-RBD (FIG. 11A-D). FIGS. 11E and 11F depict total expression of proteins with NS1 and R15, respectively, in whole cell lysates (WCL). FIG. 12 demonstrates that monobody-purified RAS proteins are not spontaneously exchanging nucleotide in vitro. HEK cells were co-transfected with the indicated Mb and RAS mutant as in FIG. 11 and RAS proteins bound to Monobodies purified as described in FIG. 11. FIG. 12A results recapitulate the results in FIGS. 11C and 11D. FIG. 12B indicates that purified RAS-GTP does not spontaneously release nucleotide since addition of GDP to the NS1 purified RAS-GTP does not result in reduced binding to GST-RAF RBD. FIG. 12C indicates the relative amounts of RAS immunoprecipitated with the indicated Monobody. FIG. 12D indicates the relative expression of each protein in whole cell lysates. These results in FIGS. 11 and 12 together indicate that the R15m10-purified oncogenic RAS proteins were initially nucleotide-free and unable to bind RAF-RBD and that addition of GTPγS resulted in activation of the RAS proteins and binding to RAF-RBD.

R15m10 Inhibits the Oncogenic Transformation of NIH/3T3 Cells by Fast Cycling RAS Mutants.

Figure 13A:
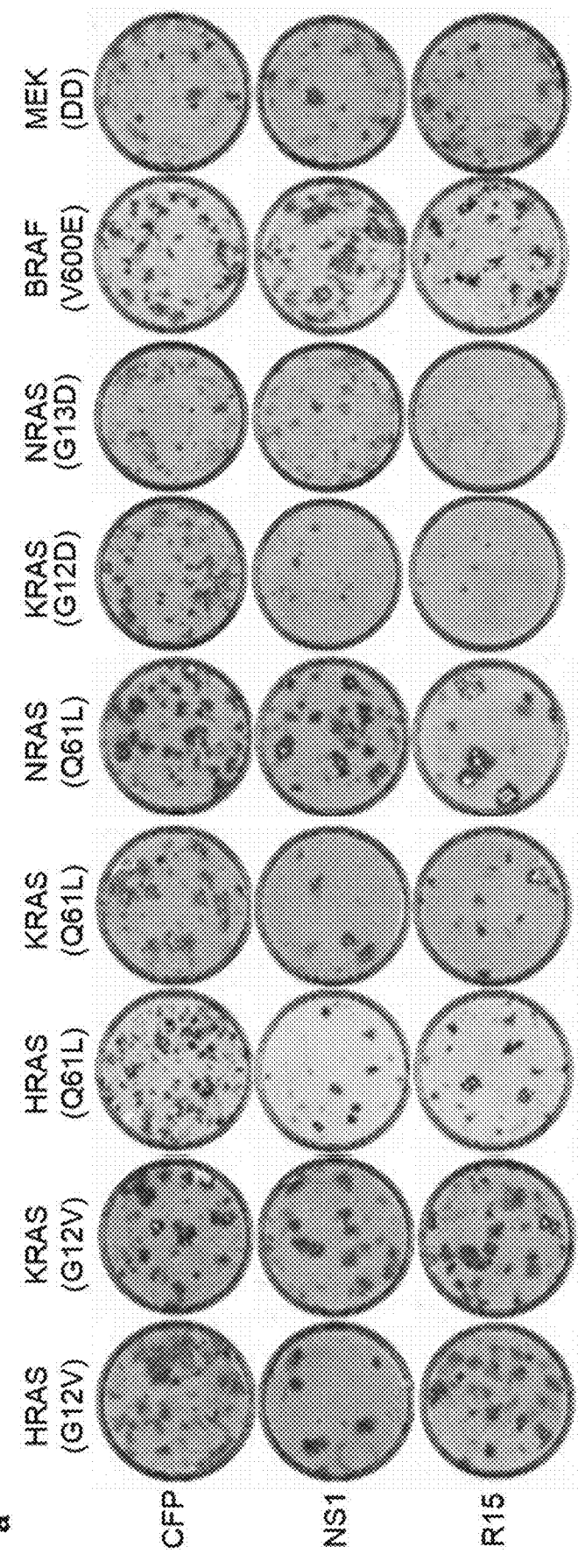
FIGS. 13A and 13B depict exemplary data demonstrating that R15m10 inhibits the oncogenic transformation of NIH/3T3 cells by fast cycling RAS mutants.
Figure 13B:
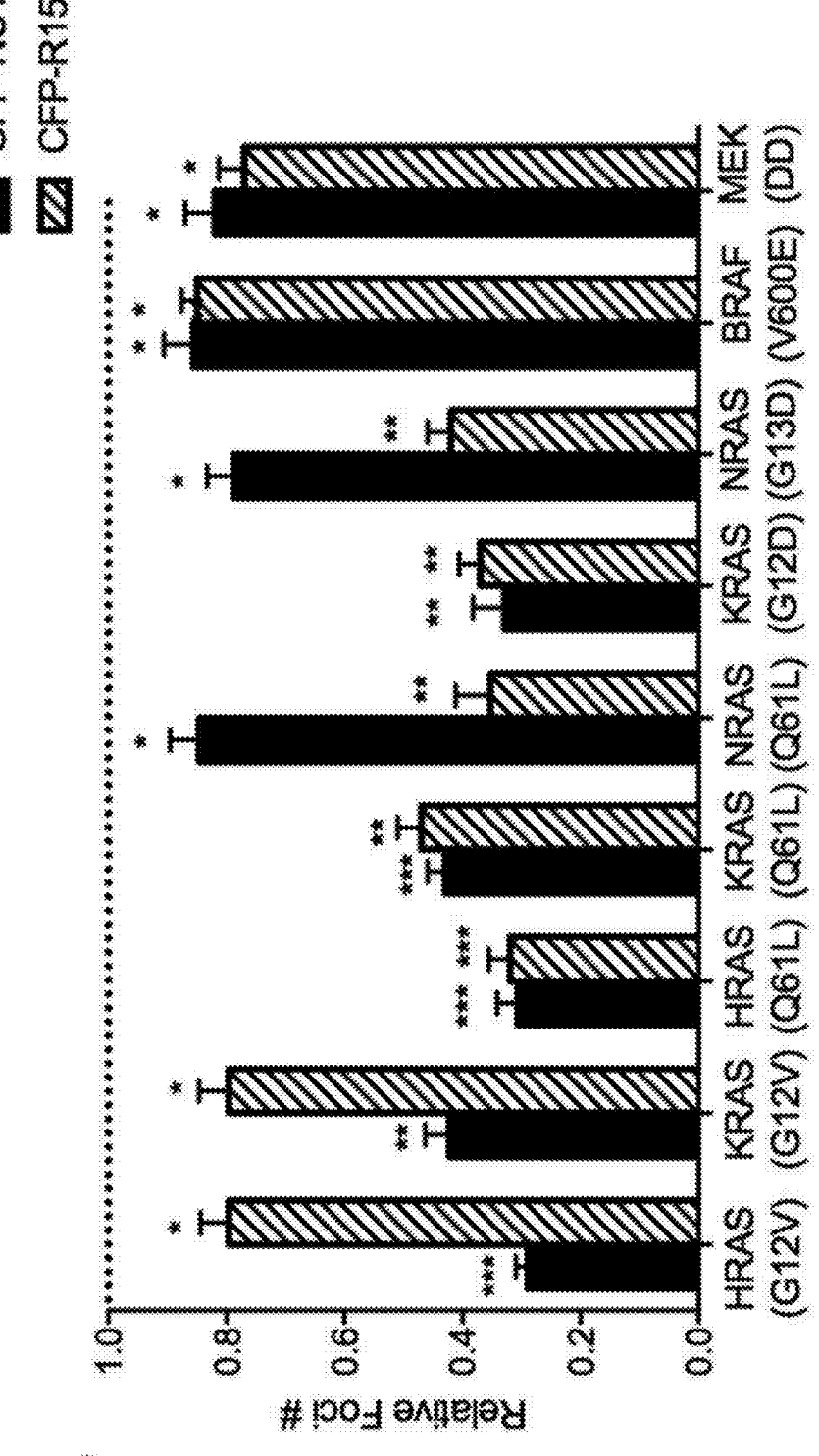

Cells were transfected with the indicated RAS mutants and the indicated CFP or CFP-tagged Mb and allowed to sit at confluence for 2-3 weeks. Foci were stained with crystal violet. NS1 was used as a control for inhibition of KRAS and HRAS mutants. R15m10 selectively inhibited Q61L mutants of all three RAS isoforms but did not affect G12V mutants (FIGS. 13A and B). Neither monobody affected transformation by oncogenic BRAF or MEK mutants (FIGS. 13A and B), further demonstrating selectivity and lack of off-target effects.

Exchange Factor Binding to RAS Inhibits R15m10-RAS Interaction in Cells

Figure 14C:
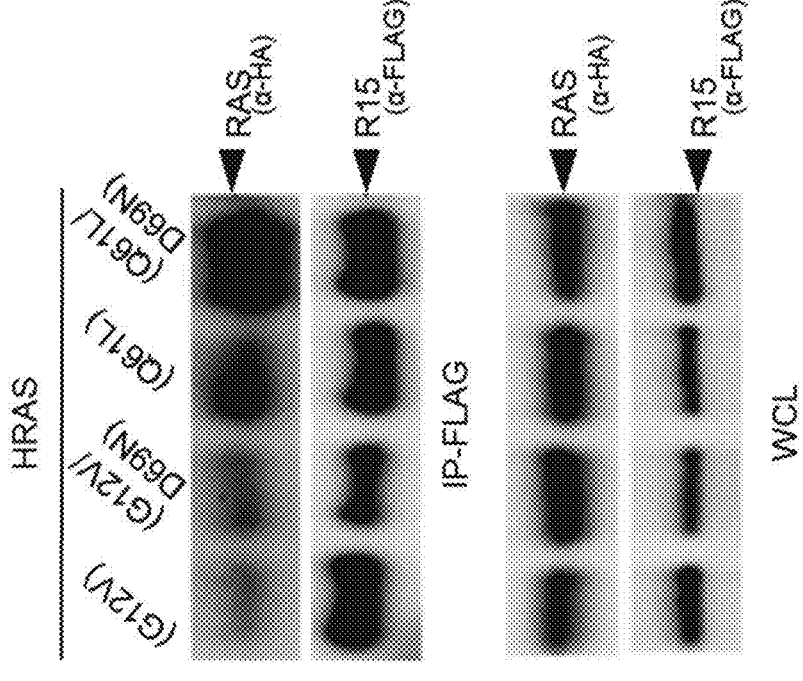

Co-immunoprecipitation of FLAG-tagged CFP-R15m10 with the indicated HRAS mutant was examined in the presence (+) or absence (−) of serum. Serum depletion significantly enhances R15m10 binding to HRAS(Q61L), a fast cycling RAS mutant, suggesting that exchange factors are not needed for creation of apoRAS and binding R15m10 (FIG. 14A). Additional experiments in the presence and absence of serum further demonstrates that mutation of the GEF binding interface on RAS enhances RAS interaction with apo-specific monobody R15m10. Disrupting KRAS interaction with exchange factors by mutation D69N increased interaction of KRAS with apo-specific Monobody R15 (FIG. 14B). FIG. 14C depicts experiments performed as in FIG. 14B with HRAS mutants but only under serum-starved conditions.

R15m10 Disrupts Binding of Fast-Cycling RAS Mutants with CRAF

HEK cells were co-transfected with CFP or the indicated CFP-tagged Mb. Cells were then serum starved and then cell lysates immunoprecipitated with antibodies to CRAF. These CRAF IPs were then fractionated on SDS-denaturing gels, and analyzed by Western blot for the co-association of CRAF with the indicated proteins. R15m10 disrupts interaction of CRAF with fast-cycling RAS mutants (FIG. 15A, top panel) and the heterodimerization with BRAF (FIG. 15A, *2nd* panel from top). NS1 does not affect NRAS interaction with CRAF or CRAF:BRAF heterodimerization as previously described (FIG. 15A; Spencer-Smith et al (2017) Nat Cell Biol). FIG. 15B further demonstrates that R15m10 disrupts RAS:CRAF interactions and CRAF: BRAF heterodimerization by KRAS(Q61L) and NRAS (G12D) fast cycling mutants but not NRAS(G12V) slow cycling mutant. NS1 does not affect CRAF interactions with NRAS as expected (FIG. 15B).

Inducible Expression of R15m10 Inhibits Signaling, Proliferation, Anchorage-Independent Growth and Tumor Development of Cell Lines Driven by Fast-Cycling RAS Mutants Stable tumor cell lines in which R15m10 expression was induced by treatment with doxycycline (DOX) were generated and ERK-MAPK activation was measured in the absence (−DOX) or presence (+DOX) of R15 expression. ERK-MAPK signaling was inhibited in tumor cell lines driven by fast cycling RAS mutants upon induction of R15m10 expression (FIG. 16A-D), but not in a cell line expressing a slow cycling mutant (FIG. 16E). Proliferation was measured using CellTiterGlo over the indicated time periods in the absence (−DOX) or presence (+DOX) of R15 expression. Induction of R15m10 expression inhibited proliferation of tumor lines with fast cycling RAS mutations (FIG. 16F-I), but not in a cell line expressing a slow cycling mutant (FIG. 16J). Anchorage-independent growth of the inducible tumor cell lines was measured by plating in soft agar in the absence or presence of DOX and growing for 3-4 weeks. Expression of R15 (+DOX) reduced anchorage-independent growth in lines expressing fast cycling RAS mutants (FIG. 17A-D), but not in a cell line expressing a slow cycling mutant (FIG. 17E). In vivo tumor development was measured by subcutaneously injecting R15m10 expressing DOX-inducible tumor cells into the flanks of athymic nude mice. R15m10 expression reduced tumor volume and ERK-MAPK signaling of KRAS(G12D) mutant PANC-1 cells (FIG. 18), HRAS(Q61L) mutant H1915 cells (FIG. 20) and KRAS(G12D) mutant HCT116 cells (FIG. 21), but not KRAS(G12V) mutant CFPAC-1 cells (FIG. 19), again demonstrating the specificity of R15m10 towards fast cycling but not slow cycling RAS mutants.

SEQUENCES
R15m1

(SEQ ID NO: 1)
VSSVPTKLEVVAATPTSLLISWDASSSSVSYYRITYGETGGNPPVQEFTVP

GYYSTATISGLKPGVDYTITVYAVWQGVWRYVSPISINYRT

R15m6

(SEQ ID NO: 2)
VSSVPTKLEVVAATPTSLLISWDASSSSVSYYRITYGETGGNSPVQEFTVP

GYYPTATISGLKPGVDYTITVYAVWQGVWRYVSPISINYRT

R15m9

(SEQ ID NO: 3)
VSSVPTKLEVVAATPTSLLISWDASSSSVSYYRITYGETGGNSPVQEFTVP

GYYSTATISGLKPGVDYTITVYAVWFGHWLYVSPISINYRT

R15m10

(SEQ ID NO: 4)
VSSVPTKLEVVAATPTSLLISWDASSSSVSYYRITYGETGGNSPVQEFTVP

GYYSTATISGLKPGVDYTITVYAVWQGVWRYVSPISINYRT

R15m11

(SEQ ID NO: 5)
VSSVPTKLEVVAATPTSLLISWDASSSSVSYYRITYGETGGSSPVQEFTVP

GYYSTATISGLKPGVDYTITVYATWVGVWVYVSPISINYRT

R15m27

(SEQ ID NO: 6)
VSSVPTKLEVVAATPTSLLISLDASSSSVSYYRITYGETGGNSPVQEFTVP

GYYSTATISGLKPGVDYTITVYAFRRKKWSYISPISINYRT

R15m2

(SEQ ID NO: 7)
VSSVPTKLEVVAATPTSLLISWDASSSSVSYYRITYGETGGNSPVQEFTVP

GYYSTATISGLKPGVDYTITVYATWVGVWVYVSPISINYRT

R15mm2

(SEQ ID NO: 8)
VSSVPTKLEVVAATPTSLLISWDASSSSVSYYRITYGETGGNSPVQEFTVP

GYYSTATISGLKPGVDYTITVYAVWFKKWLYVSPISINYRTEIDK

R15mm4

(SEQ ID NO: 9)
VSSVPTKLEVVAATPTSLLISWDASSSSVSYYRITYGETGGNSPVQEFTVP

GYYSTATISGLKPGVDYTITVYAVWFGKWLYVSPISINYRTEIDK

R15mm7

(SEQ ID NO: 10)
VSSVPTKLEVVAATPTSLLISWDASSSSVSYYRITYGETGGNSPVQEFTVP

GYYSTATISGLKPGVDYTITVYAVSFGHWLYVSPISINYRTEIDK

R15mm8

(SEQ ID NO: 11)
VSSVPTKLEVVAATPTSLLISWDASSSSVSYYRITYGETGGNSPVQEFTVP

GYYSTATISGLKPGVDYTITVYAVWSGHWLYVSPISINYRTEIDK

R15mm9

(SEQ ID NO: 12)
VSSVPTKLEVVAATPTSLLISWDASSSSVSYYRITYGETGGNSPVQEFTVP

GYYSTATISGLKPGVDYTITVYAVWFGSWLYVSPISINYRTEIDK

R15mm11

(SEQ ID NO: 13)
VSSVPTKLEVVAATPTSLLISWDASSSSVSYYRITYGETGGNSPVQEFTVP

GYYSTATISGLKPGVDYTITVYAVWFGHWSYVSPISINYRTEIDK

R15mm13

(SEQ ID NO: 14)
VSSVPTKLEVVAATPTSLLISWDASSSSVSYYRITYGETGGNSPVQEFTVP

GYYSTATISGLKPGVDYTITVYAVWFGHWLYSSPISINYRTEIDK

R15m9-8

(SEQ ID NO: 15)
VSSVPTKLEVVAATPTSLLISWDASSSSVSYYRITYGETGGNSPVQEFTVP

GYYSTATISGLKPGVDYTITVYAVWEGKWLYVSPISINYRT

R15m9-17

(SEQ ID NO: 16)
VSSVPTKLEVVAATPTSLLISWDASSSSVSYYRITYGETGGNSPVQEFTVP

GYYSTATISGLKPGVDYTITVYAISAGYWLYVSPISINYRT

R15m9-19

(SEQ ID NO: 17)
VSSVPTKLEVVAATPTSLLISWDASSSSVSYYRITYGETGGNSPVQEFTVP

GYYSTATISGLKPGVDYTITVYAVSSGYWLYVSPISINYRT

R15m9-30

(SEQ ID NO: 18)
VSSVPTKLEVVAATPTSLLISWDASSSSVSYYRITYGETGGNSPVQEFTVP

GYYSTATISGLKPGVDYTITVYAIWSGHWLYVSPISINYRT

R15m9-38

(SEQ ID NO: 19)
VSSVPTKLEVVAATPTSLLISWDASSSSVSYYRITYGETGGNSPVQEFTVP

GYYSTATISGLKPGVDYTITVYASWEGRWLYVSPISINYRT

R15m9-49

(SEQ ID NO: 20)
VSSVPTKLEVVAATPTSLLISWDASSSSVSYYRITYGETGGNSPVQEFTVP

GYYSTATISGLKPGVDYTITVYASWEGKWLYVSPISINYRT

R15m9-8-DE-3

(SEQ ID NO: 21)
VSSVPTKLEVVAATPTSLLISWDASSSSVSYYRITYGETGGNSPVQEFTVP

GYYDTATISGLKPGVDYTITVYAVWEGKWLYVSPISINYRT

R15m9-8-DE-9

(SEQ ID NO: 22)
VSSVPTKLEVVAATPTSLLISWDASSSSVSYYRITYGETGGNSPVQEFTVP

GSDHTATISGLKPGVDYTITVYAVWEGKWLYVSPISINYRT

R15m9-8-DE-12

(SEQ ID NO: 23)
VSSVPTKLEVVAATPTSLLISWDASSSSVSYYRITYGETGGNSPVQEFTVP

GYSHTATISGLKPGVDYTITVYAVWEGKWLYVSPISINYRT

R15m9-8-DE-15

(SEQ ID NO: 24)
VSSVPTKLEVVAATPTSLLISWDASSSSVSYYRITYGETGGNSPVQEFTVP

GDYATATISGLKPGVDYTITVYAVWEGKWLYVSPISINYRT

R15m9-8-DE-16

(SEQ ID NO: 25)
VSSVPTKLEVVAATPTSLLISWDASSSSVSYYRITYGETGGNSPVQEFTVP

GAAATATISGLKPGVDYTITVYAVWEGKWLYVSPISINYRT

R15m9-8-DE-19

(SEQ ID NO: 26)
VSSVPTKLEVVAATPTSLLISWDASSSSVSYYRITYGETGGNSPVQEFTVP

GSASTATISGLKPGVDYTITVYAVWEGKWLYVSPISINYRT

R15m9-8-FG7-8

(SEQ ID NO: 27)
VSSVPTKLEVVAATPTSLLISWDASSSSVSYYRITYGETGGNSPVQEFTVP

GYSHTATISGLKPGVDYTITVYAVWEGKWVYVSPISINYRT

R15m9-8-FG7-10

(SEQ ID NO: 28)
VSSVPTKLEVVAATPTSLLISWDASSSSVSYYRITYGETGGNSPVQEFTVP

GDYATATISGLKPGVDYTITVYAVWEGKWTYVSPISINYRT

R15m9-8-FG7-16

(SEQ ID NO: 29)
VSSVPTKLEVVAATPTSLLISWDASSSSVSYYRITYGETGGNSPVQEFTVP

GYSHTATISGLKPGVDYTITVYAVWEGKWKYVSPISINYRT

R15m9-8-FG7-17

(SEQ ID NO: 30)
VSSVPTKLEVVAATPTSLLISWDASSSSVSYYRITYGETGGNSPVQEFTVP

GDYATATISGLKPGVDYTITVYAVWEGKWAYVSPISINYRT

R15m9-8-FG7-34

(SEQ ID NO: 31)
VSSVPTKLEVVAATPTSLLISWDASSSSVSYYRITYGETGGNSPVQEFTVP

GYSHTATISGLKPGVDYTITVYAVWEGKWRYVSPISINYRT

R15m9-8-FG7-42

(SEQ ID NO: 32)
VSSVPTKLEVVAATPTSLLISWDASSSSVSYYRITYGETGGNSPVQEFTVP

GSDHTATISGLKPGVDYTITVYAVWEGKWVYVSPISINYRT

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A composition comprising at least one molecule comprising a monobody domain that selectively binds RAS in a nucleotide free state (apo RAS) but not RAS in the nucleotide-bound state, wherein the monobody domain comprises a sequence selected from the group consisting of SEQ ID NO: 1-6.

2. The composition of claim 1, wherein the composition further comprises a fusion protein fused to the monobody domain or a peptide comprising the monobody domain.

3. The composition of claim 2, wherein the fusion protein comprising a monobody domain further comprises a therapeutic agent or a detection moiety.

4. An isolated nucleic acid molecule encoding the molecule of claim 1 that selectively binds apo RAS but does not bind to nucleotide-bound RAS.

5. An expression vector comprising the nucleic acid molecule of claim 4.

6. A host cell comprising the nucleic acid molecule of claim 4.

* * * * *